United States Patent [19]

Thomas et al.

[11] Patent Number: 5,630,413

[45] Date of Patent: *May 20, 1997

[54] RELIABLE NONINVASIVE MEASUREMENT OF BLOOD GASES

[75] Inventors: Edward V. Thomas; Mark R. Robinson; David M. Haaland, all of Albuquerque; Mary K. Alam, Cedar Crest, all of N.M.

[73] Assignee: Sandia Corporation, Albuquerque, N.M.

[*] Notice: The term of this patent shall not extend beyond the expiration date of Pat. No. 5,355,880.

[21] Appl. No.: 257,875

[22] Filed: Aug. 12, 1994

Related U.S. Application Data

[63] Continuation of Ser. No. 910,004, Jul. 6, 1992, Pat. No. 5,355,880.

[51] Int. Cl.⁶ .................................................. A61B 5/00
[52] U.S. Cl. ................................................... 128/633
[58] Field of Search ..................... 128/633–4, 664–7, 128/635, 637; 356/39–41; 436/68

[56] References Cited

U.S. PATENT DOCUMENTS

| | | |
|---|---|---|
| 4,041,932 | 8/1977 | Fostick . |
| 4,114,604 | 9/1978 | Shaw et al. . |
| 4,201,222 | 5/1980 | Hasse . |
| 4,274,418 | 6/1981 | Vesterager et al. . |
| 4,324,256 | 4/1982 | Vesterager et al. . |
| 4,509,522 | 4/1985 | Manuccia . |
| 4,682,985 | 7/1987 | Costello . |
| 4,685,465 | 8/1987 | Klitgaard et al. . |
| 4,694,834 | 9/1987 | Myeroff et al. . |
| 4,834,532 | 5/1989 | Yount . |
| 4,854,321 | 8/1989 | Boiorski . |
| 4,930,506 | 6/1990 | Ullrich . |
| 4,975,581 | 12/1990 | Robinson et al. . |
| 4,989,606 | 2/1991 | Gehrich et al. . |
| 5,103,829 | 4/1992 | Suzuki et al. . |
| 5,355,880 | 10/1994 | Thomas et al. ............... 128/633 |

*Primary Examiner*—Angela D. Sykes
*Attorney, Agent, or Firm*—DeWitt M. Morgan, Esq.

[57] ABSTRACT

This invention relates to methods and apparatus for, preferably, determining non-invasively and in vivo at least two of the five blood gas parameters (i.e., pH, $[HCO_3^-]$, $PCO_2$, $PO_2$, and $O_2$sat.) in a human.

36 Claims, 50 Drawing Sheets

RELIABLE NONINVASIVE MEASUREMENT OF BLOOD GASES

This invention was made with Government support and the Government has certain rights in this invention.

This is a continuation of application Ser. No. 07/910,004 filed on Jul. 6, 1992 now U.S. Pat. No. 5,355,880.

BACKGROUND OF INVENTION

This invention relates to both a method and apparatus (as illustrated in FIG. 1) for, particularly, the noninvasive determination of those parameters currently reported on a standard clinical arterial blood gas report. The parameters typically reported are hydrogen ion concentration (pH) partial pressure of carbon dioxide ($PCO_2$), partial pressure of oxygen ($PO_2$), bicarbonate concentration ($[HCO_3^-]$) and oxygen saturation ($O_2$sat.).

Arterial blood gas determination is the cornerstone of diagnosis and management of cardiopulmonary disease in the critically ill patient. As effective oxygenation and maintenance of acid-base balance in such a patient is necessary for survival, measurement of arterial blood gases is typically the most frequently ordered laboratory test in a hospital's intensive care unit. In a patient with respiratory failure, the physician uses the results of blood gas analysis to optimize such a patient's oxygenation and acid-base status. Specifically, decisions regarding oxygen administration, titration of positive end expiratory pressure (PEEP) and minute ventilation are made, at least in part, on the results of arterial blood gas analysis. Repeated determinations are made over time to monitor the progression or remission of cardiopulmonary pathophysiology and to guide efforts at weaning patients from mechanical ventilatory support.

The standard arterial blood gas report contains the following information: pH, $PCO_2$, $PO_2$, $[HCO_3^-]$, and $O_2$ saturation. The pH and $PCO_2$ provide valuable information regarding acid-base and ventilation status. The bicarbonate level provides additional information on acid-base balance which allows the physician to determine whether an acid-base abnormality is respiratory or metabolic in origin. The two other indices, $PO_2$ and $O_2$ saturation, reflect the amount of oxygen present in the patient's blood.

At the present time standard clinical practice requires arterial puncture for procurement of an arterial blood sample. The arterial puncture is painful to the patient and associated with a variety of complications. Minor complications include arteriospasm, localized internal bleeding (i.e. hematoma), transient occlusion of the artery and temporary loss of sensation in the distribution of the median nerve. Major complications are infrequent, but include hemorrhage and severe vascular occlusion secondary to intraluminal clot formation. On rare occasions, gangrene has necessitated the amputation of a finger or a hand. When multiple samples are required over a relatively short period of time, an indwelling arterial catheter may be useful, the insertion of which can also be painful and which has complications such as described above. Although a standard indwelling arterial catheter allows for repeated sampling, it does not allow for continuous arterial blood gas monitoring.

The necessity, as well as associated complications, of blood gas monitoring are also present when monitoring infants, especially premature infants. The ventilation of premature infants is especially difficult due the immaturity of their lungs. Thus, to optimize the infants chances for survival, the pediatrician or neonatologist must obtain multiple arterial blood gas determinations. Arterial puncture for procurement of the required arterial sample from an infant is typically more difficult than in adults due to the smaller size of the arteries.

In addition to the foregoing, the process for analyzing the arterial blood sample is lengthy, requires multiple personnel and is not continuous. Immediately after withdrawal, the arterial blood sample is placed on ice to inhibit red blood cell metabolism, which metabolism would alter the sample's blood gas parameters and lead to an incorrect measurement of the patients blood gas values. The sample is then transported to the clinical chemistry laboratory in the hospital where it is logged in. Next, the sample is then analyzed by conventional electrochemical techniques. Finally, the results are entered in the hospital computer and made available to the physician for interpretation.

Due to the important clinical role of the information obtained by arterial blood gas analysis in the management of critically ill patients and the drawbacks of conventional clinical analysis, a number of alternative technologies have been proposed to measure one or more blood gas parameters. The prior art is quite diverse but can be divided into 7 major categories.

1. Invasive colorimetric technologies requiring direct contact between the colorimetric substances and arterial blood. These technologies measure pH, $PO_2$, and $PCO_2$.

2. Separation of the blood gases by semipermeable membranes, with subsequent concentration determination by absorption spectroscopy. The technology is limited to the measurement of $PO_2$, and $PCO_2$.

3. Electrode devices for measurement of $PO_2$, and $PCO_2$ in peripheral skin. This technology has been commercially developed by Radiometer, Denmark.

4. Invasive transistor devices for measurement of pH, and $PCO_2$ in blood.

5. Semi-invasive techniques for measurement of pH, $PCO_2$ and $PO_2$ in peripheral skin.

6. Optical or spectroscopic determination of $PCO_2$ and PCO (partial pressure of carbon monoxide) in tissue;

7. Pulse oximeters for noninvasive measurement of arterial blood oxygen saturation ($O_2$sat.).

The terminology used in clinical medicine, technical publications and the prior art patents is not always consistent. In the clinical practice of medicine the term "blood gas" is specific for the determination of certain factors in arterial blood. The determination of blood gases in venous blood is of little or no clinical significance and is not standard practice. Technically the term "blood gas" is misleading as not all of the components listed on a standard laboratory blood gas report are specific for gas measurements. PH and $[HCO_3^-]$ are concentration measurements of non-gaseous substances. In this application "blood gas parameters" are pH, $PCO_2$, $PO_2$, or $[HCO_3^-]$ and $O_2$ saturation.

The foregoing parameters are not always measured in arterial blood; they can be measured in tissue and skin. Thus, it is important to distinguish between measurement in arterial blood, tissue and peripheral skin, as their sensitivity and clinical utility differ. Blood gas measurements in arterial blood are currently the reference standard used in clinical medicine and the associated body of knowledge on how to interpret the results is extensive. Additionally there is a minimal time delay between a change in cardiopulmonary status and a corresponding change in arterial blood concentrations.

Several prior art methodologies measure certain blood gas parameters in the peripheral skin or tissue. Peripheral skin and tissue are differentiated in that skin is the outermost layer of the body, while tissue refers to the sum total of body mass existing between two skin surfaces. Thus, a tissue measurement will contain information on the dermal and epidermal layers of the skin, muscle, bond, fat, blood vessels and capillaries. Tissue measurements, if accurate, may be the measurements of highest clinical utility as such measurements define the acid-base and oxygen status of the peripheral tissue. The maintenance of normal physiology in these tissues is the goal when treating cardiopulmonary disease. However, as current clinical instrumentation does not measure tissue blood gas parameters, the practicing physician will be unfamiliar in how to interpret these measurements. Additionally there may be a longer time delay between changes in cardiopulmonary status and a corresponding change in the tissue.

Measurement of blood gas parameters in peripheral skin has limited clinical utility. When peripheral skin measurements are compared to arterial blood measurements, it has been found that the skin measurements of $PO_2$ are not adequate unless local hyperemia of the skin to facilitate oxygen diffusion is achieved. Peripheral skin measurements are also less sensitive to acute changes in blood gas concentrations. Peripheral skin measurements have so far proven reliable only in babies. In adults, the major difficulty relates to the thickness and permeability of the skin.

To summarize, there are five blood gas parameters which can be determined in three different media, (1) arterial blood, (2) tissue, and (3) peripheral skin. A ranking of the current clinical utility of these measurements would be arterial blood, tissue and peripheral skin a distant third.

Invasive Colorimetric Technologies

While the list of patents and papers describing colorimetric measurement techniques and applications is quite extensive, the application of such technology to the measurement of pH, $PCO_2$ and $PO_2$ is well summarized by the following paper and three patents.

U.S. Pat. No. 4,854,321 titled "Integrated Optical System for Monitoring Blood Gases" by A. A. Boiarski describes the use of colorimetric substances in dye wells. A colorimetric substance is a chemical which changes color in a quantifiable way when exposed to another given substance. Litmus paper (e.g. phenolphthalein solution) for measuring pH is a well known example. As stated in the Abstract, "Blood gases . . . are monitored by a single probe having multiple dye wells and dyes immobilized in the wells, the dyes being exposed to the blood gases. Optical fibers and waveguides connected to the dye wells permit light to be directed form a light source to the dyes and the light due to absorption or the spontaneous emission of the dye returned to a light detector. The intensity, phase shift or other mechanism of the returned radiation is a measure of the partial pressure of a respective blood gas." The technology requires that the probe containing the dye wells be in direct contact with the blood.

U.S. Pat. No. 4,682,985 titled "Fiber Optic Probe for Quantification of Colorimetric Reactions" by D. Costello is a similar technology with the additional feature of a probe which has an overall diameter "sufficiently small to permit the probe to be inserted into living tissue directly" (column 1, lines 12-17). "A colorimetric substance contained in the sample chamber changes colors in response to chemical properties of the chemical to be colorimetrically measured, thereby changing the amount of light transmitted through the sample chamber by the optical fibers." See the abstract of the patent. The patent describes the use of this technology for pH, $PCO_2$ and $PO_2$ determinations.

A similar technology to that disclosed by Boiarski and Costello is described for pH determination by S. R. Goldstein et al. in "A Miniature Fiber Optic pH Sensor For Physiological Use," Journal of Biomechanical Engineering, Vol. 102, 141-146. The article describes the concept of using two fiber optic strands to illuminate and remotely sense the color change of a dye indicator contained in a hollow fiber permeable to hydrogen ions.

Another colorimetric technology is described by Gehrich et al. in U.S. Pat. No. 4,989,606. The patent describes an invasive system for sampling small amounts of blood from a patient in a continuous manner. The blood is placed in contact with a "optical sensing element, for example sensing elements based on light fluorescence or absorbance." See column 4, lines 43-45.

Separation by semipermeable membranes.

The direct measurement of the partial pressure of a $PO_2$ and $PCO_2$ gas by absorption spectroscopy following separation by a semipermeable membrane is described in U.S. Pat. No. 4,201,222 to T. Hasse. The technology is based on the concept that gas can flow through a barrier until an equilibrium state is reached. If the barrier is made of a material permeable to selected gases then absorption spectroscopy can be used to quantify the amount of gas in the chamber, with the amount of gas present being proportional to the partial pressure of such gas. The specific method of measurement uses a single wavelength determination. Carbon dioxide is measured at approximately 2000 nm and oxygen is measured at 759 nm. Thus, the device described requires insertion into an arterial blood vessel and is not suitable for noninvasive measurements.

Electrode Devices/Sensors

The prior art associated with the measurement of $PCO_2$ and $PO_2$ by electrochemical sensors is extensive. A generalized description and overview of this technology can be found in P. Rolfe's article "Review of Chemical Sensors for Physiological Measurement." Biomedical Engineering Centre, University of Oxford, UK. Journal of Biomedical Engineering, 1988, April, 10(2), pages 138-45. The majority of blood gas and electrolyte analyzers used in hospital clinical chemistry laboratory use electrodes. The application of this technology to transcutaneous or noninvasive blood gas determination is most completely described in a series of patents assigned to Radiometer A/S of Denmark. U.S. Pat. Nos. 4,274,418; 4,324,256; and 4,685,465 describe the use of potentiometric and polarographic electrodes for "measurement of the blood gas partial pressures of oxygen and carbon dioxide," (Abstract of U.S. Pat. No. 4,685,465). It is important to note that electrodes measure parameters of the medium in direct contact with the probe. Thus, the partial pressures of oxygen and carbon dioxide measured by the transcutaneous electrodes would be that of the peripheral skin, not arterial blood.

A similar electrode based instrument is described by G. J. Ullrich et al. in U.S. Pat. No. 4,930,506. The technology varies from the Radiometer patents in that the Ullrich invention couples an electrode device with a standard pulse oximeter for continuous determination of peripheral skin $PCO_2$ and arterial blood oxygen saturation. $PCO_2$ is measured by immersion of a pH electrode in an electrolyte solution which is then placed in contact with the skin. Oxygen saturation is determined by use of two measured intensities at 650 and 805 nanometers. The algorithm for determination of the oxygen saturation using these two measured intensities is not specified.

In-Vivo pH Measurement Transistors

An area of sensors which has received significant attention over the past decade is the use of ion selective field effect transistors (ISFET). Specifically M. E. Meyerhoff et al., U.S. Pat. No. 4,694,834, B. Oeseburg et al. "Intravascular pH-ISFET, a method of the future," Scand. J. Clin. Lab Invest 1987 (47, Suppl. 188; 31–35), and P. Bergueld "The Development and Application of FET-based Biosensors," Biosensors 2 (1986) 15–33, describe the use of potentiometric ion selective electrodes based on semiconductor technology for the in-vivo continuous determination of pH. The technology is currently limited to pH determination and is invasive.

Semi-Invasive Techniques

A semi-invasive technology for the measurement of pH, $PCO_2$ and $PO_2$ is described by M. A. Fostick in U.S. Pat. No. 4,041,932. "Briefly, the technique of the present invention includes the formation of a skin 'window' in a small area of a patient by removal of substantially all of the stratum corneum (top dry layer of skin) in the area. Such a window is preferably less than one inch square. An enclosed chamber is positioned tightly against the skin around the window so formed and sealed thereto by sterile grease or adhesives such as the types commercially available for sealing other medical instrumentation elements to the human skin. The chamber and adjacent skin is heated to above normal skin temperature. Gases or fluids are collected in the chamber from the patient through the skin window for a time until equilibrium is reached. The internal portion of the chamber is an extension of the patient's body, at least insofar as the constituent of interest is concerned." See column 53, line 53-column 4, line 1. PH, $PCO_2$, and $PO_2$ are then measured by absorption spectroscopy via univariate methodology. Univariate analysis uses the ratio of two wavelengths, one to provide baseline information and a second frequency specific for the analyte of interest. Again, this technology determines certain blood gas parameters (i.e., pH, $PCO_2$ and $PO_2$) of peripheral skin, not arterial blood.

Optical or Spectroscopic Determinations

U.S. Pat. No. 4,509,522 by T. J. Manuccia describes the determination of $PCO_2$ and PCO; invasively in arterial blood, or non-invasively in tissue. The gas concentration is determined by a univariate linear algorithm. The method is described in column 2, lines 35–50 as follows: "For each molecule to be studied, two wavelengths must be transmitted through the blood sample. One wavelength must lie within an absorption band that is characteristic of the molecule (CO: ~5.13 um) while the other wavelength should be at a nearby wavelength in the IR that is not absorbed by the molecule. By normalizing the magnitude of the absorbed signal to that of the non-absorbed signal, the absolute concentration of the absorbing gas can be determined. Also in this way, the patient-to-patient variations in the optical properties of body tissue and skin are eliminated. The heart of the invention rests on the fact that the various blood gases absorb at discrete wavelengths in the infrared as opposed to their continuous and overlapping absorptions in the visible and near-IR." This last statement implies that the device of Manuccia, et al., would not work in a situation where there are overlapping absorptions. Although this methodology may work well for $CO_2$ and CO, it would not work well for determination of pH, $PO_2$, $[HCO_3^-]$ and $O_2$ saturation. The spectral regions used for determination of pH, $PCO_2$, and $[HCO_3^-]$ overlap extensively as is often the case in the near infrared. Thus, the univariate method described by Manuccia et al. is not applicable to the simultaneous noninvasive determination of all blood gas parameters.

The clinical utility of Manuccia's technology will be limited due to the frequencies used for the $PCO_2$ and PCO measurement. The frequencies specified by Manuccia (i.e. between 3.0 and 14.0 microns) are in the mid-infrared, an area of the spectral domain in which the light propagation characteristics are not consistent with transmission measurements through the finger, and typically the penetration of light is not to the arterial vasculature. Thus, measurements made will be similar to a peripheral skin determination. To summarize, Manuccia's technology can not measure all blood gas parameters, uses frequencies inconsistent with noninvasive tissue determination and employs an algorithm which will perform poorly in the near infrared frequency region.

Oximetry

The ability to determine arterial blood oxygen saturation in both pediatric and adult populations via oximetry is well known. Pulse oximetry is an accepted method of oxygen determination and has been utilized in clinical medicine for years. All pulse oximeters are based on several governing principles. First, the concentration of blood in a given location of the body varies with each pulse of the heart. With each heart beat a systolic pulse pressure is generated which leads to a maximal expansion (i.e. dilation) of the vascular system. During the resting period of the cardiac cycle (i.e., diastole) there is no pressure generated and the vascular system returns to a minimal size. This variation can be measured with optically based methods, by introducing a light source near the skin and detecting either the reflected or the transmitted light intensity. The light transmitted or reflected during diastole (i.e., the period when the arterial system is at its minimal size) interacts with the skin, fat, bone, muscle and blood. Light transmitted or reflected during systole, (i.e., the period of maximum expansion of the arterial system) interacts with the same skin, fat, bone, muscle, and blood, plus an additional amount of blood which is present due to the expansion of the arterial system. If the diastolic signal is subtracted from the systolic signal the result is a signal which represents the additional amount of blood. The subtraction process removes the interferences created by the interaction of the light with the skin, fat, bone and muscle. The quality and clarity of the subtraction generated signal is related to the amount of additional blood present which, in turn, is proportional to the pulse pressure, (i.e., the difference between systolic pressure and diastolic pressure). See FIG. 2 for a graphical representation of the above process.

All present pulse instruments assess variations in red blood cell concentration by utilizing a light frequency near or at the isobestic point, where optical measurement of pulsatile volume is made independent of oxygen saturation. An isobestic wavelength is one which changes only with blood concentration but does not change intensity with oxygen saturation. Consequently, such a wavelength (typically in the range of 800–850 nm) intentionally eliminates information about oxygen saturation and establishes a reference. A second wavelength in the red portion of the spectrum, which is sensitive to oxygen saturation, is detected by either a transmission or reflection sampling technique. By using the isobestic wavelength as a reference and by comparing its spectral intensity to the intensity of the second wavelength in the red portion of the spectrum, it is possible to determine the oxygen saturation of the arterial blood non-invasively.

Spectroscopic Determination of pH in Non-Biological Systems

Optical determination of pH in non-biological systems has been demonstrated by several investigators. Two representative articles are "Near-infrared Spectrometric Determination of Hydrogen Ion, Glucose and Human Serum Albumin in a Simulated Biological Matrix," by Drennen et al. and "Measurement of caustic and caustic brine solutions by spectroscopic detection of the hydrogen ion in the near-infrared region, 700–1150 nm", by M. K. Phelan, one of the co-authors of current application.

With specific reference to pH determination, Drennen et al. describe a process for quantitative spectroscopic measurement using smoothed second-derivative spectra with multivariate analysis by principle component regression (PCR). Nineteen different sample solutions, with pH values ranging from 4.5 to 9.25 were scanned from 1100 to 2500 nm. The pH variation in the sample set was achieved by addition of appropriate amounts of acid and base (i.e. HCl or NaOH). Although the paper does describe the quantitative spectroscopic determination of pH by multivariate analysis, the solutions were extremely simple with the pH being the sole source of variation. This is sharp contrast to determination of pH in blood or tissue which are extremely complex systems with multiple varying parameters, (i.e., the remaining four blood gas parameters). Also, the pH range measured by Drennen et al. is outside the range consistent with human survival and the frequency region used is not compatible with noninvasive transmission measurement. Specifically, frequencies greater than 1450 nm are strongly attenuated by water and transmission through a significant amount of tissue is not possible.

Phelan et al. demonstrated measurement of hydrogen ion concentration in caustic (sodium hydroxide) and caustic brine (sodium hydroxide and sodium chloride) solutions. These investigators used the frequency region from 700–1150 nm with subsequent analysis of the resulting spectra by multiple linear regression and partial least squares. As above, it's important to emphasize that the system studied is not biological, the pH variation is far outside that of normal physiology, and is not nearly as complex as found in biological systems.

Background on Spectral Analysis Algorithms

Optical measurements in whole blood following reactions with enzymes and/or reagents are commonly employed in the clinical chemistry laboratory. The use of spectroscopic techniques with multiple wavelengths for such a determination is much less common. Further, it is essential to realize that all prior noninvasive monitors, specifically Manuccia, et al., and the majority of prior art pulse oximeters used 3 or less measured intensities and one or two variables for analysis. Methods that simultaneously use two or more variables are known as multivariate methods. Thus, while Manuccia et al and the above described pulse oximeters do utilize optical measurement techniques, the algorithms used for analysis are not as powerful or sophisticated as those utilized herein.

A simple illustration of the increased capability of multivariate methods in component concentration determination is provided by FIGS. 3. In FIG. 3A one can see that an impurity component, whose spectrum overlaps that of the analyte, can affect the spectrum of the analytic band. Therefore, the accuracy of the analysis will suffer when the analysis is performed at a single wavelength $v_1$ or when rationing $v_1$ to a reference wavelength. The measured absorbance, $A_m$, at the analysis wavelength, $v_1$, for a sample containing the impurity is different than the true absorbance, $A_t$, of the analyte at that wavelength. If the calibration curve in FIG. 3B is from spectra of samples containing no impurity, then the presence of the impurity in the sample will yield an apparent concentration that may be quite different from the true concentration. This error will remain undetected if the intensity was measured at only one wavelength. If the impurity is included in the samples, a calibration plot similar to that in FIG. 3B will exhibit large scatter among the data, and the result will be both a poor calibration curve and concentration estimates that have poor precision for the unknown samples. However, with analysis at more than one wavelength, not only can the presence of the impurity be detected, FIG. 3C, but if its presence is included in the calibration, quantitative analysis of the analyte is possible with multivariate calibration methods, even if the impurity and its concentration are unknown.

An indication that the unknown is different from the set of calibration samples not containing the impurity is obtained by plotting the absorbance of the calibration samples and the unknown sample spectra at two frequencies selected for analysis. As exhibited in FIG. 3C, the spectrum of the sample containing the impurity (indicated by "x") is obviously different than that of the calibration spectra (i.e., it is an outlier). Outliers are those samples or spectra among either the calibration or unknown data that do not exhibit the characteristic relationship between composition and spectra of the other calibration samples. The sensitivity in detecting outliers is increased by increasing the number of frequencies included in the analysis. The number of independently varying impurities that can be simultaneously accounted for in the analysis is also increased by increasing the number of frequencies utilized.

Accurate univariate methods are dependent upon the ability to identify a unique, isolated band for each analyte. Multivariate methods can be used even when there is overlap of spectral information from various components over all measured spectral regions. Unlike univariate methods, multivariate techniques can achieve increased precision from redundant information on the spectra, can account for base-line variations, can more fully model nonlinearities, and can provide outlier detection.

The general approach that is used when statistical multivariate methods are applied to quantitative spectroscopy problems requires calibration in which a mathematical model is generated relating analyte concentrations to reference spectra. See FIG. 4. This calibration model can then be used for prediction of concentrations in unknown samples. The spectra of a series of calibration standards are first obtained, such that the spectra span the range of variation of all factors which can influence the spectra of future unknown samples. Assuming that the calibration uses samples that contain all the components expected in the unknown samples and spans their expected range of variation, the calibration will be able to empirically account for (or at least approximate) non-ideal behavior in Beer's law, independent of the source of the non-ideal behavior. Nonlinearities may arise from spectroscopic instrumentation, dispersion, or intermolecular interactions. As used in this application "nonlinear" refers to any deviation in Beer's law or the inverse Beer's law relationship (i.e., which cannot be modeled with the standard linear expression y=mx+b; where y represents the dependent variable, x is the independent variable, and m and b are, respectively, the slope and intercept).

Once the empirical calibration relating spectra and component concentrations has been performed, then the spectrum of the unknown sample can be analyzed by a multivariate prediction step to estimate the component concentrations or properties. If the calibration samples are truly representative of the unknown sample, then the result of the analysis will be an estimate of analyte concentration. In addition, spectral residuals (i.e., the difference between measured and estimated spectra) can be used to determine if the unknown sample spectrum is contained within the range spanned by the calibration samples. If the unknown sample is not representative of the calibration samples (i.e., is an outlier), spectroscopic interpretation of the residuals can often be made to determine the source of any differences between unknown and calibration samples. See Haaland, David M.: "Multivariate Calibration Methods Applied to Quantitative FT-IR Analysis" in Practical Fourier Transform Infrared Spectroscopy, Industrial and Laboratory Chemical Analysis, Edited by J. R. Ferraro and K. Krishman, *Academic Press, Inc.* 1990. Not only do multivariate statistical methods provide enhanced analysis of component concentrations, but such multivariate methods have also recently made possible the estimation of physical and chemical properties of materials from their spectra. Such multivariate statistical methods have been used in the analysis of salt water, peas, glucose, and thin-film dielectrics.

The use of multivariate analysis in noninvasive medical monitoring is best described in U.S. Pat. No. 4,975,581 to M. R. Robinson, K. J. Ward, R. P. Eaton and D. M. Haaland and current pending U.S. patent application Ser. No. 07/729, 452, titled "Oximeter for Reliable Clinical Determination of Blood Oxygen Saturation in a Fetus" by M. R. Robinson, D. M. Haaland and K. J. Ward. U.S. Pat. No. 4,975,581 discloses a method and apparatus for, particularly, quantitatively determining the amount of glucose in a human.

Co-pending patent application Ser. No. 07/729,452 describes a fetal oximeter which is designed to:

A. Overcome the limitations of prior art oximeters, including their inability to obtain information at a variety of wavelengths simultaneously, and the limitation inherent in the time necessary for the intermittently energized light sources in such prior art oximeters to reach the required brightness and stability.

B. Utilize multiple frequencies with simultaneous sampling, employ an algorithm which can signal average over the recorded frequencies and model nonlinearities over the entire clinically observed blood oxygen saturation range and which is suitable for noninvasive measurements in the fetal environment.

C. Determine if a sample's spectrum and subsequently determined oxygen saturation value (from either the calibration set or the fetus being monitored) is representative of the calibration samples.

This last object is crucial for the implementation of an accurate and reliable clinical fetal monitor. Identifying and removing outlier samples from the calibration set can drastically improve the accuracy and precision of the subsequent predictions. Identification of outliers among the unknown samples provides information for evaluating the validity of the fetal blood oxygen saturation determination. This ability is especially important in this medical application because the consequences of hypoxia on the fetus can result in death or lifelong disability.

A number of multivariate calibration methods are available for quantitative spectral analyses. Many of these have been reviewed by D. M. Haaland, supra. These include PLS, PCR, CLS, MLR, Q-matrix, Kalman filtering, and cross-correlation. In addition, ridge regression, continuum regression, and neural networks are other possible multivariate methods that can be used in quantitative spectral analysis.

Multivariate methods which are well suited for analysis of blood gas parameter spectroscopic data are those that model the spectra using an inverse Beer's law model, such as principal component regression (PCR) or partial least squares (PLS). An advantage of this multivariate approach is that the nonlinearities in the spectral response to changes in composition can be accommodated without the need for an explicit model. PLS and PCR methods are capable of achieving accurate and precise results in the presence of linear and nonlinear dependencies in the absorbance spectrum at various frequencies. Thus, an entire spectral region can sometimes be used in multivariate analysis without the requirement that the spectroscopist choose an optimal set of wavelengths for the analysis. Similarly, these methods of computation are not sensitive to linear dependencies introduced by over sampling of information at many frequencies in the construction of the calibration samples. See Cahn, et al., "Multivariate Calibration of Infrared Spectra for Quantitative Analysis Using Designed Experiments". *Applied Spectroscopy* 1988 Vol. 42 No. 5 p. 865.

Continuum regression comprises an infinite-member family of methods for multivariate calibration. PLS and PCR are individual members of the continuum regression family. See, M. Stone, and R. J. Brooks (1990), "Continuum Regression: Cross-validated Sequentially Constructed Prediction Embracing Ordinary Least Squares, Partial Least Squares and Principal Components Regression," Journal of the Royal Statistical Society B., 52, pp. 237–269.

Two or more analytes can be calibrated or analyzed simultaneously by using a global PLS method called PLS2. In practice PLS2 tends to underperform PLS1 (analytes calibrated sequentially) primarily because model complexity is fixed for all analytes. Also, it is difficult to come up with a necessary metric that combines calibration errors across wildly different analytes, which is akin to adding apples and oranges. See, Lindberg W. Pesson, J. A. Wold, S. (1983), Analytical Chemistry, 55, p. 643.

Ridge regression is another multivariate calibration method which has been used in non-medical situations in which the intensities at different spectral frequencies exhibit significant collinearity and the number of calibration samples exceeds the number of spectral frequencies. Martens and Naes, "Multivariate Calibration," John Wiley: Chichester, (1989), showed that ridge regression is mathematically similar to PCR, but cannot be described explicitly by data compression. Hoerl et al., Practical use of ridge regression: a challenge met, "Applied Statistics" 34, 114–120, (1985), showed that ridge regression was a viable competitor to multiple linear regression in the context of predicting percent protein in wheat samples by using reflectance in the near infrared region. Naes et al., Comparison of lineal statistical methods for calibration of NIR instruments, "Applied Statistics" 35, 195–206, (1985), concluded that ridge regression is a viable competitor to PLS and PCR when the number of spectral frequencies approaches the number of calibration samples.

Another type of multivariate algorithm gaining wide acceptance is a pattern recognition technique using what are called neural networks. Weights are applied to the inputs, which determines the signal strength. The sum of the inputs at that neuron determines the strength of the neuron. The weighted sum is transformed with a linear or nonlinear transfer function, the most popular transform being the sigmoid function. This transfer function determines the output of the signal, depending on the gain that is set. All neurons are interconnected, but pass data only one way, as the brain does. The output signal can be transferred to several different neurons, each of which has its own weight. The network "learns" the weights of the output signal at each neuron, optimizing the weights to achieve the "correct responses" (i.e. the reference calibration values). Like other multivariate calibration methods, neural networks learn from the input they are given. They have the potential advantage that they can explicitly model nonlinearities. However, they also tend to be more susceptible to overfitting, and slower to compute, and are more difficult to interpret than PLS, PCR, and MLR.

The applicants recognize that both the preferred embodiment of U.S. Pat. No. 4,975,581 and co-pending application Ser. No. 07/729,452 utilize the partial least square algorithm (PLS). However, the reasons for utilizing PLS and the other multivariate algorithms in the invention disclosed and claimed herein is quite different from the reasons it was utilized in the above described patent and application. For noninvasive glucose determination, the limiting factor in measurement is the lack of information available. The determination of a blood analyte, such as glucose, requires a very high signal-to-noise ratio and a sophisticated algorithm for extraction of a minuscule amount of information (glucose is, normally, 0.1 weight percent of blood). In the case of a pulse oximeter suitable for fetal monitoring, the information is abundant (i.e., babies that are profoundly hypoxic are blue), but the environment of operation is extreme. The reflected light-oxygen saturation relationship is highly nonlinear, the signal for analysis is extremely noisy and interfering background components must be removed by correlating with the pulsating blood.

In contrast to the foregoing, the rationale for using multivariate analysis in the present application of noninvasive blood gas determination is to enable accurate determination of blood gas parameters where the information content in the spectral domain overlaps and where the infrared patterns for pH, $PCO_2$, $PO_2$ and $[HCO_3^-]$ are small or do not exist in the absence of interactions with water and other blood or tissue components. Examination of FIG. 10 shows that the regions of spectral information for the various components overlap extensively. This is especially true for pH which does not exhibit a strong correlation in any specific region. The problem of differentiating bicarbonate from carbon dioxide is also difficult as evidenced by their similar correlation curves.

The use of visible and infrared spectroscopy for the noninvasive determination of blood gas parameters is not obvious. In fact "at first glance, the determination of pH by infrared spectroscopy is so implausible as to seen ridiculous." "Salinity determination using NIRH," T. Hirschfeld, *Applied Spectroscopy*, Volume 39, Number 4, 1985. Not only does water have exceptionally strong absorption bands, but H+ and $O_2$ sat. have no absorption bands of their own in the near infrared.

Infrared spectroscopy obtains quantitative and qualitative information from the vibrational motion in molecules. Each type of chemical bond in a molecule will absorb different frequencies of infrared energy, giving rise to the characteristic patterns seen in an infrared spectrum. These patterns, called absorption bands, change in magnitude with concentration. Traditional methods of quantitative spectroscopy correlate band height or the area of a band to the concentration of the species under study. In the present application of infrared spectroscopy, characteristic infrared patterns for each species under study (pH, $O_2$, $CO_2$, $[HCO_3^-]$) are small or do not exist when not interacting with other components. However, these species do have an effect on species that do absorb, specifically hemoglobin and water. Hydrogen ion, being an ion rather than a molecule, does not have infrared bands. However, hydrogen ions will bind to other species in solution that are infrared active, thus a correlation for pH can be based on secondary spectroscopic effects. Oxygen, although a molecular species, does not have infrared bands. However, it will also interact with other species that are infrared active and produce a change in the spectra. In particular, oxygen reacts with hemoglobin, producing a marked change in the infrared spectra of hemoglobin between 600 and 1000 nm. This reaction is nonlinear, however, and quantitative models must account for this nonlinearity. For $CO_2$, and $[HCO_3^-]$, near infrared spectral absorbances are small. $CO_2$ can be quantitated easily in the mid-infrared region. $[HCO_3^-]$ also has bands in the mid infrared region. But in the near infrared region, $CO_2$ and $[HCO_3^-]$ absorbance are small compared to the much larger effect of hemoglobin and proteins. Again, secondary effects must be studied. Thus, accurate measurement of the various blood gas parameters is difficult due to the small absorbances and/or secondary effects resulting from concentration changes. These differences necessitate the use of multivariate analysis.

The clinical utility of pulse oximetry is well established. The clinical utility of a noninvasive blood gas monitor, (for the simultaneous determination of pH, $PCO_2$, $PO_2$, $[HCO_3^-]$ and $O_2$ saturation) is clearly desirable and the technology for realization of such a monitor as well as data utilizing the technology is disclosed herein. Continuous monitoring and real time (i.e., analysis of the data as it is acquired) is desired, as it would enable the physician to identify peaks, troughs and trends as they are occurring in the patient. Such monitoring would be of significant benefit when a patient's cardiopulmonary status is changing rapidly.

It is an object of the present invention to provide an instrument which will represent a remarkable improvement in blood gas monitoring technology by:

A. Providing noninvasive blood gas monitoring which can determine all blood gas parameters in arterial blood and/or tissue.

B. Providing continuous determination of all blood gases in real time; and

C. Having the ability to provide the physician with a measure of validity or assurance of accuracy by employing outlier detection methods.

The ability to determine inaccurate results is extremely important, especially when caring for the critically ill patient.

It is an object of the present invention to determine the blood gas parameters in either human tissue. In the case of tissue determination, the light will interact with tissue in both the dermis and epidermis. If the light is transmitted through, for instance, the finger, the optical determination will measure the blood gases of all the components that are irradiated by the light. Total tissue blood gas determination is not currently used in clinical medical practice due to lack of availability of such information. However, total tissue determination may be a better measure than arterial blood gas measurement because the physician is interested in knowing how well the tissue is being perfused by the patient's cardiopulmonary system. If the tissue in an extremity is being well perfused then the physician could reasonably assume that more vital and internal organs were also being perfused at an adequate rate, (i.e. liver, kidney, spleen and brain).

It is an additional object of the present invention to determine blood gas parameters in arterial blood. The method of sampling during the systolic and diastolic portions of the cardiac cycle enables determination of the pulse blood spectra. This spectra can be subsequently analyzed by multivariate algorithms for determination of blood gas parameters. Thus, the present invention enables measurement of blood gas parameters in arterial blood noninvasively.

In the case of the present invention, it is an object to use wavelengths in the 500-2400 nm range to determine arterial blood gas parameters. As several components are determined, measured intensities at several wavelengths will be required. Each parameter to be measured often requires at least one measured intensity for determination and each spectroscopically interfering substance will also usually require measurement of an intensity for compensation of its interference. Thus, determination of multiple components may require measurement of three or more wavelengths.

An additional advantage of the methodology of the present invention is the ability to report all blood gas parameters. The various parameters can be measured directly or calculated from well established equations. The relationship between pH, $PCO_2$, and $[HCO_3^-]$ is described by the Henderson-Hasselbach equation:

$$pH = 6.1 + \log \frac{[HCO_3^-]}{0.03 * PCO_2}$$

The Henderson-Hasselbach equation allows for determination of two components with calculation of the third.

Additionally $PO_2$ can be calculated from $O_2$ sat. and vice versa. O'Riordan et al. compared various calculation algorithms and assessed their accuracy relative to normal human data. See, J. F. O'Riordan, T. K. Goldstick, L. N. Vida, G. R. Honig, and J. T. Ernest, "Modelling whole blood oxygen equilibrium; comparison of nine different models fitted to normal human data", Advances in Experimental Medicine, Vol 191, pp 505-522, 1985. The concurrent use of pH in these calculations to more accurately assess the $P_{50}$ value may improve overall calculation results.

SUMMARY OF THE INVENTION

This invention relates to methods and apparatus for, preferably, determining non-invasively and in-vivo at least two of the five blood gas parameters (i.e., pH, $PO_2$, $PCO_2$, $[HCO_3^-]$ and $O_2$ sat.) in a human.

The preferred method includes the steps of:

a. generating two or more different wavelengths of light, wherein the wavelengths are in the range of 500 nm to 2,400 nm;

b. irradiating in vivo and non-invasively blood containing tissue with such wavelengths, so that there is differential attenuation of at least some intensities of the wavelengths by the blood containing tissue as a function of the wavelengths, the differential attenuation causing intensity variations of those wavelengths incident from the blood containing tissue as a function of those wavelengths, the tissue and the unknown levels of pH, $[HCO_3^-]$, $PO_2$ and $O_2$ sat.;

c. measuring said intensity variations from the blood containing tissue to obtain a set of intensity variations v. wavelengths;

d. generating at least one calibration model which is a function of conventionally measured blood gas parameters obtained from a set of calibration samples and intensity variations v. wavelengths data obtained from irradiating such set of calibration samples with the same 2 or more different wavelengths of light; and e. calculating the values of the unknown blood gas parameters in the blood containing tissue from the measured intensity variations from the tissue utilizing at least one algorithm and the calibration model, the calculating using 2 or more variables.

The method and apparatus: (1) provide for the detection of both spectral and contractration outliers in both the blood containing tissue and the calibration set; (2) provide for the determination of the blood gas parameters in both tissue and arterial blood; (3) utilize one or more algorithms, at least one of which is a multivariate algorithm such as PLS, PLR and neural networks; (4) includes the pretreatment of data; (5) utilizes a calibration model for each parameter being determined; and (6) can be used with both reflected and transmitted light.

The apparatus includes, for instance, a spectrometer apparatus for conducting light to and from the patient, an array detector, a computing unit, and a visual display module.

The method and apparatus can also be used invasively.

DESCRIPTION OF THE PREFERRED EMBODIMENT

Figure 1:
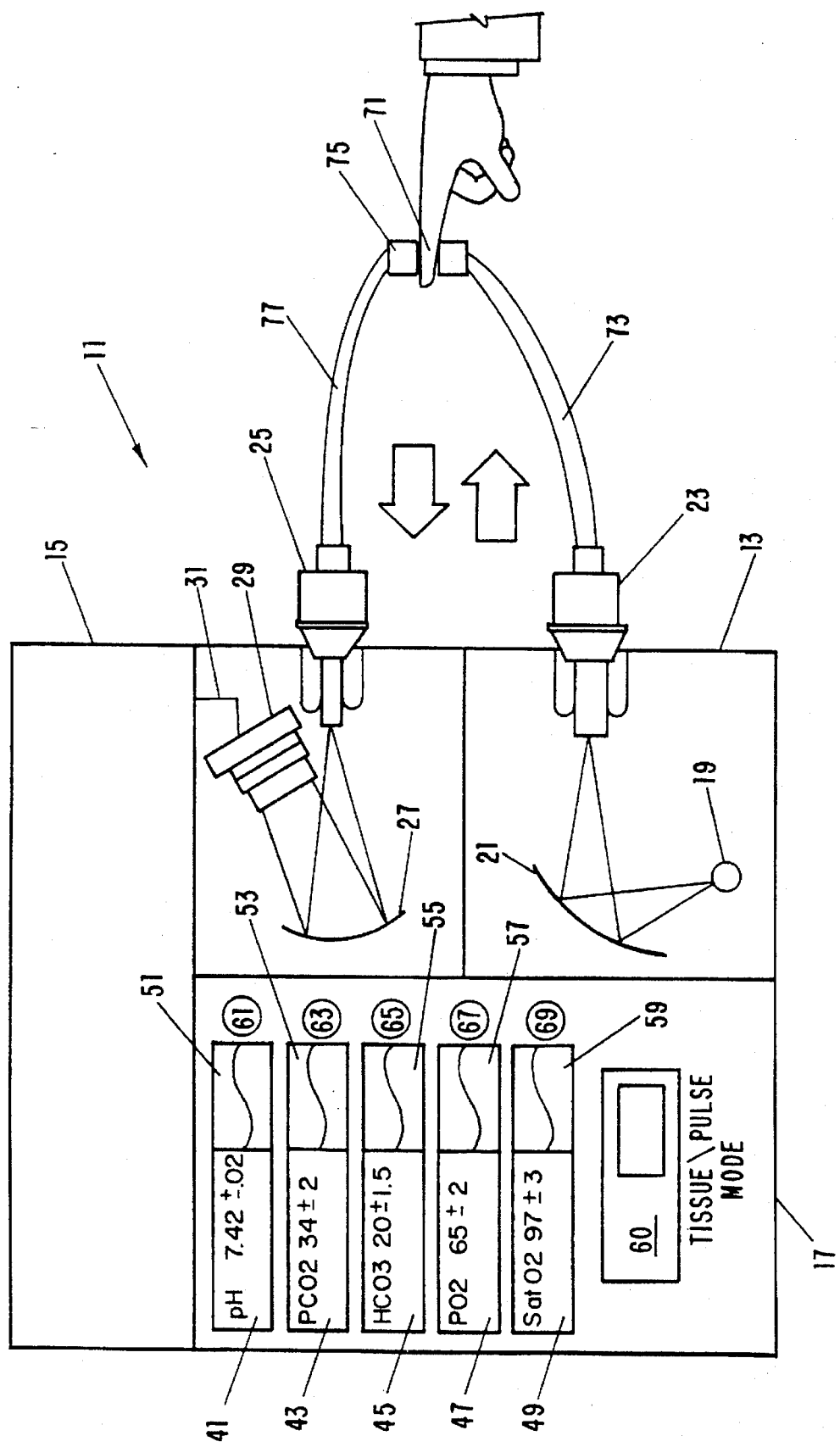
FIG. 1 is a schematic illustration of the preferred embodiment of the invention.
Figure 2:
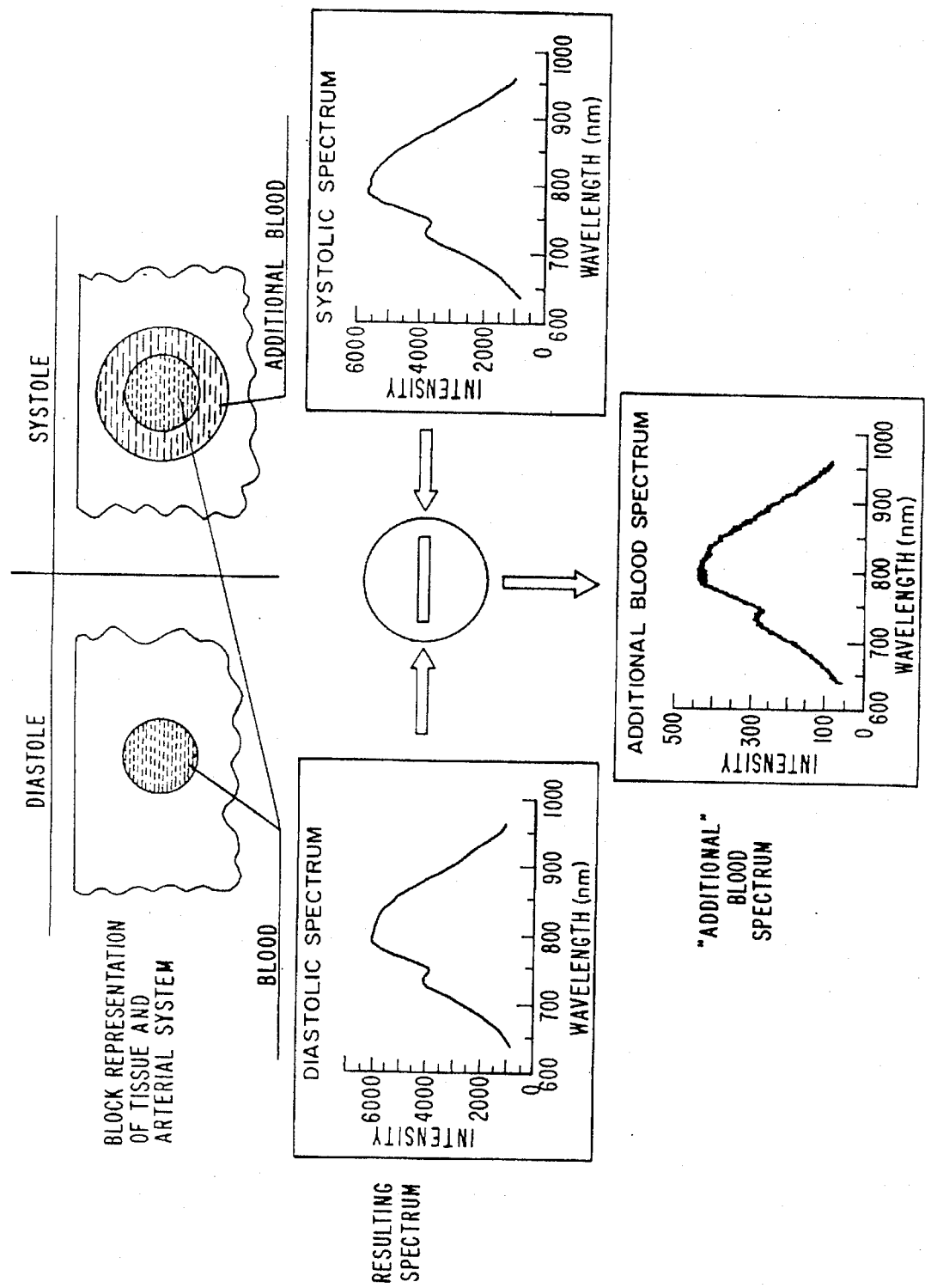
FIG. 2 is a graphical representation of the basic principle of how additional blood spectra can be determined.
Figure 3A:
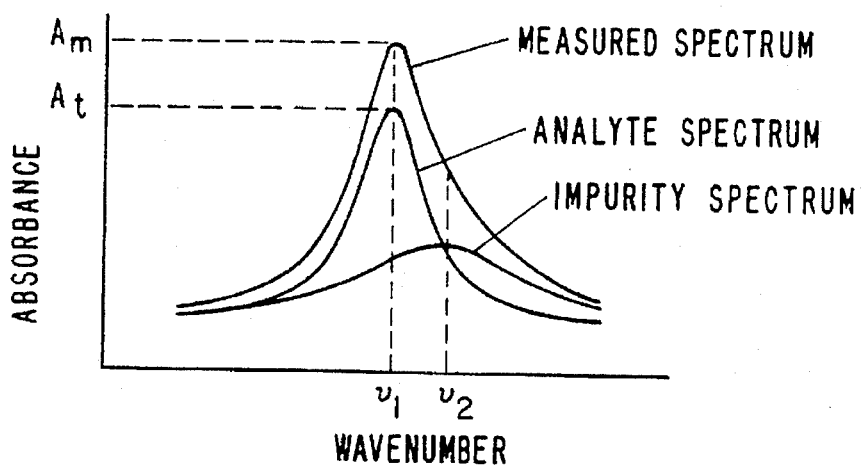
FIGS. 3A-3C are a series of graphs comparing univariate calibration to multivariate calibration.
Figure 3B:
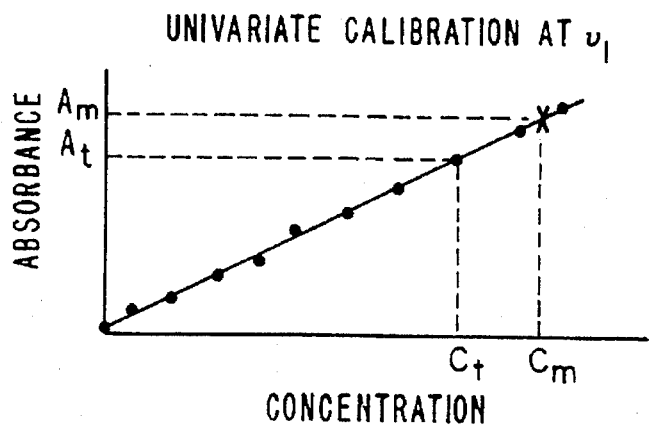
Figure 3C:
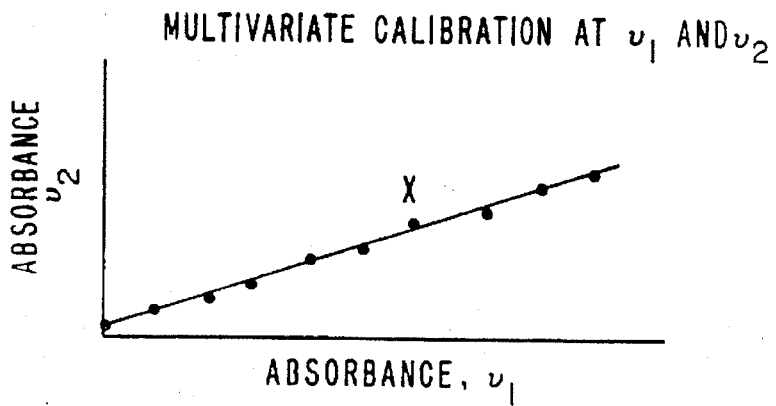
Figure 4:
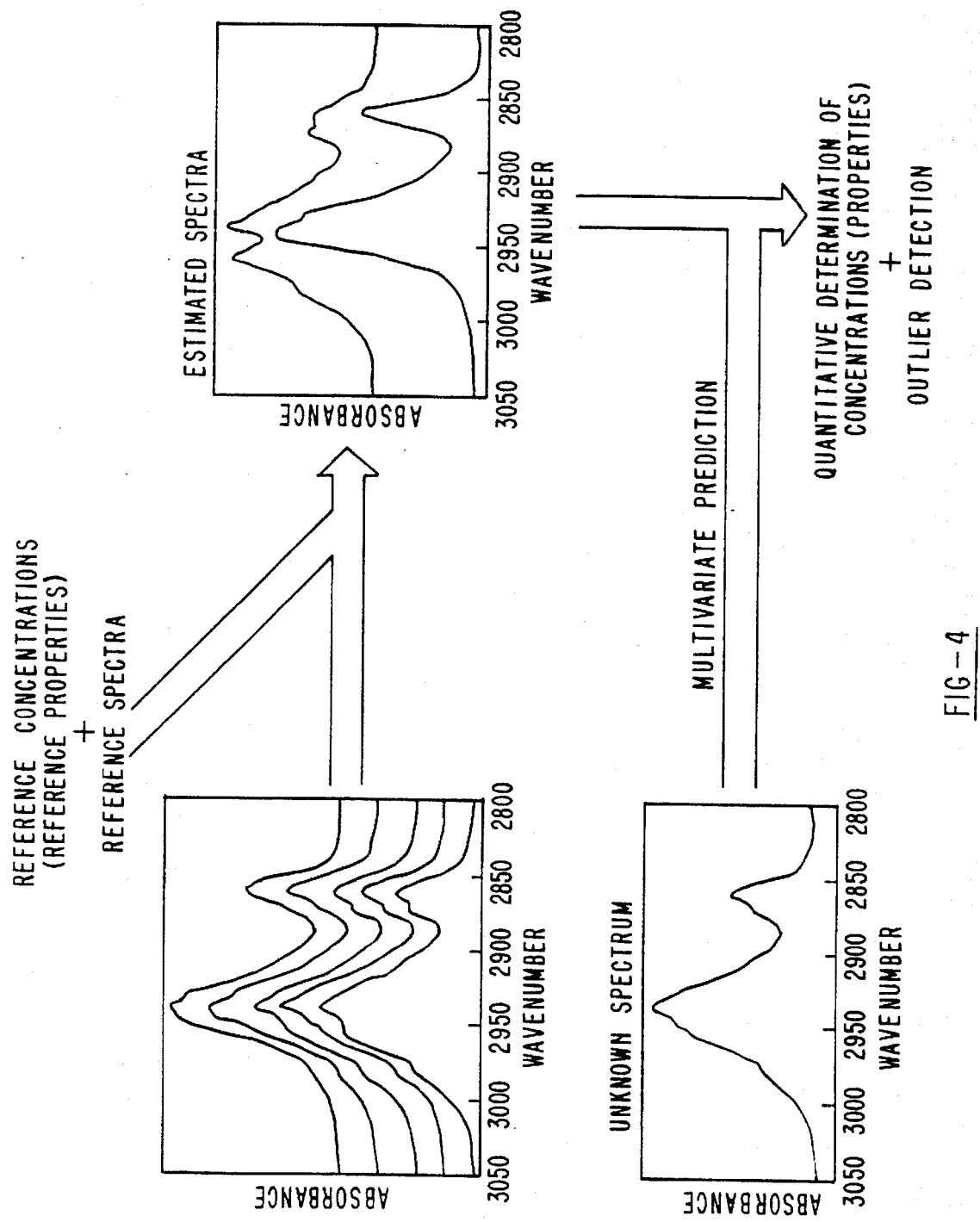
FIG. 4 is a chart showing the general approach used in multivariate statistical methods to generate a mathematical calibration model and to use this model to quantitatively determine concentrations and/or properties from the spectra of unknown samples.

With reference to FIG. 1, the preferred noninvasive blood gas monitor 11 of the present invention includes a spectrometer 13, an electronics and computer processing module 15, and a visual display module 17. Spectrometer 13 includes a broad band tungsten halogen light source 19, a focusing mirror 21, a fiber optic interface 23, a second fiber optic interface 25, a grating 27, an array detector 29, and an electronic buss 31. Module 15 includes a computing unit which, in turn, contains a microprocessor, memory, the data preprocessing algorithms, the multivariate calibration model, the multivariate algorithm and outlier detection algorithms. Visual display module 17 includes a pH display 41, a partial pressure of carbon dioxide display 43, a bicarbonate display 45, a partial pressure of oxygen display 47, and an oxygen saturation display 49. As illustrated, each of these displays includes each determination and the estimated uncertainty of such determination. Also included in module 17 are a pH trend display 51, a partial pressure of carbon dioxide trend display 53, a bicarbonate trend display 57, a partial pressure of oxygen trend display 57, and a oxygen saturation trend display 59. Visual display 17 also includes a tissue/pulse mode switch 60, which permits the doctor or other operator to change the mode of instrument operation from the tissue mode to the blood pulse mode, or vice-versa. Finally, display module 17 includes lights 61, 63, 65, 67 and 69 to indicate if the associated blood gas parameter which has just been determined is an outlier (e.g., light 61 is energized when the pH determination is an outlier).

To transmit light from spectrometer 13 to the fingertip 71 of the patient being monitored, monitor 11 includes a source fiber optic bundle 73, which terminates at finger/fiber device 75. Receiving fiber optic 77 returns the light from finger/fiber holder 75 to fiber optic interface 25. Finger/fiber holder 75 allows transmission through finger 71 and allows for adequate holding of the finger.

In operation, source 19 emits selected frequencies from approximately 500 to 2400 nm. This light is focused on the end of fiber optic 73 held in interface 23 via focusing mirror 21 and then transmitted via source fiber 73 to illuminate the tissue, bone, nail and blood in fingertip 71. The portion of the light which is transmitted through fingertip 71 is then returned to spectrometer 13 by fiber bundle 77. The returning light is then separated into various wavelengths and detected by the array detector 29, capable of detecting at least some of the wavelengths of light between 500 to 2400 nm.

The reflected light intensities at the various frequencies are then analyzed by the microprocessor of module 15 employing, a multivariate algorithm (such as PLS or PCR) utilizing several wavelengths from various regions of the entire spectral range of the transmitted light. Instrument 11 can be operated in two different modes: (1) the tissue determination mode; or (2) the pulse blood mode. In the tissue determination mode of operation the spectral data from array detector 29 is preprocessed by appropriate algorithms in module 15. Such preprocessing to include trimming, averaging, scaling, normalization and derivatization as necessary. The resulting processed spectrum is then analyzed by the algorithm contained in module 15. In the preferred embodiment the algorithm employed is partial least squares (PLS). Such an algorithm can either quantify directly from the spectral data or through use of other equations calculate all blood gas parameters. Only two of the following (pH, $PCO_2$ and $[HCO_3^-]$ need to be optically measured; with calculation of the third by the Henderson-Hasselbach equation.

Instrument 11 will display the current values of pH, $PCO_2$, $[HCO_3^-]$, $PO_2$ and $O_2$ sat., their estimated uncertainties, as well as the past history of each parameter in displays 51, 53, 55, 57 and 59. The spectral data analyzed and the current determinations will be examined by outlier detection algorithms contained in the computing unit in module 15. If the spectra from the patient or the resulting determinations are abnormal then the instrument will indicate that the accuracy of those particular determinations are poor through the corresponding outlier lights, 61–69. A condition which might result in a spurious result might occur if the patient's fingertip were only partially inserted in the finger/fiber device 75. Other possibilities include the instrument being out of calibration, extreme blood gas values not included in the calibration model, or new and unique blood chemistries.

In blood pulse mode, spectra are acquired throughout the cardiac cycle of the patient. The resulting spectral data are analyzed to establish which spectra correspond with maximum concentration of blood (or maximum dilation) in the arterial system of the patient, and which spectra correspond with minimum concentration (or minimum dilation) of the arterial system. The spectra associated with minimum dilation will contain information regarding blood, skin, bone, and tissue. The spectra associated with maximum dilation will contain the same information plus an additional amount of blood information. To determine optical pulse pressure, the spectral difference at the isobestic frequency is calculated. Absorbance by wavelengths in the region from 800 to 810 nm are not strongly influenced by changes in oxygen saturation and are proportional to the amount of hemoglobin present. Thus, a plot of the average value between 800–810 nm will show the variation in hemoglobin concentration. The magnitude of this difference will correspond to the spectral difference between the systolic and diastolic pulses. This spectral difference is, in turn, a general measure of the quality of the spectral data. Those spectra having an abnormal optical pulse pressure are trimmed (i.e., removed) prior to further analysis. The trim process removes spectra which deviate significantly from the norm due to motion of the patient or other artifacts. As some of these artifacts will influence the spectra in an adverse manner, the removal of these spectra is important for production of an accurate pulse monitor. Additional preprocessing of the data may be required due to specific operating conditions. The calculation of the "additional" blood spectrum can be performed by several methodologies, including subtraction of the appropriately transformed spectral data from the maximum and minimum dilation. The above process effectively removes the interfering background and provides the multivariate algorithm with a spectrum corresponding to the additional blood. The resulting additional blood or pulse blood spectra may be subsequently averaged with existing scans to improve the signal-to-noise ratio of the spectrum to be analyzed. The resulting spectrum is then analyzed by the multivariate algorithm contained module 15. In the preferred embodiment the algorithm employed would be partial least squares or neural networks. The algorithm will either measure directly or calculate all blood gas parameters. The instrument will display the current value of pH, $PCO_2$, $[HCO_3^-]$, $PO_2$ and $O_2$ sat., their uncertainties as well as the past history of each such parameter as explained above with regard to the tissue mode. The accuracy of each of these determinations will also be assessed through the use of outlier detection methods contained in the computing unit in module 15.

Figure 6:
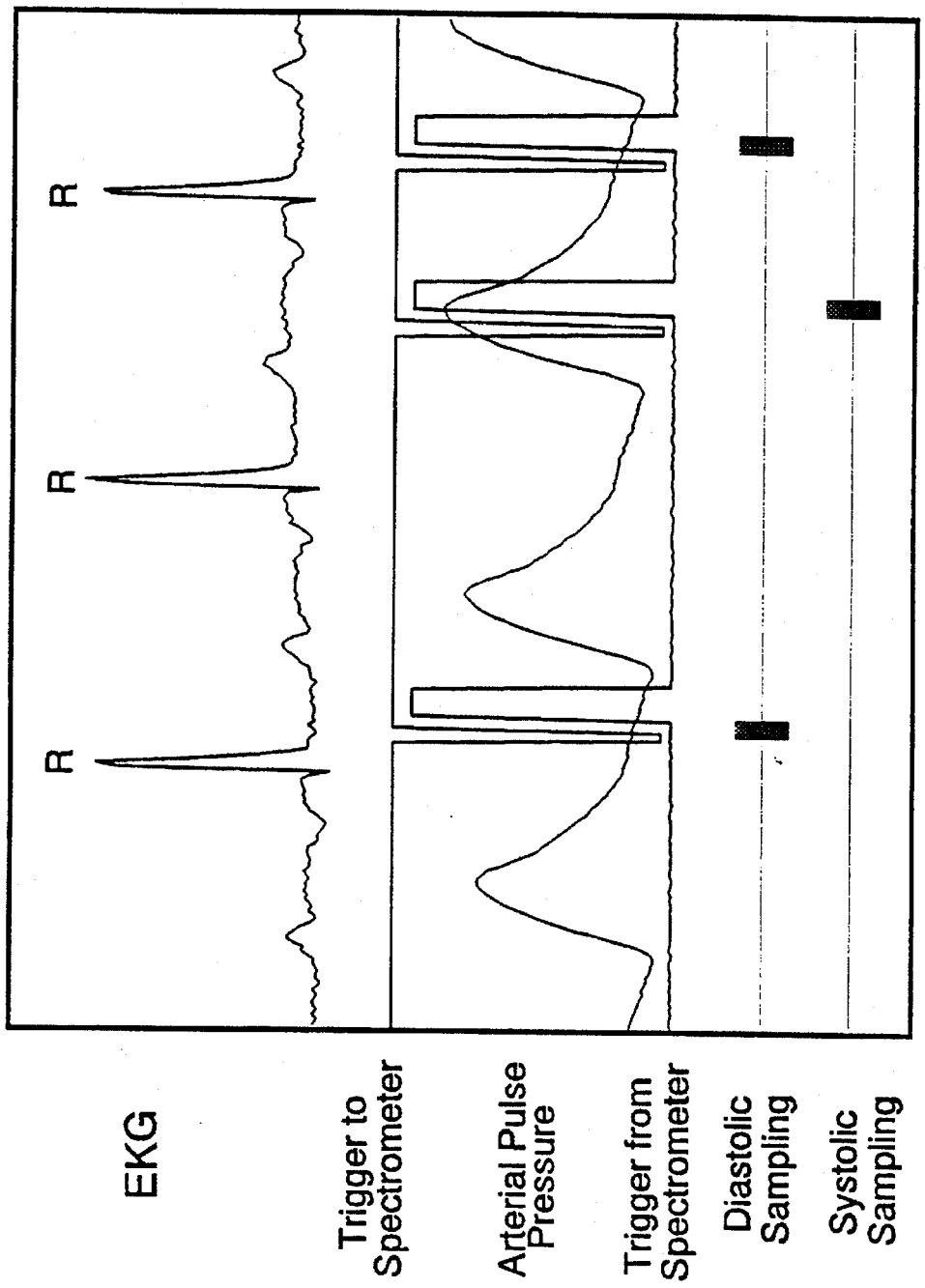
FIG. 6 is a graph of the electrical activity of the heart, the arterial pulse pressure, and the sampling period and corresponding electrical triggers.

An additional embodiment of the invention includes apparatus (not shown) for obtaining information regarding the electrical activity of the patient's heart, which can provide information to assist in determination of maximal and minimal arterial dilation. Typically most patients in intensive care units will have an EKG monitor in operation and use of this early accessible information will assist in the operation of instrument 11 in the pulse mode. With reference to FIG. 6, maximum expansion of the arterial system due to ventricular contraction occurs at a set interval following the R peak of the QRS complex. The QRS complex is created by the depolarization of the ventricular muscle. This complex precedes ventricular contraction which results in ejection of blood from the heart. Minimum expansion of the arterial system is present prior to ventricular contraction and corresponds to a time period in the vicinity of the P-wave. The P-wave results from depolarization of the atrial muscle. The time of minimum expansion is related to both the R peak of the QRS complex and heart rate. Correlation with the electrical activity of the heart may be desired for simplification in the processing of the spectral data and may be necessary for effective operation during period of decreased pulse pressure or excessive finger movement. To summarize, the electrical activity of the patient's heart provides additional information for improved operation, especially under adverse conditions.

It is the authors' experience that pretreatment of the spectral or concentration data often times improves the analysis precision in the calibration set and unknown analyses, as well as increases the robustness of the multivariate calibration models. Thus, data pretreatments including but not limited to centering, scaling, normalizing, taking first or higher order derivatives, smoothing, Fourier transforming, and/or linearization can all improve the analysis precision and accuracy. Additionally, trimming of those spectra differing from the norm for any reason can improve overall instrument performance. Such trimming techniques are not limited to assessment of the optical pulse. Other techniques include the comparison of the summation of the area under the curve, comparison of individual spectra with the average spectra, comparison of the Fourier transform, examination of the characteristic modes of vibration in the spectra, and comparison of principle component regression factors. These various techniques may be used individually or together for effective trimming. These pretreatments can also improve the robustness of the model to instrument drift and can improve the transfer of the calibration model between instruments.

To demonstrate the technical feasibility of the invention, noninvasive determination of both tissue and arterial blood gas parameters were performed on baby lambs under a variety of physiological conditions. The object of the investigation was to induce all reasonable acid-base disturbances in the lambs to show that the above described technology could noninvasively determine the blood gas parameters.

Specifically, the acid-base balance of the lambs was manipulated so as to induce respiratory acidosis, respiratory alkalosis, metabolic acidosis and metabolic alkalosis.

Figure 5:
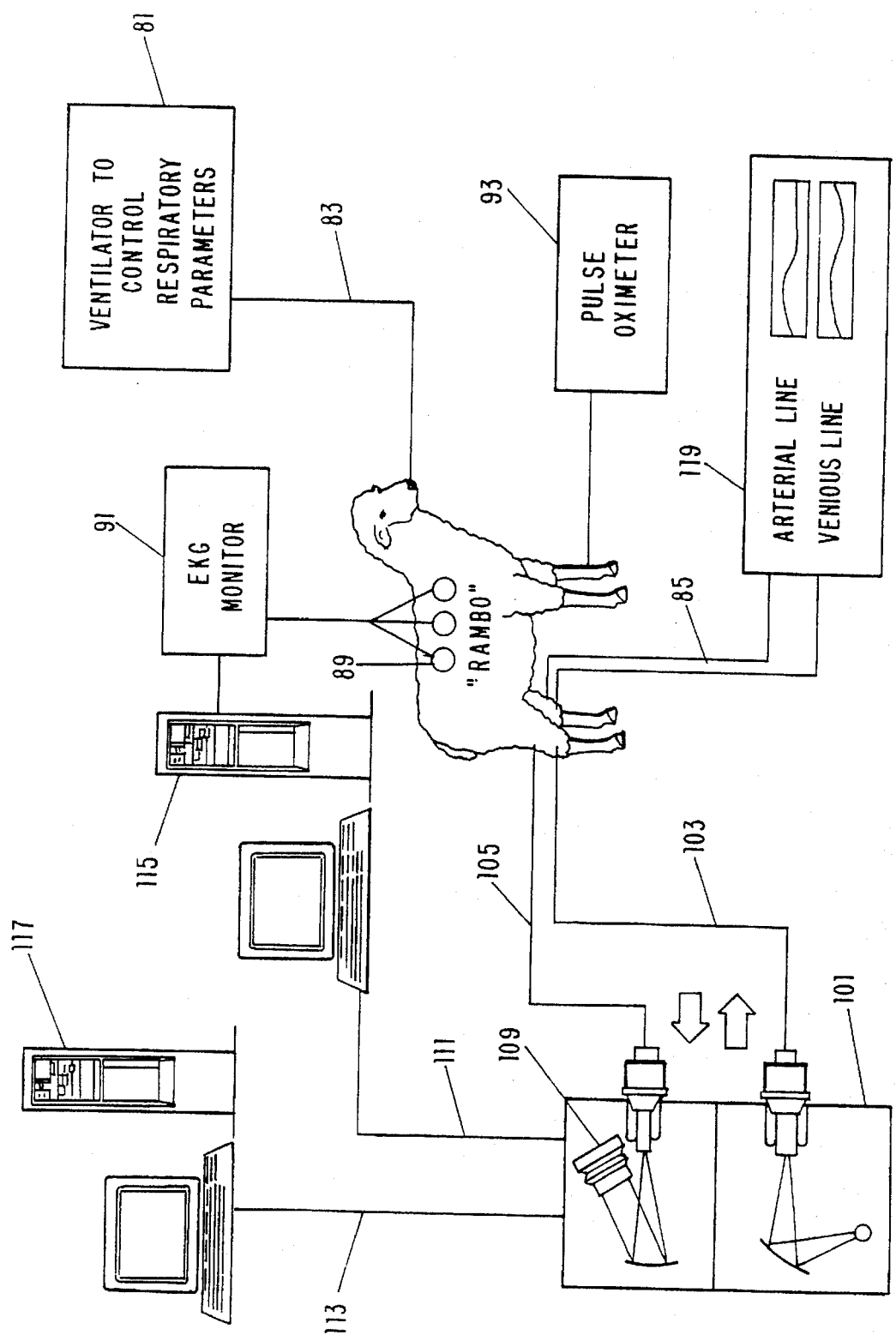
FIG. 5 is a schematic of the test apparatus used in the sheep studies.

New born lambs (age 10–25 days) were instrumented in accordance with approved animal research protocols, as schematically illustrated in FIG. 5. The animal's respiration was controlled following anesthetization by a conventional mechanical ventilator 81 with endotracheal intubation 83. Metabolic physiology was controlled by administration of bicarbonate or lactic acid as appropriate through a catheter 85. Cardiac physiology was monitored by placement of arterial and venous transducer/monitor and external placement of standard EKG electrodes 89 connected to EKG monitor 91. Oxygen saturation was monitored by use of a standard pulse oximeter 93. The femoral artery was used for arterial blood sampling and pulse pressure measurement.

After intubation and instrumentation of the lamb as set forth above, a spectrometer 101 equipped with a source fiber 103 and a receiving fiber 105 was applied to the lamb for procurement of spectral data. The exit end of source fiber 103 was positioned on one side of and in contact with the lamb's shaved leg, with receiving fiber 105 positioned on and in contact with the opposite side of the leg. Light from a tungsten halogen light source 107, covering the frequency range 500–1000 nm, was coupled to fiber 103 and transmitted to the lamb's leg. The light exits fiber 103 and enters the lamb's tissue where it interacts with all components of the lamb's (e.g., blood, interstitial fluid, muscle, bone, fat and skin), before exiting from the opposite side of the leg. At this point some of this light enters the receiving fiber optic. The light entering into receiving fiber 105 is returned to spectrometer 101 where it is separated by wavelength by using a holographic grating and subsequently detected on a silicon array detector 109. The light intensities at detector 109 is then converted to digital numbers and stored in computer 117.

During the lamb study, spectra, EKG information, and the arterial pulse were all acquired simultaneously. Computer 115 is used to process EKG signals from monitor 91 and subsequently to trigger spectrometer 101, via trigger line 111. Computer 117 is used to record spectral data from spectrometer 101 via electronic buss 113. The spectral data were acquired in two different modes: (1) pulse gated; and (2) EKG lock. In the pulse gated mode the spectral data was acquired at the same point in the cardiac cycle. Specifically, the shutter (not shown) to silicon array detector 109 was opened with detection of the R wave of the QRS complex of the EKG signal. Detector 109 was exposed to the light transmitted through the lambs leg for 50 msec, after which the shutter was closed. The spectral data was taken in this manner so the same or approximately the same amount of blood was present in the tissue during the spectral acquisition period. The data sampled in this manner is subsequently referred to as "pulse gated data". The light detected in pulse gated mode has interacted with the tissue as explained above and contains information from the cube of tissue through which it passed. The pulse gated data was then subsequently analyzed by several algorithms to predict arterial blood gas parameters.

The second mode of spectral acquisition is referred to as EKG lock. The concept is to use the electrical activity of the heart to determine the correct time to obtain systolic and diastolic spectra. The time separation between two consecutive R waves of the QRS complex was determined and the heart rate subsequently calculated. Spectral acquisition corresponding to the diastolic portion of the cardiac cycle occurred at a fixed time interval of 30 msec after the R wave. The systolic spectral sampling occurred at 50% of the cardiac cycle. If the heart rate is 120 beats per minute the total duration of the cardiac cycle is 0.5 seconds. Thus, the systolic spectrum would be sampled at 0.50×0.5 seconds (250 m sec.) after the R wave. The resulting spectral data is stored on computer disk as previously described.

Generation of Non-Physiological Acid-Base Conditions

The acid-base status of the lamb was varied over the maximum range reasonable. As previously stated pH, $PCO_2$ and $[HCO_3^-]$ are interrelated, as demonstrated by the Henderson-Hasselbach equation. Acid-base disturbances are classified first by the pH, which indicates an acidic or alkalotic state. The disturbance is further classified as a metabolic or respiratory disturbance. The magnitude of the disturbance in either $PCO_2$ or $[HCO_3^-]$ determines if the abnormality is respiratory or metabolic.

To introduce respiratory perturbations the partial pressure of carbon dioxide in the lamb's blood was manipulated by changing the rate of mechanical ventilator, particularly the minute ventilation to the lamb. The minute ventilation is the total amount of air given to the animal over one minute. Decreasing minute ventilation leads to retention of carbon dioxide and a corresponding respiratory acidosis. Increasing minute ventilation has the opposite response, leading to alkalosis and a decrease in the arterial partial pressure of carbon dioxide. Reasonable physiological limits for carbon dioxide are 20 to 60 mm Hg.

To introduce metabolic perturbations the lamb was given intravenous bicarbonate or lactic acid. The accumulation of bicarbonate results in a metabolic alkalosis, while lactic acid results in an acidosis. Reasonable physiological limits for bicarbonate are between 15 and 40 mmol\L. Additionally, perturbations in pH were limited to 7.2 and 7.6.

To examine the ability of the instrumentation to determine both $O_2$ sat. and $PO_2$, the fraction of inspired oxygen ($FiO_2$) was varied randomly over the course of the tests. The animal's $O_2$ sat. was varied from 80 to 100% while the partial pressure of oxygen varied from 45 to 115 mmHg. $O_2$ sat. and $PO_2$ are related quantities, but are not related in a linear fashion. The relationship between $PO_2$ and $O_2$ saturation has been well characterized as a sigmoidal curve. (Biochemistry, Lubert Stryer, W. H. Freeman and Company, 1975). Thus, both parameters were correlated over the course of the tests.

The arterial blood samples from the lambs were measured on a Mallinckrodt Sensor System Gem-Stat blood gas/electrolyte analyzer. The Gem-Stat is a commonly used bedside blood gas monitor and is a clinically accepted method for blood gas determination.

The accuracy and precision of the reference values used in this study were assessed by analyzing summary data provided by Zaloga et al. (1989) Zaloga et al. used a single Gem-Stat instrument to obtain estimates of blood pH, $PO_2$ and $PCO_2$ from 166 patients. Based on this study we conclude that the Gem-Stat is inherently accurate with respect to these blood measurements. That is, values of pH, $PO_2$ and $PCO_2$ reported by the Gem-Stat, are centered around, and are not systematically high or low when compared to the corresponding values obtained from the clinical laboratory. It follows that $[HCO_3^-]$ determinations reported by the Gem-Stat are also inherently accurate. The precision of the Gem-Stat describes how scattered the GemStat measurements are about the values obtained from the clinical laboratory. In the study reported by Zaloga et al., the precision of the Gem-Stat measurements was affected by the basic repeatability of the measurements (for a fixed patient)

and patient-to-patient variation (reproducability). A metric of precision is the standard deviation. Roughly speaking, two-thirds of the Gem-Stat values are within one standard deviation of the corresponding clinical values. Based on Zaloga et al., our estimates of the analyte-specific standard deviation are as follows:

pH—0.025
$PO_2$—10 to 20 mm (10 at 50 mm $PO_2$ and 20 at 120 nm $PO_2$)
$PCO_2$—3 mm
$[HCO_3^-]$—2 millimoles per liter The accuracy of the measured $O_2$ saturation, performed on a Radiometer, OSM2, was difficult to assess due to lack of information available from the manufacturer. "Today, there is no universally adopted reference method for oxygen saturation measurements and Radiometer, [the manufacturer of the instrument used] has chosen not to establish its own reference method," OSM2 Hemoximeter reference manual. Thus, no information is available on the accuracy of the measurement. Radiometer did perform some tests to evaluate the precision of the instrument at only points, 0% and 100% saturation. Both points are outside the normal physiological limits so the utility of these measurements is limited. Nevertheless, the standard deviation of repeated measurements at 0% saturation is 0.2% and at 100% is 0.1%. The author's experience with the Hemoximeter suggests that the actual standard deviation of repeated measurements is approximately 2%.

Figure 7:
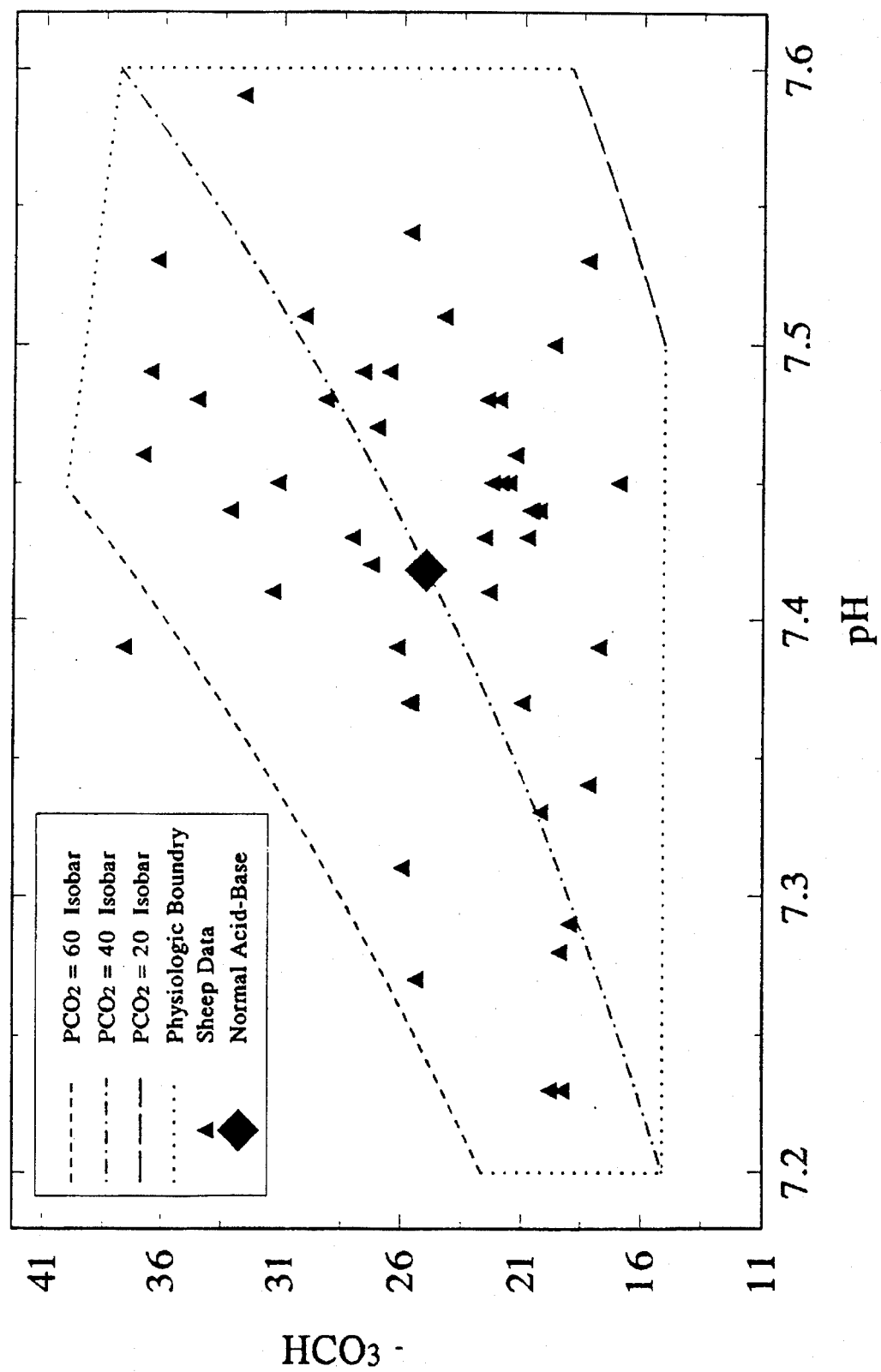
FIG. 7 is a graph illustrating the distribution of $[HCO_3^-]$ and pH determinations obtained with tests utilizing the apparatus illustrated in FIG. 5.
Figure 8:
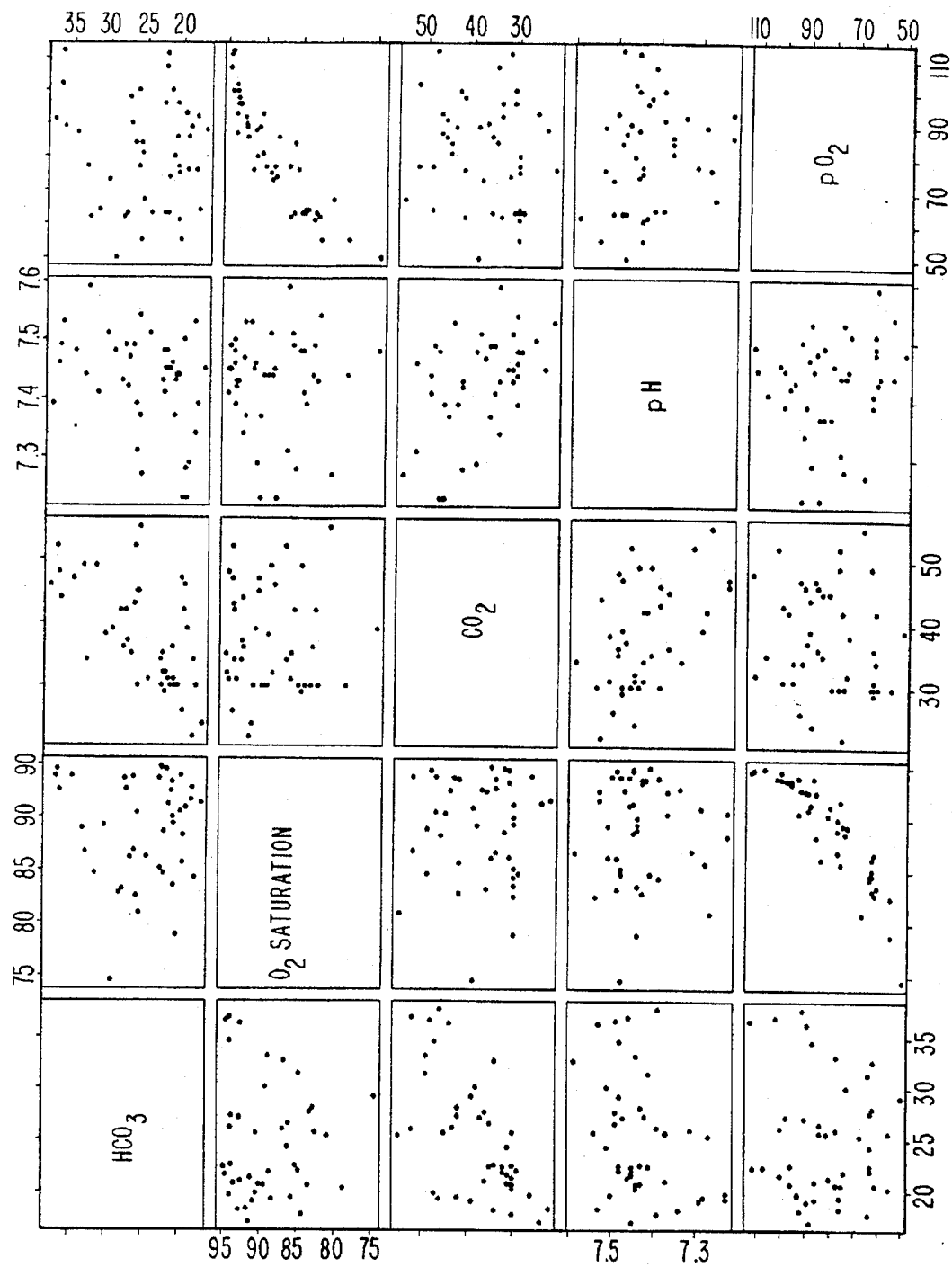
FIG. 8 is a scatterplot matrix illustrating the relationships between reference $[HCO_3^-]$, $O_2$ sat., $PCO_2$, pH and $PO_2$ obtained during the sheep studies.

FIG. 7 shows reasonable physiological boundaries for pH, bicarbonate, and carbon dioxide. One of the objects of the lamb study was to map out the entire physiological region, of respiratory acidosis and alkalosis as well as metabolic acidosis and alkalosis. Examination of FIG. 7 shows the acid-base balance of the lamb was disturbed over the entire physiologically reasonable space. Scatter plot, FIG. 8, shows the variation in oxygen saturation and partial pressure of oxygen over the course of the study. As pH, $PCO_2$ and $[HCO_3^-]$ are all constrained by the Henderson-Hasselbach equation, it is essential to make sure that the variation in one variable does not correlate completely with the variation in another variable.

FIG. 8 is a scatterplot matrix showing the relationship between all blood gas parameters. Examination of the figure shows that $PO_2$ and $O_2$ sat. are correlated as one would expect. However, there does not appear to be significant correlation between pH, $PCO_2$ and $[HCO_3^-]$. This lack of correlation demonstrates that each parameter (other than $O_2$ sat. and $PO_2$) was varying independently.

Analysis of Spectral Data in Simulated Tissue Mode.

Figure 9:
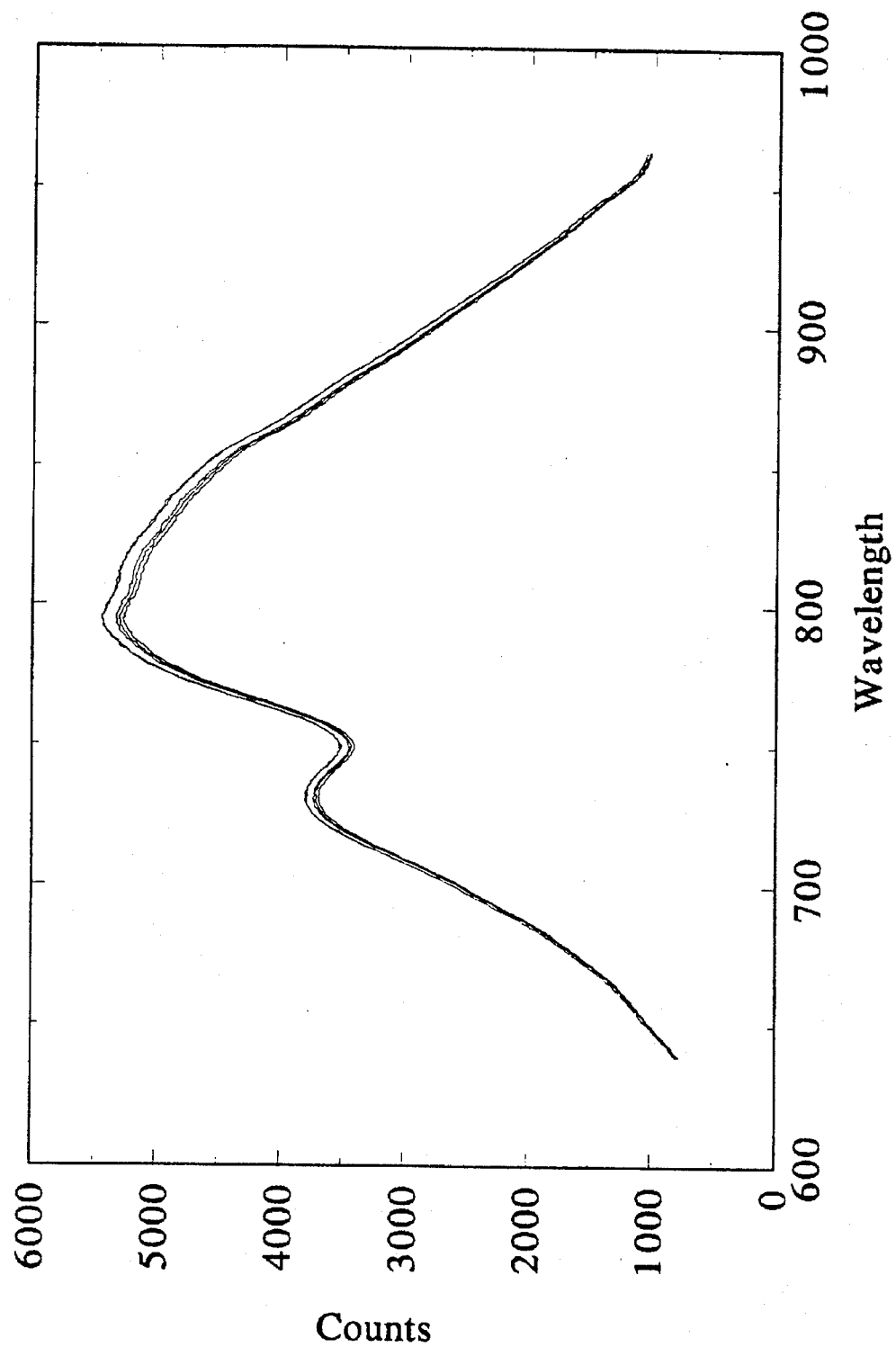
FIG. 9 displays tissue spectra from several representative samples.

The pulse gated data was acquired as stated above through the lamb's leg. Thirty scans were taken and subsequently averaged to form a single spectrum for each sample or observation point. Several representative spectra are plotted in FIG. 9. These raw intensity data were subsequently processed and analyzed in several ways.

Figure 10:
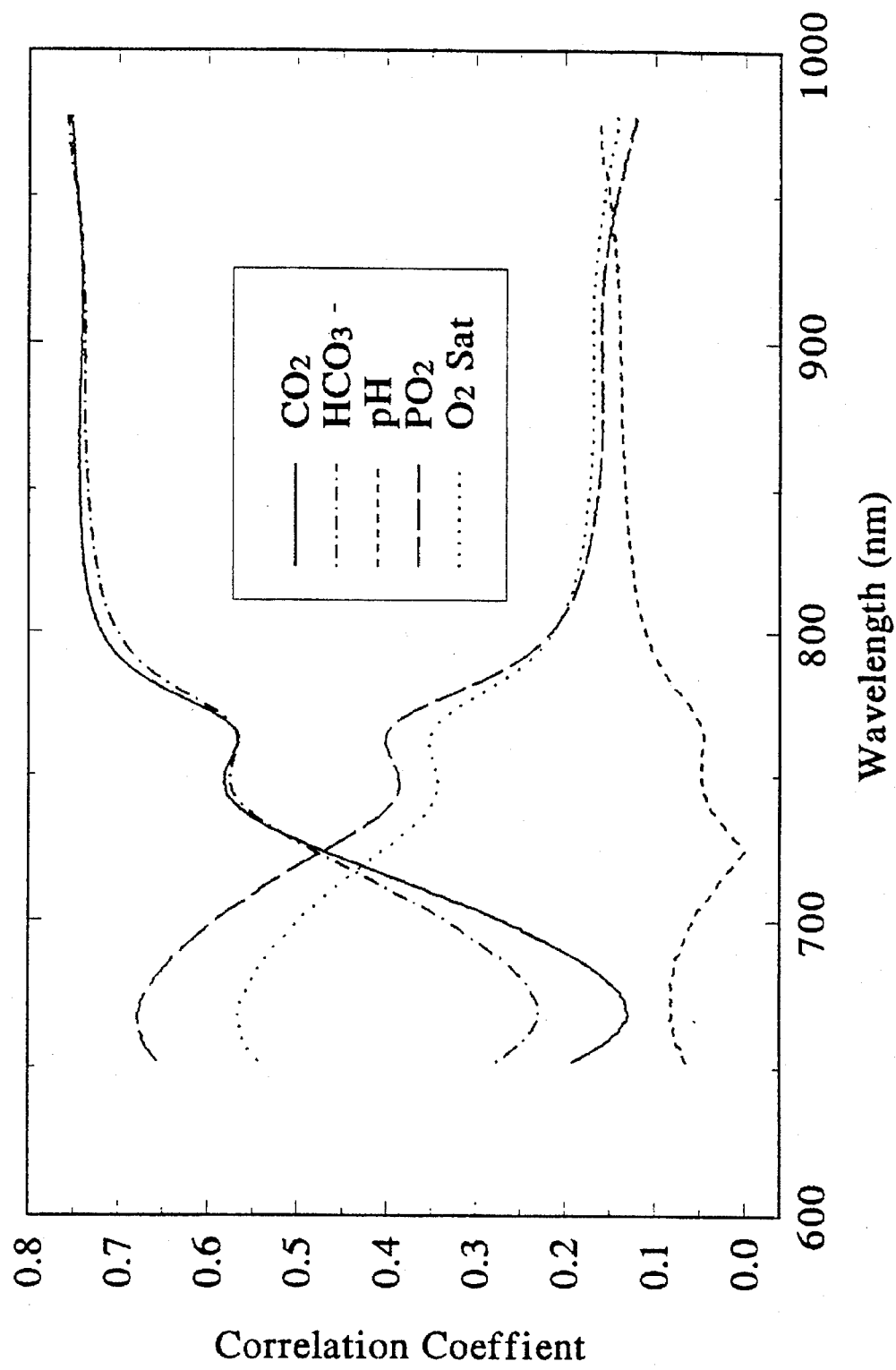
FIG. 10 is a graph illustrating the relationship between the absolute value of the correlation coefficient and wavelength for each of the five blood gas parameters.
Figure 11:
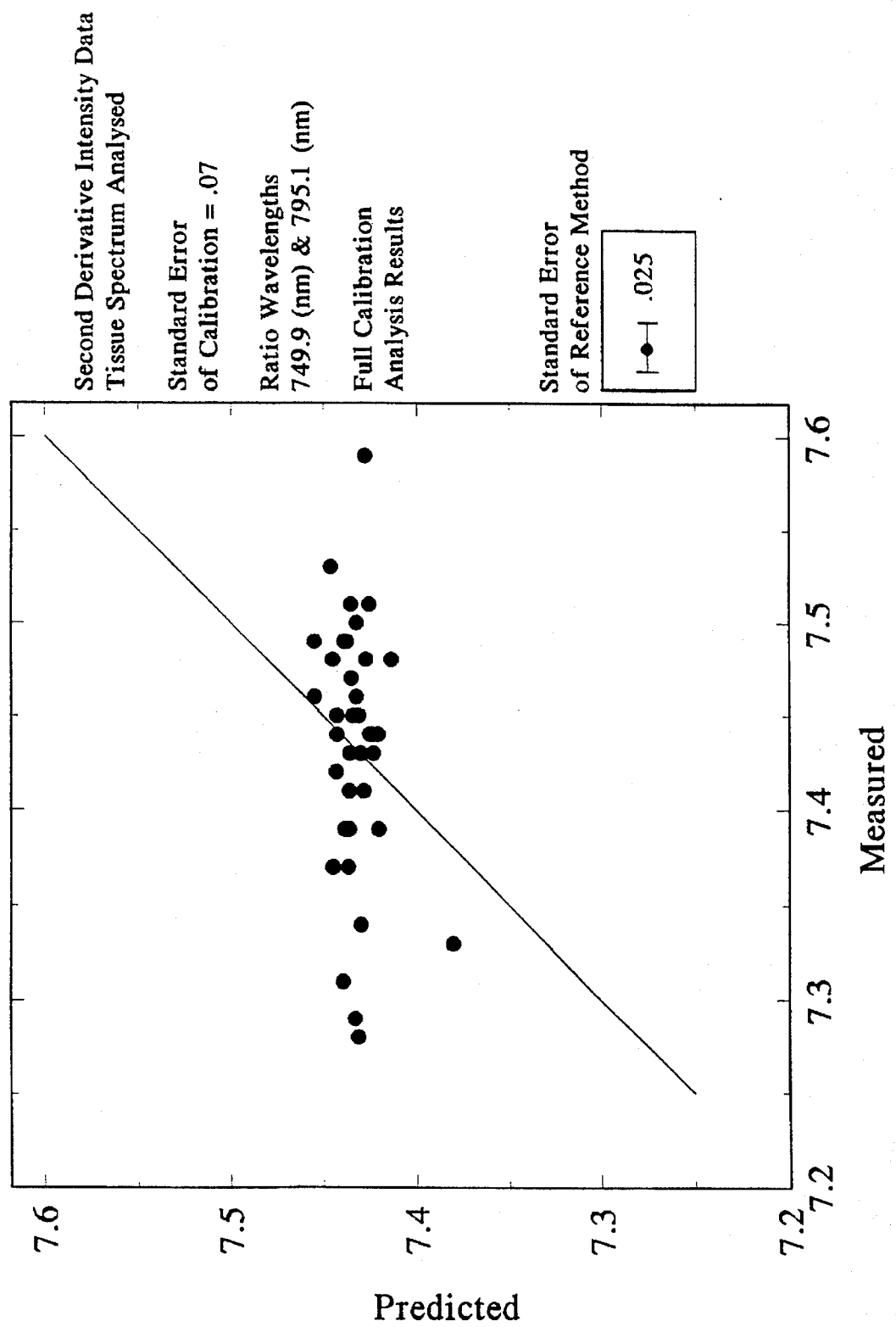
FIG. 11 is a plot of predicted tissue pH (obtained from the tests utilizing the test apparatus illustrated in FIG. 7) vs. measured arterial blood pH using the best ratio algorithm.
Figure 12:
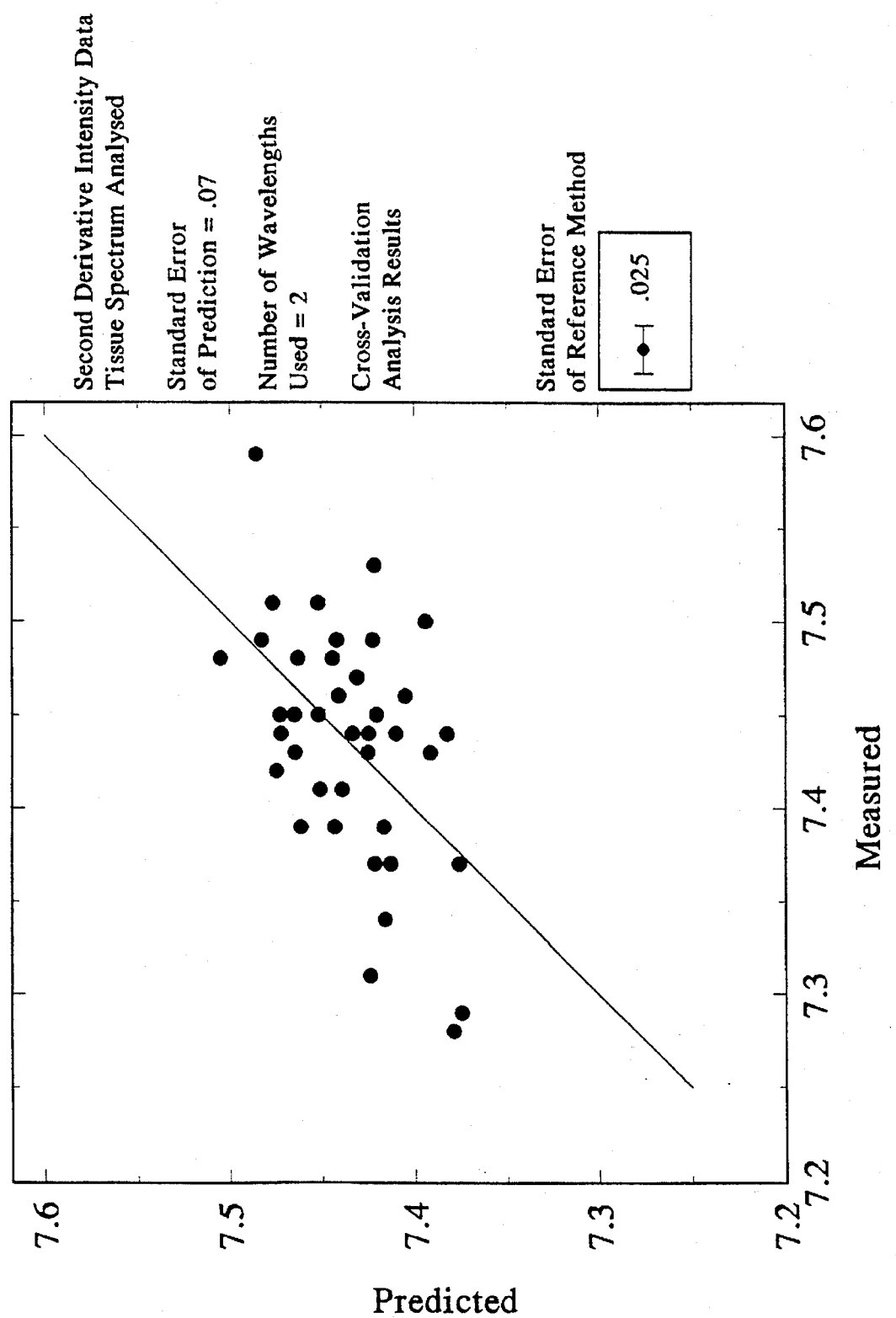
FIG. 12 is a plot of predicated tissue pH vs. measured arterial blood pH utilizing MLR.
Figure 13:
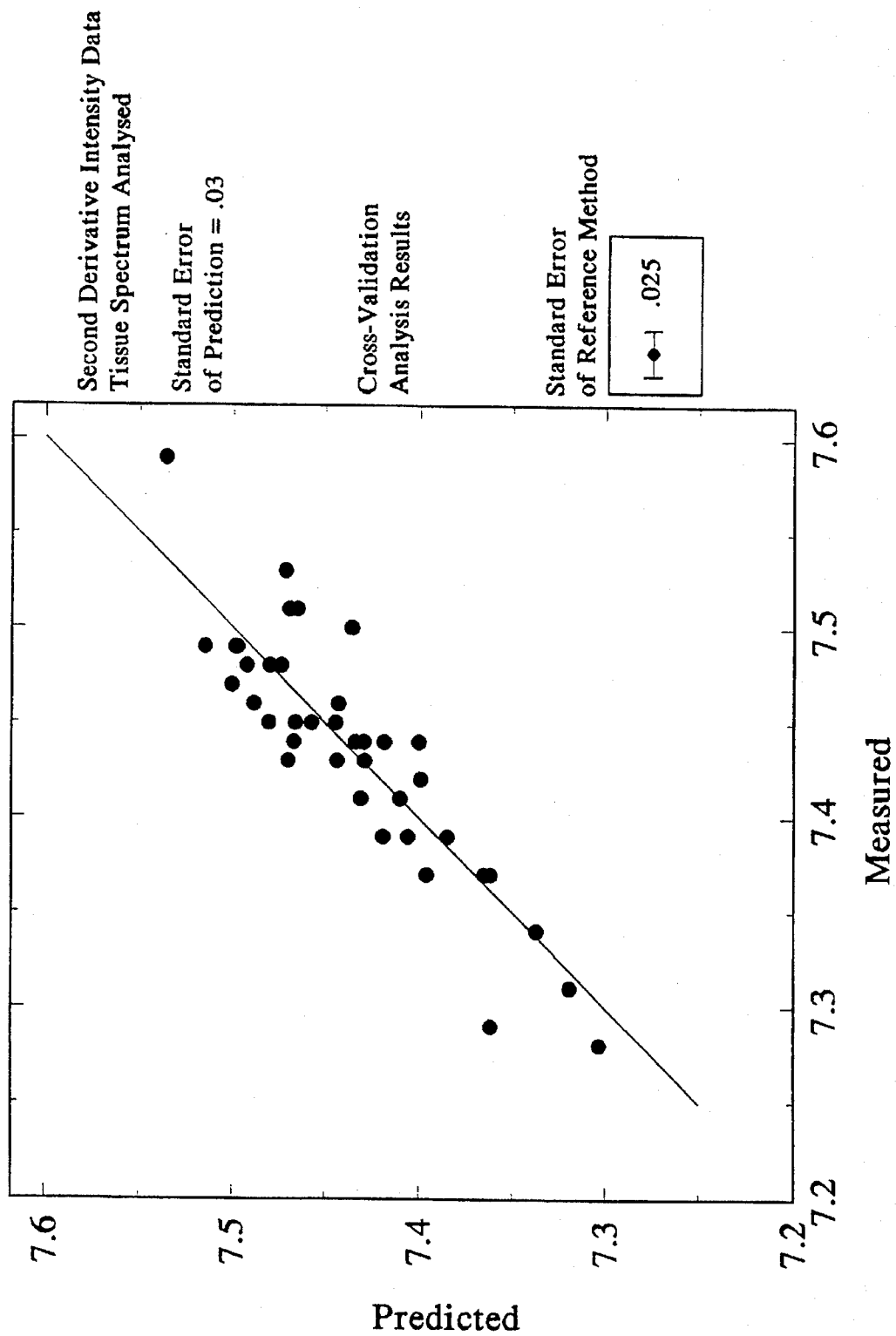
FIG. 13 is a plot of predicted tissue pH vs. measured arterial blood pH utilizing PLS.
Figure 14:
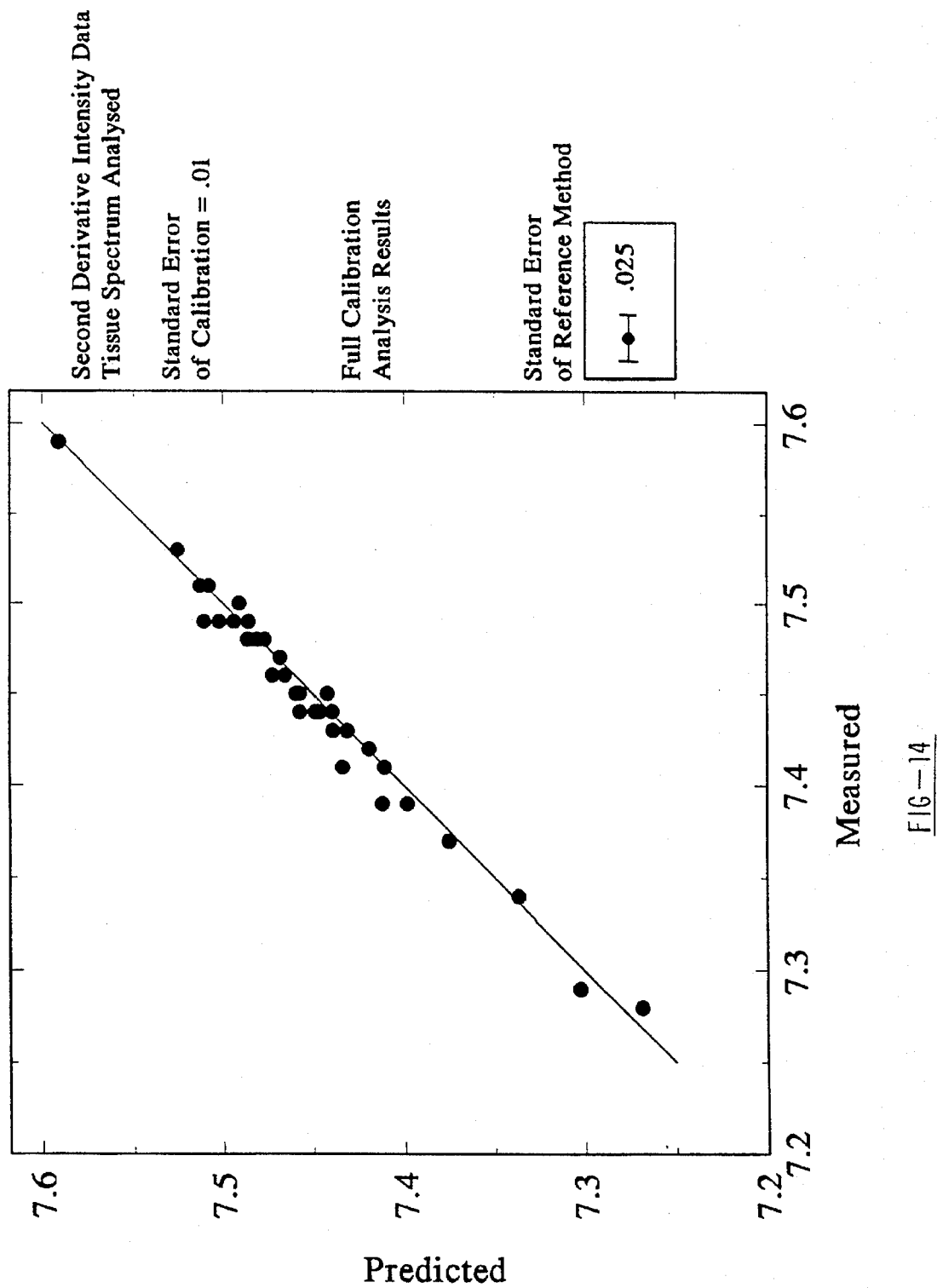
FIG. 14 is a plot of predicted tissue pH vs. measured arterial blood pH utilizing the neural networks algorithm.
Figure 15:
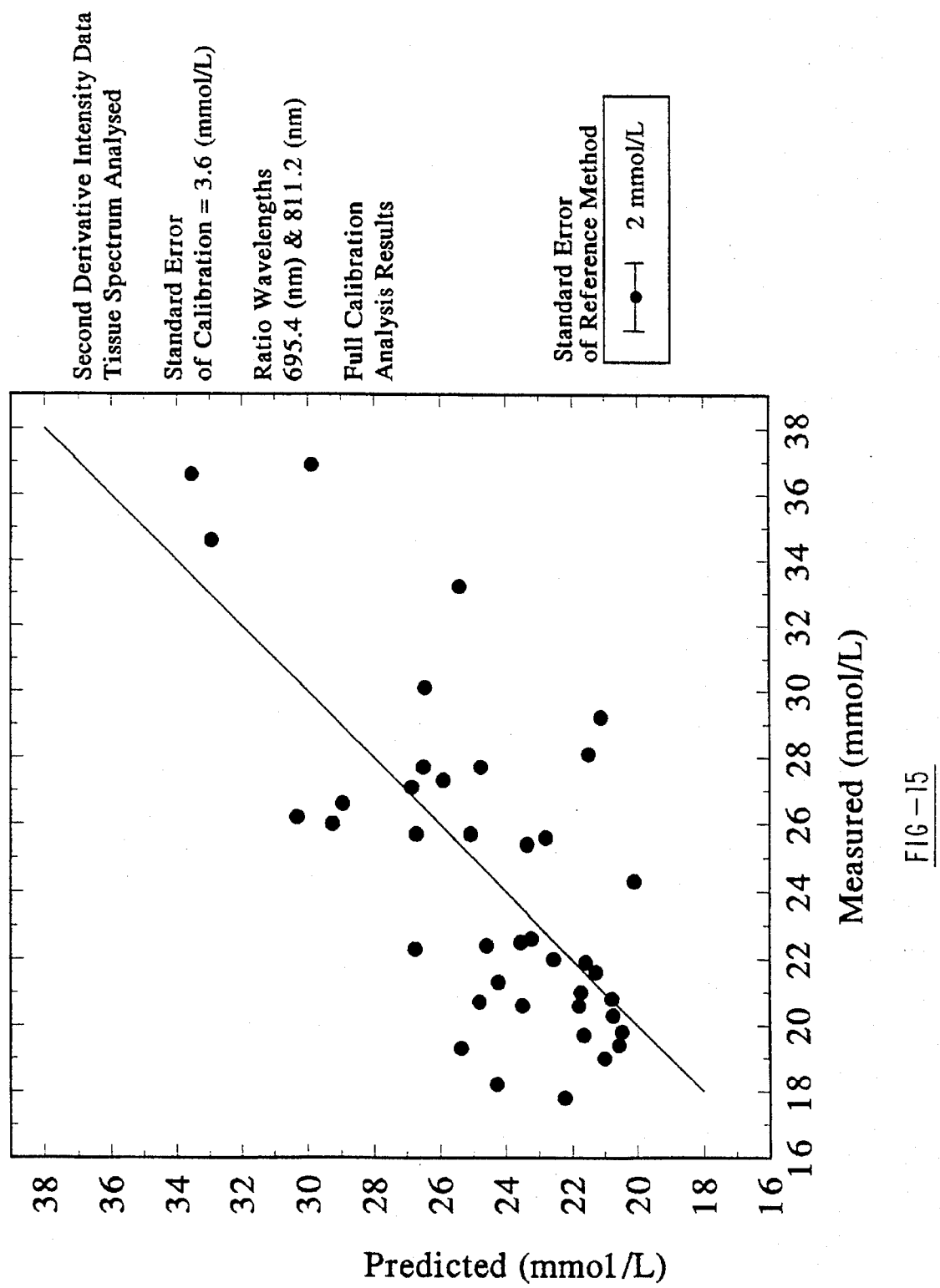
FIG. 15 is a plot of predicted tissue $[HCO_3^-]$ vs. measured arterial blood $[HCO_3^-]$ utilizing the best ratio algorithm.
Figure 16:
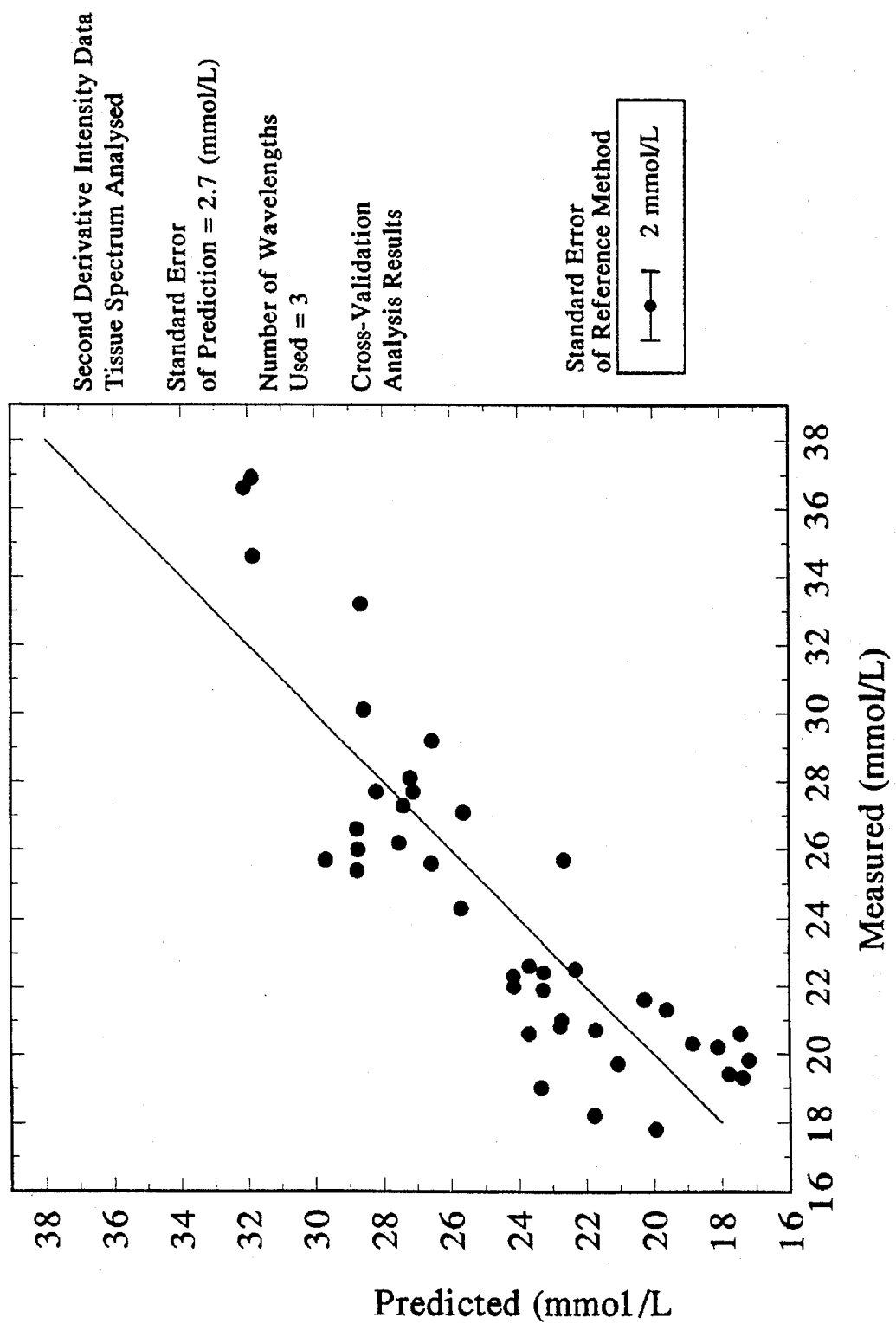
FIG. 16 is a plot of predicted tissue $[HCO_3^-]$ vs. measured arterial blood $[HCO_3^-]$ utilizing MLR.
Figure 17:
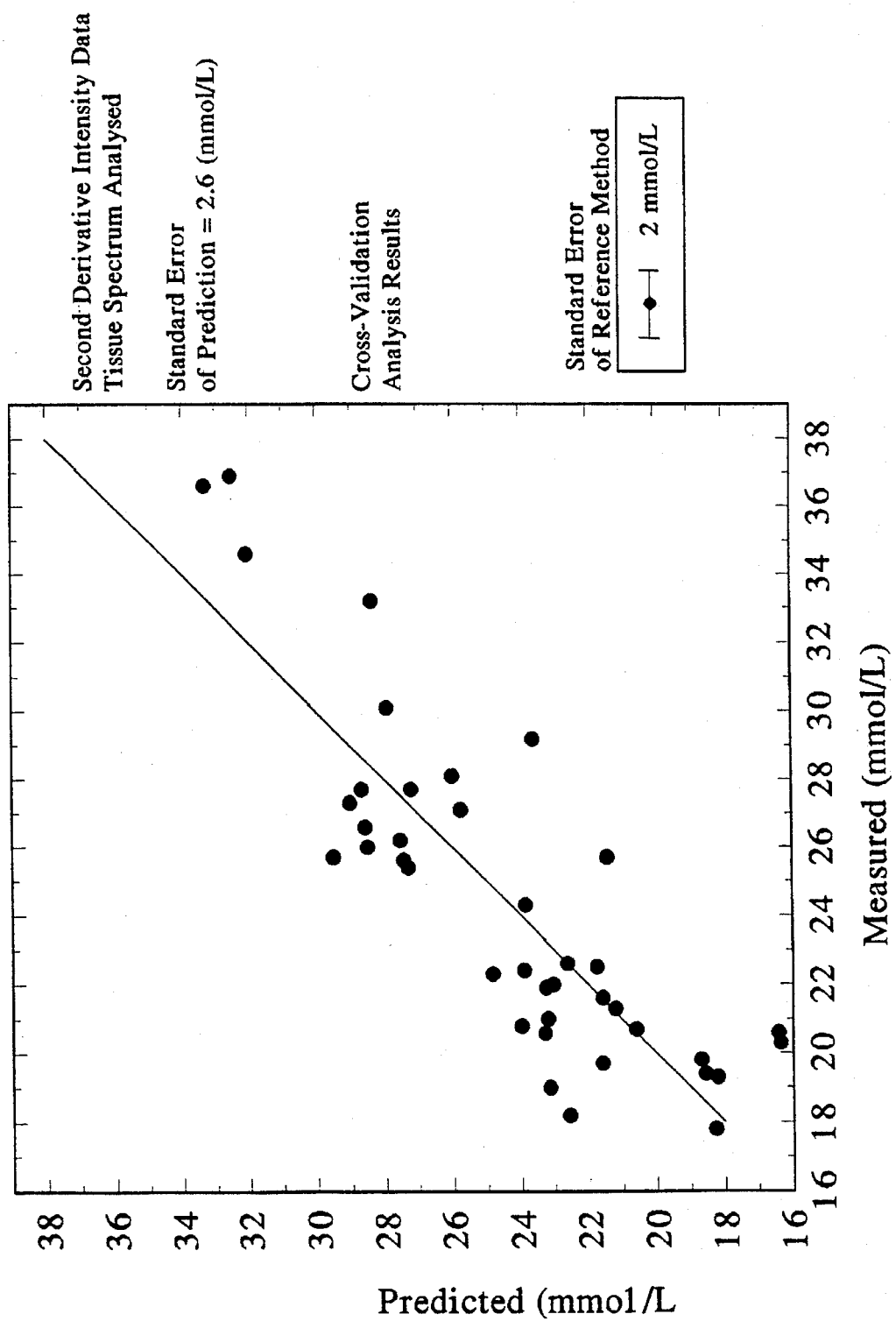
FIG. 17 is a plot of predicted tissue $[HCO_3^-]$ vs. measured arterial blood $[HCO_3^-]$ utilizing PLS.
Figure 18:
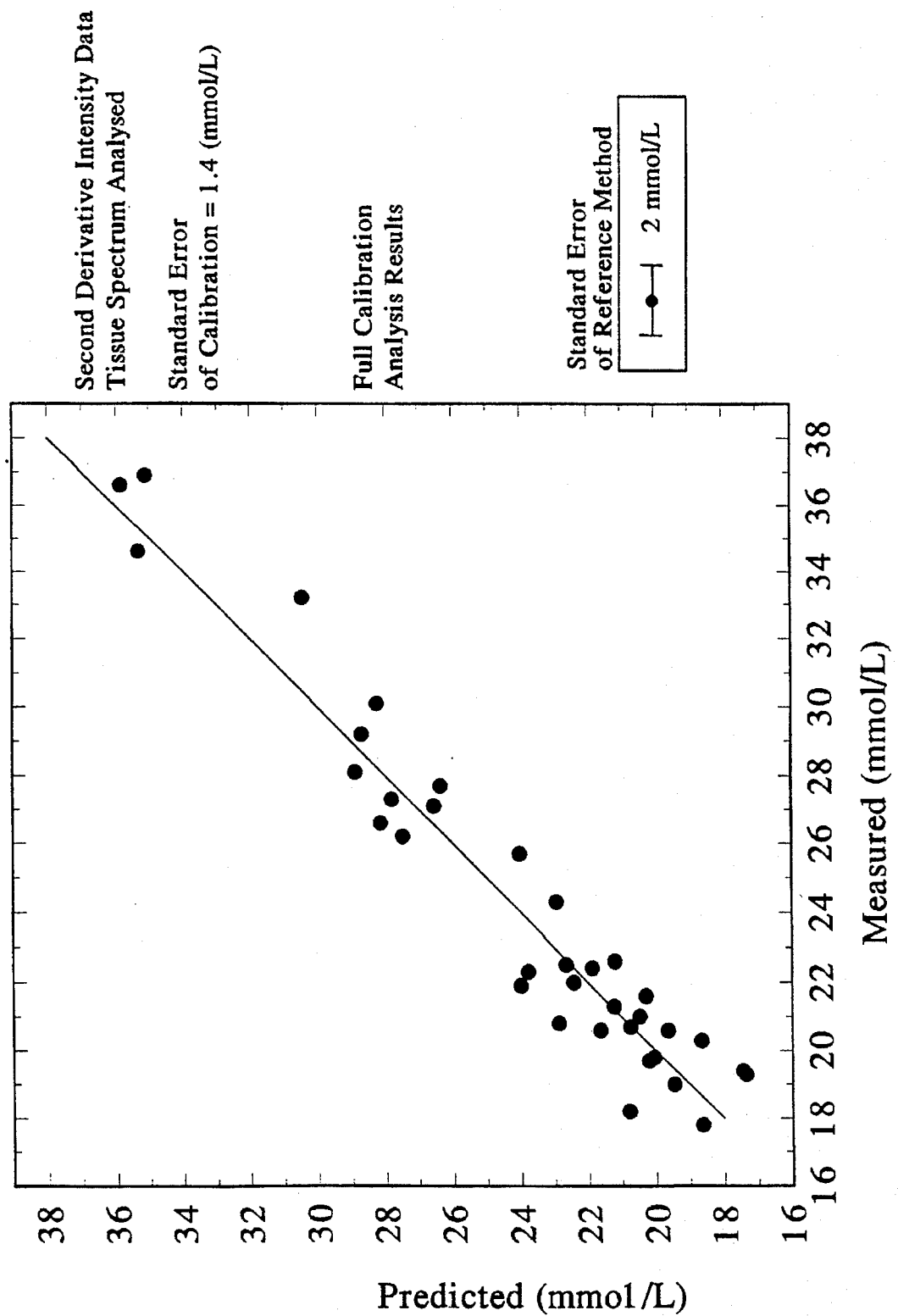
FIG. 18 is a plot of predicted tissue $[HCO_3^-]$ vs. measured arterial blood $[HCO_3^-]$ utilizing the neural networks algorithm.
Figure 19:
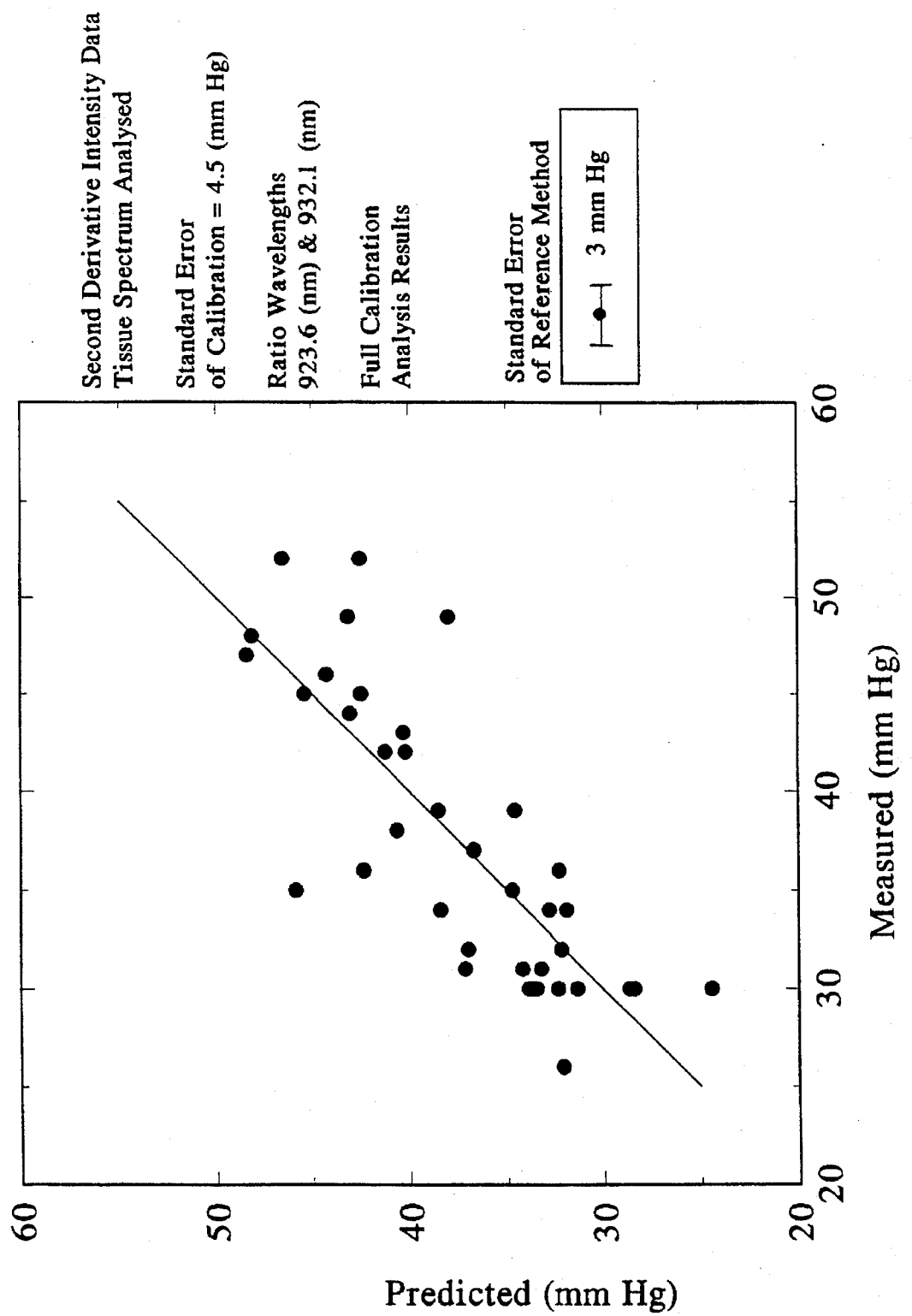
FIG. 19 is a plot of predicted tissue $PCO_2$ vs. measured arterial blood $PCO_2$ utilizing the best ratio algorithm.
Figure 20:
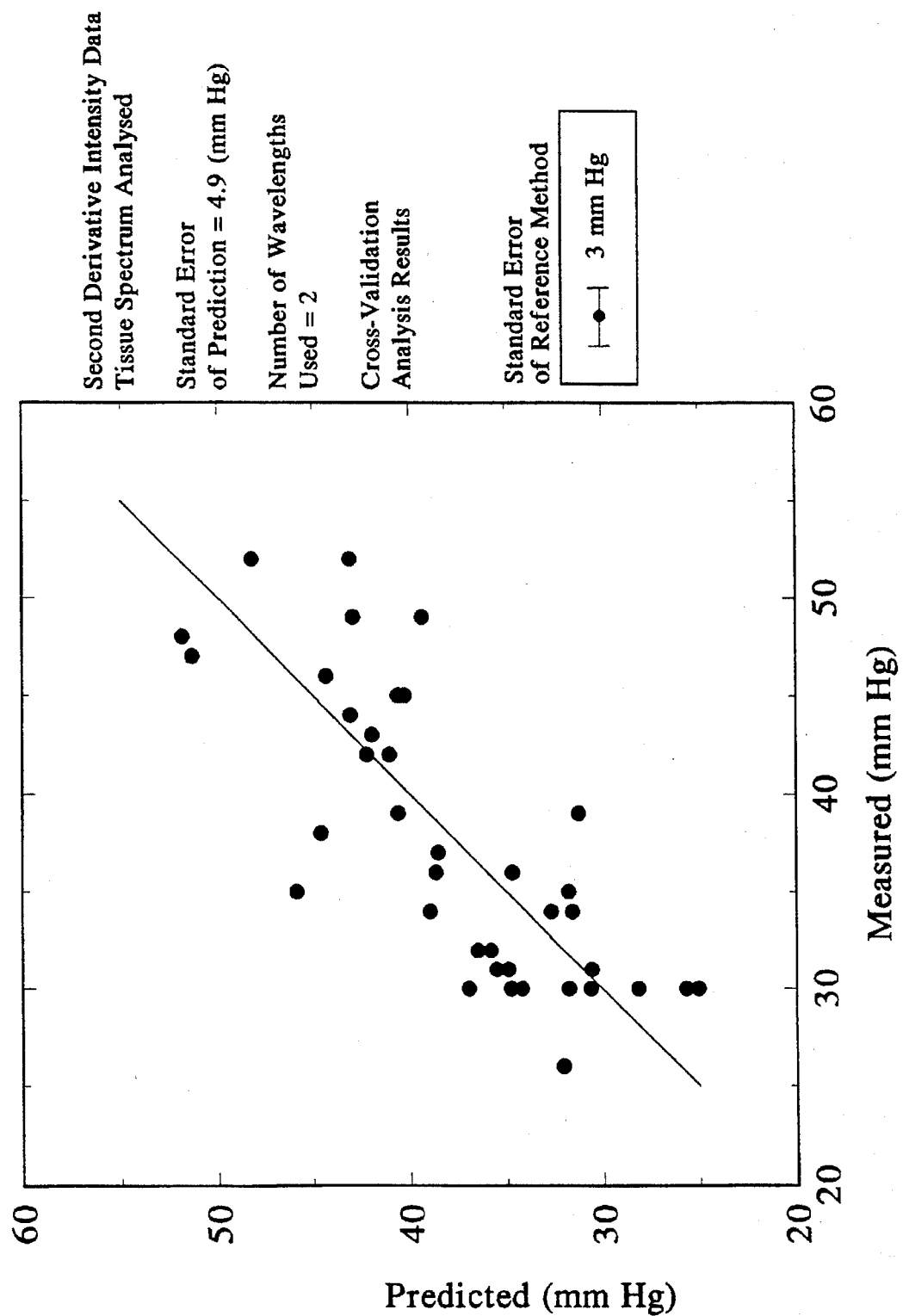
FIG. 20 is a plot of predicted tissue $PCO_2$ vs. measured arterial blood $PCO_2$ utilizing MLR.
Figure 21:
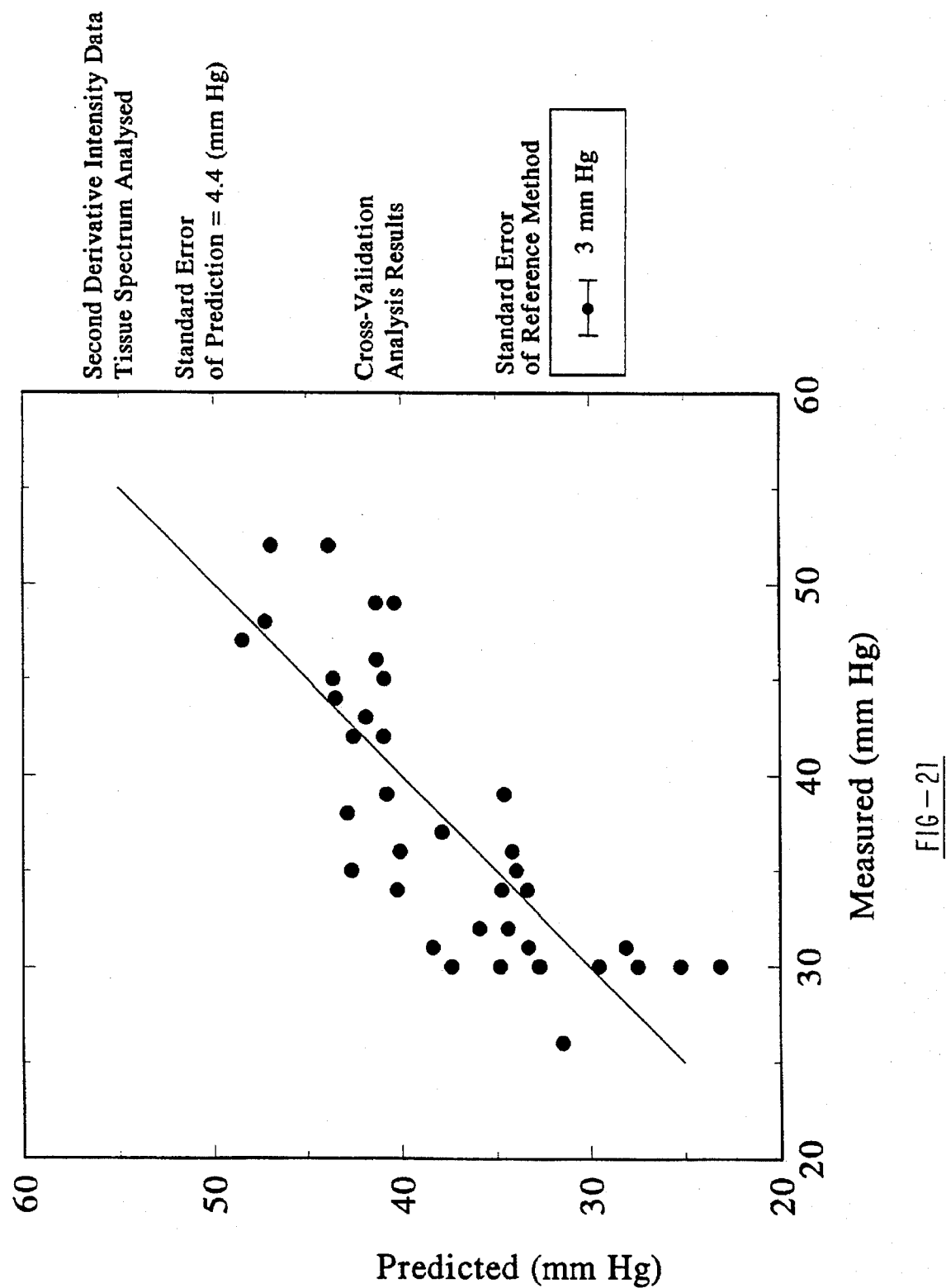
FIG. 21 is a plot of predicted tissue $PCO_2$ vs. measured arterial blood $PCO_2$ utilizing PLS.
Figure 22:
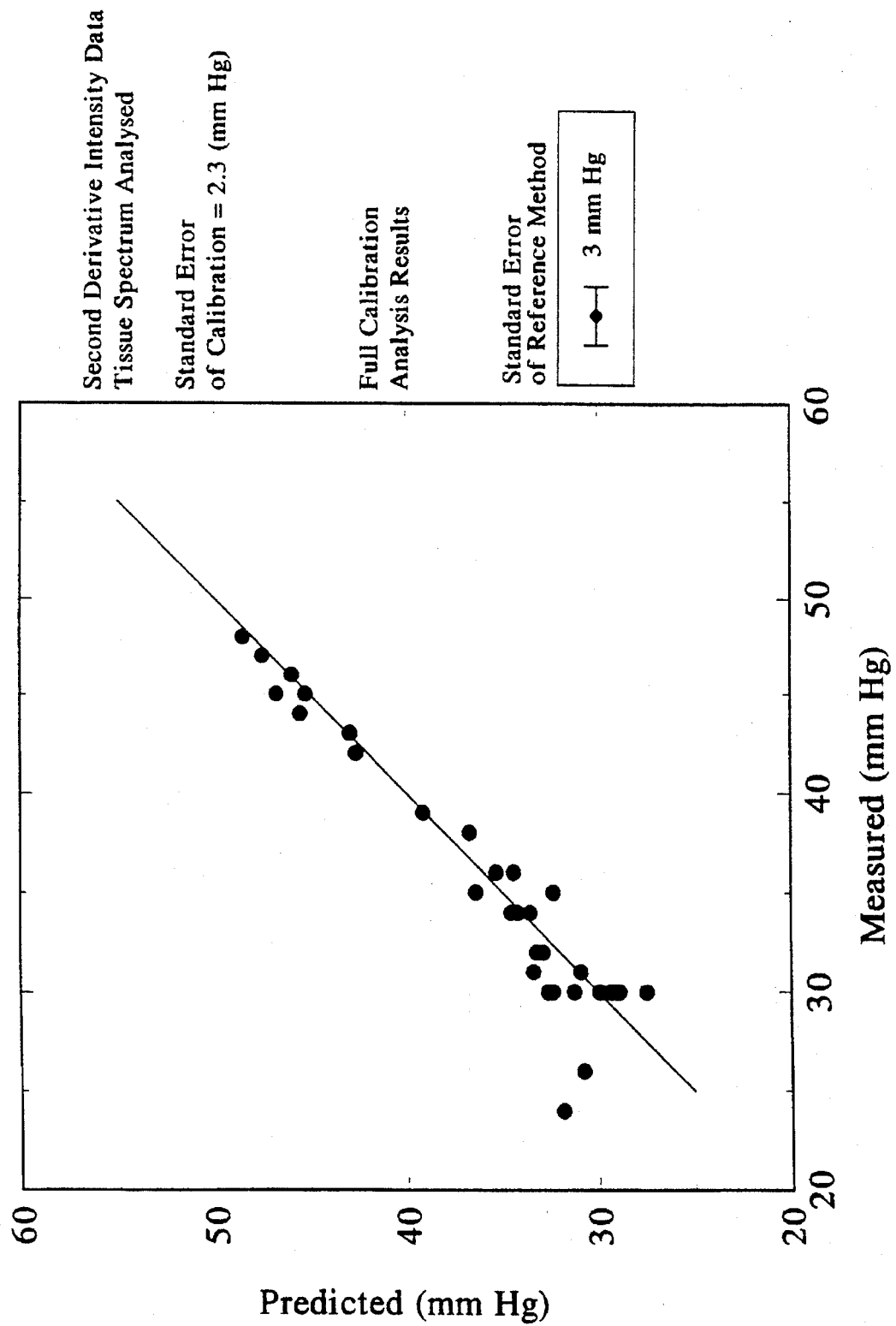
FIG. 22 is a plot of predicted tissue $PCO_2$ vs. measured arterial blood $PCO_2$ utilizing the neural networks algorithm.
Figure 23:
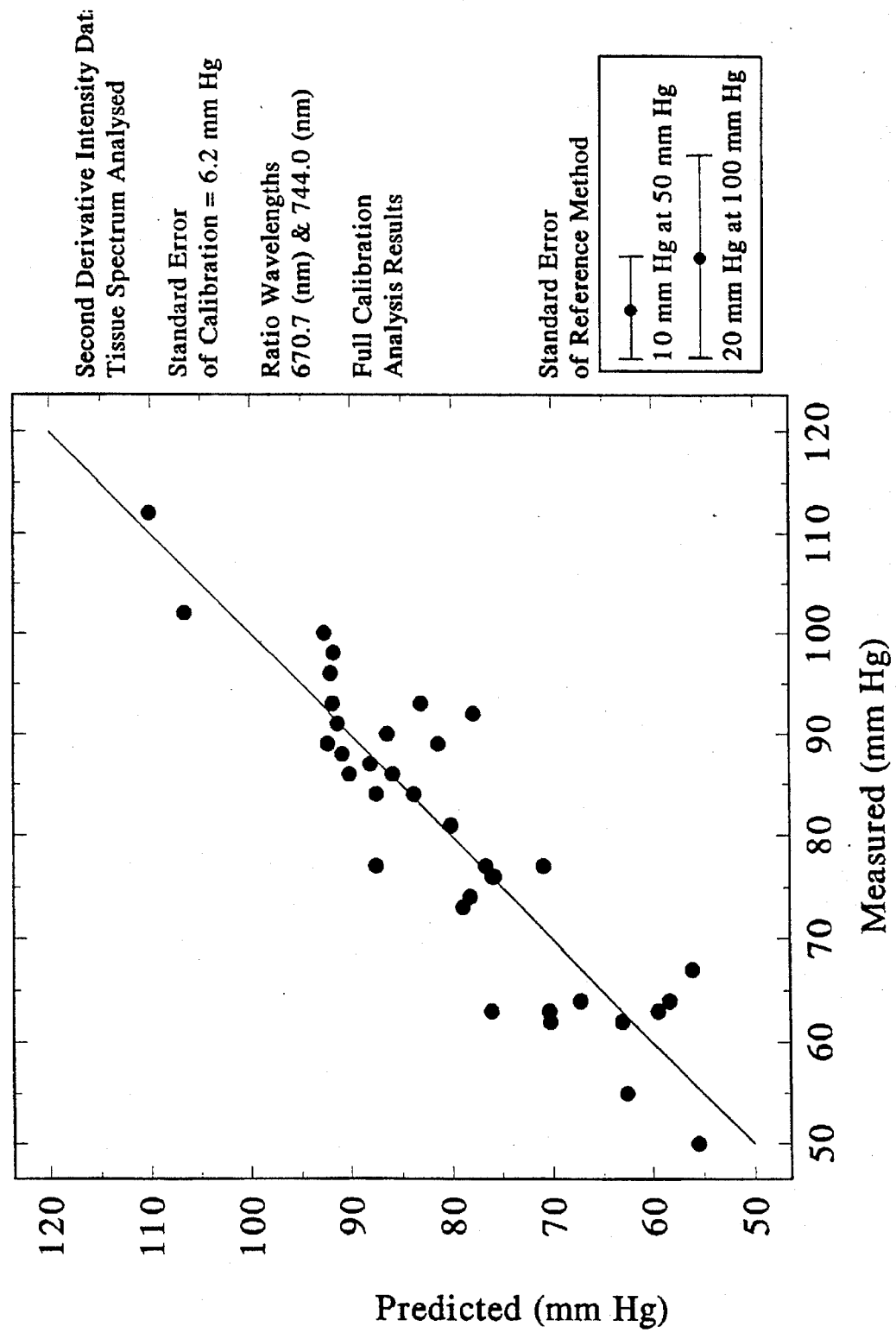
FIG. 23 is a plot of predicted tissue $PO_2$ vs. measured arterial blood $PO_2$ utilizing the best ratio algorithm.
Figure 24:
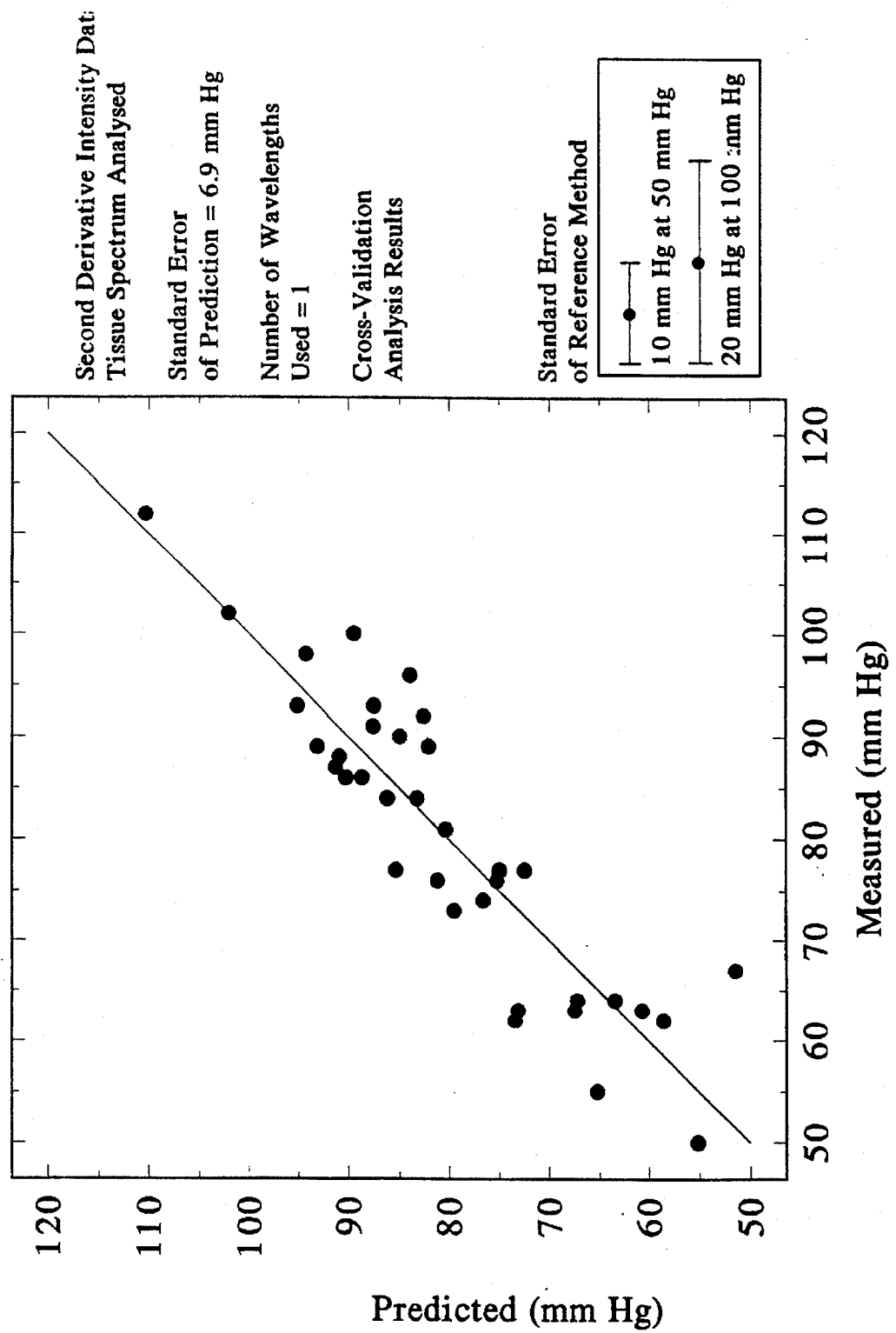
FIG. 24 is a plot of predicted tissue $PO_2$ vs. measured arterial blood $PO_2$ utilizing MLR.
Figure 25:
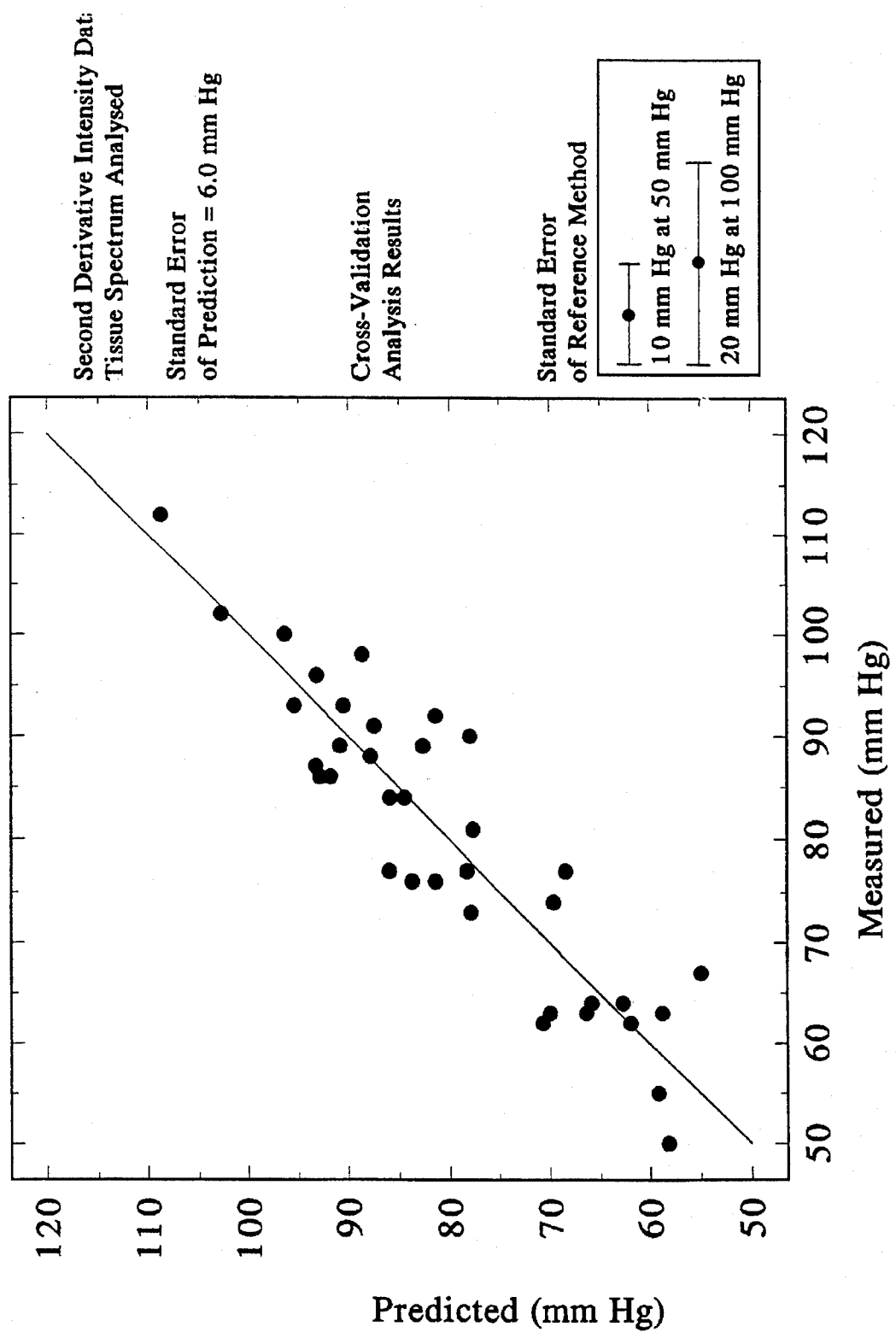
FIG. 25 is a plot of predicted tissue $PO_2$ vs. measured arterial blood $PO_2$ utilizing PLS.
Figure 26:
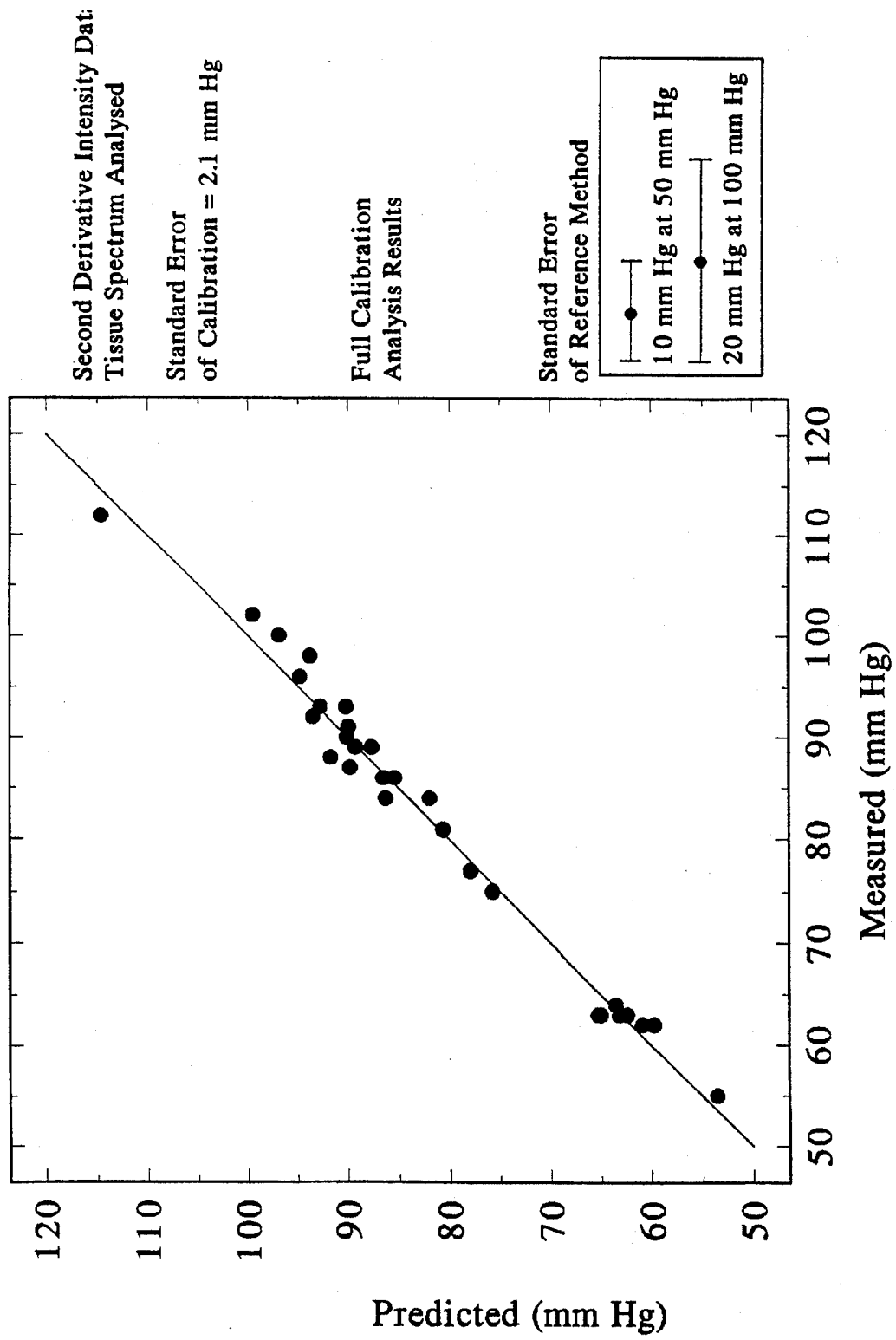
FIG. 26 is a plot of predicted tissue $PO_2$ vs. measured arterial blood $PO_2$ utilizing the neural networks algorithm.
Figure 27:
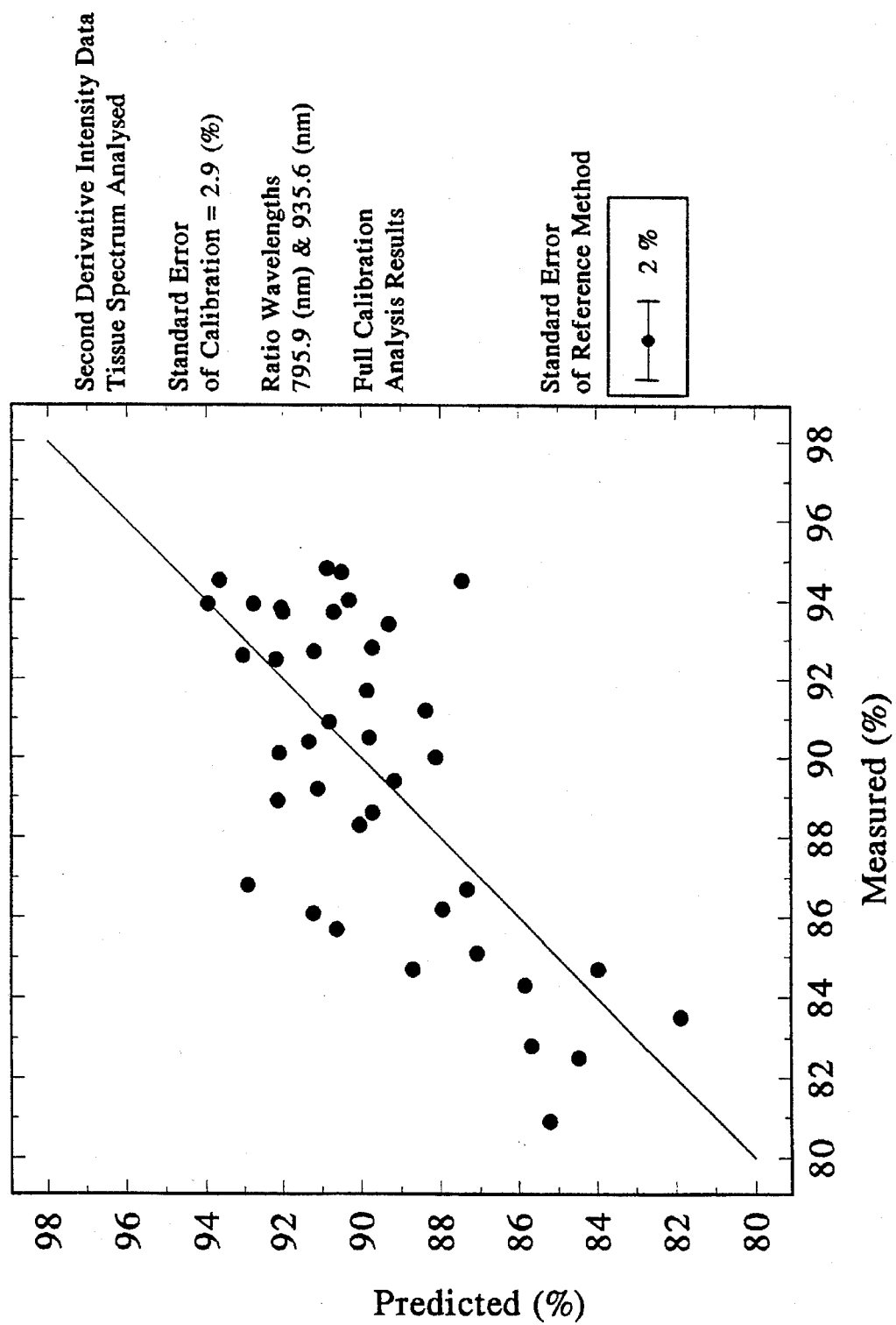
FIG. 27 is a plot of predicted tissue $O_2$ sat. vs. measured arterial blood $O_2$ sat. utilizing the best ratio algorithm.
Figure 28:
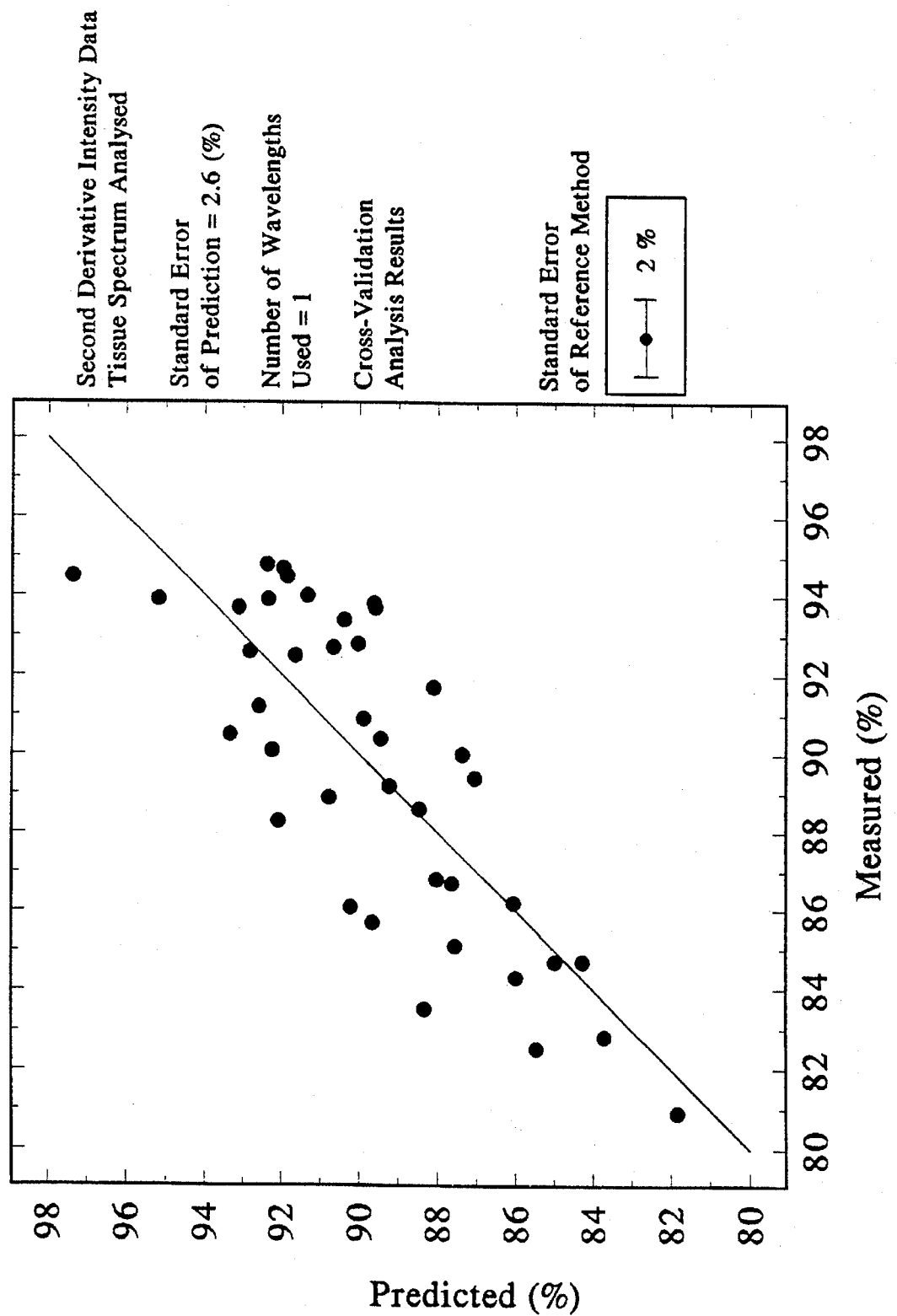
FIG. 28 is a plot of predicted tissue $O_2$ sat. vs. arterial blood measured $O_2$ sat. utilizing MLR.
Figure 29:
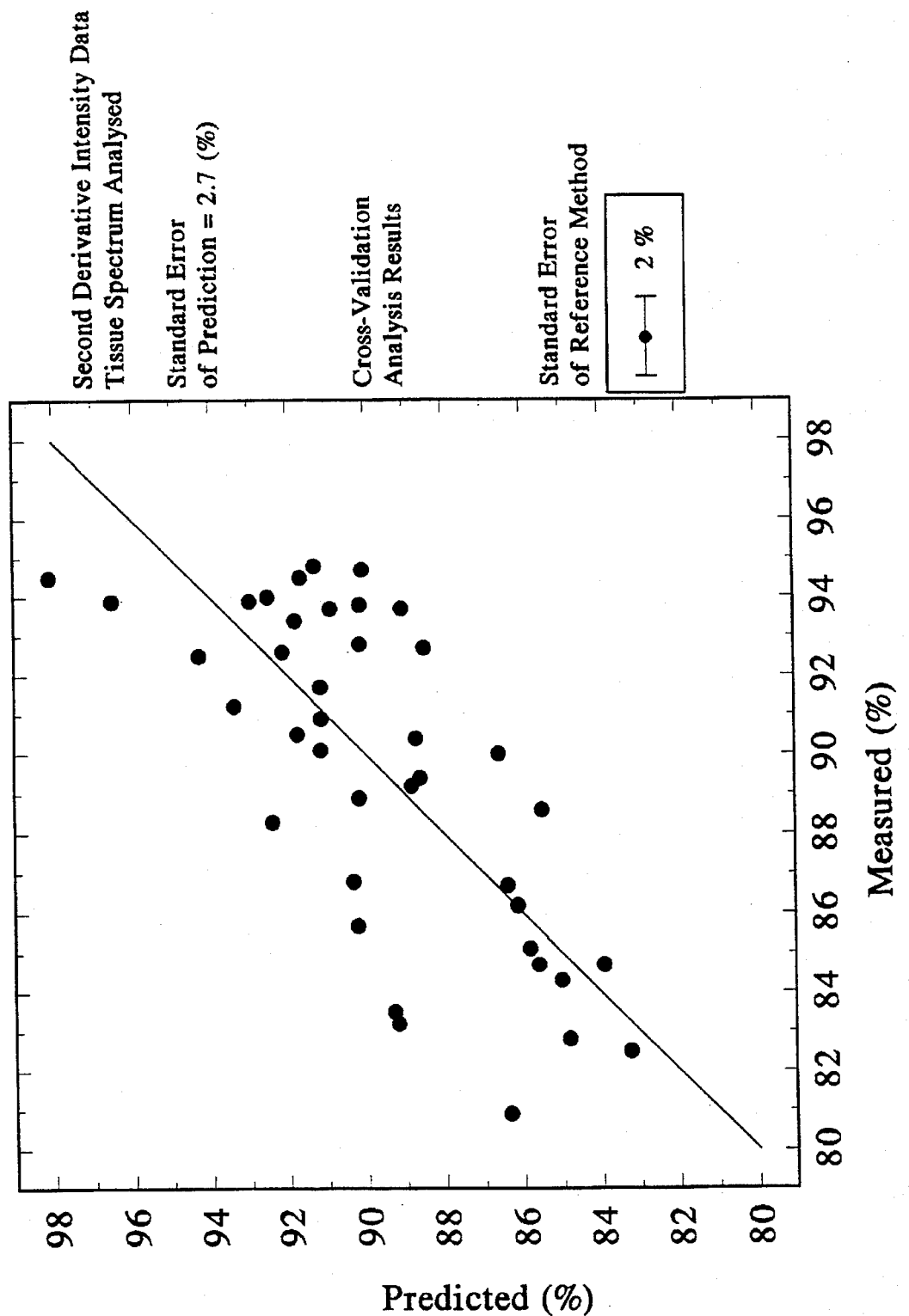
FIG. 29 is a plot of predicted tissue $O_2$ sat. vs. arterial blood measured $O_2$ sat. utilizing PLS.
Figure 30:
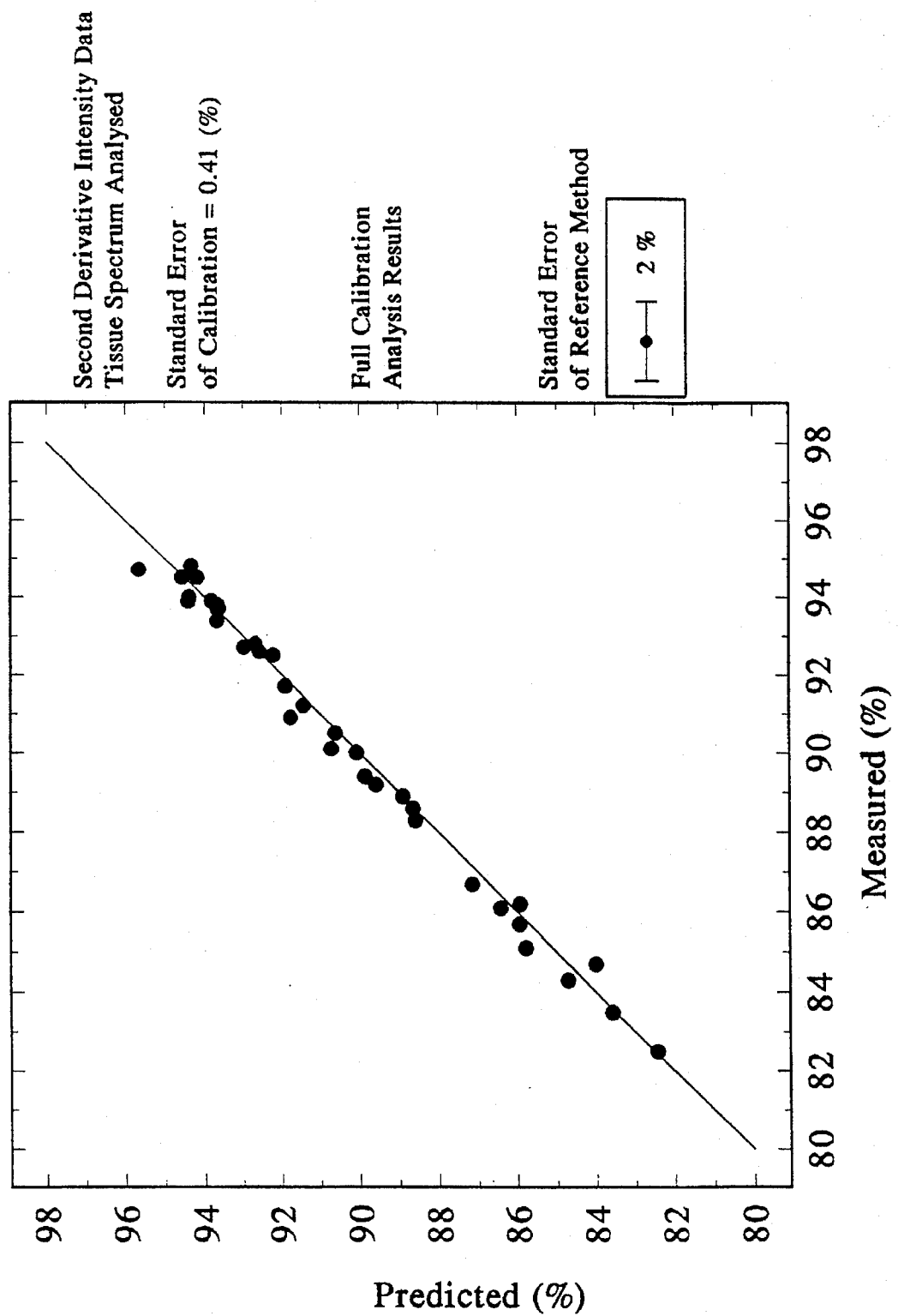
FIG. 30 is a plot of predicted tissue $O_2$ sat. vs. arterial blood measured $O_2$ sat. utilizing the neural networks algorithm.

As previously stated the optical measurement of all arterial blood gas parameters is difficult, as the spectral information for a given analyte typically overlaps with information regions for other analytes. The overlapping of spectral information makes it impossible to make accurate determinations of blood gas parameters by univariate algorithms, if the concentration of the overlapping analyte changes and the magnitude of the spectral changes introduced by the overlapping analyte is similar to that of the analyte of interest. FIG. 10 shows the relationship between the absolute value of the correlation coefficient and wavelength for each blood gas parameter. Examination of FIG. 10 clearly shows that the regions of spectral information overlap.

To demonstrate that various algorithms can be used to measure some or all blood gas parameters, the following algorithms were investigated: (1) best ratio analysis; (2) multiple linear regression; (3) partial least squares; and (4) neural networks.

In comparing the capabilities of the various algorithms it is important to note that the standard error of calibration (SEC) and standard error of prediction (SEP) are presented depending upon the analyte, sample spectra, or algorithm used. These two measures of predictive ability are not the same and have subtle but important differences. The SEC refers to errors in predicting sample analyte values that were used to build the model. The SEP is reported if a cross validation technique was used. When all samples are simultaneously used to develop the calibration model, the SEC reported can be less than the standard error of the reference. Such an occurrence suggests overfitting of the experimental data by the calibration model. The more sophisticated algorithms (e.g. PLS, PCR and neural networks) are all susceptible to some overfitting of this nature when all calibration samples are simultaneously included in the calibration model. If a cross validation technique is used, the standard error of prediction (SEP) can be reported. In the cross validation procedure, one or more samples are omitted from the calibration, and the calibration model is determined based upon this reduced sample set. The concentration of the omitted sample(s) is then predicted using the predetermined calibration model. The process is repeated until each sample has been left out of the calibration model. The SEP, based on cross validation provides a realistic measure of the instrument's prediction ability in the clinical/patient setting. In the discussion that follows, SEC is reported in some cases, while SEP is reported in others. The errors are reported differently due to available computer software, and computational time required. In addition, the errors present in the reference data clearly limit the potential precision of any model. Many of the figures of predicted vs. reference concentrations show large apparent scatter. Often times, this scatter is a direct result of the limited precision of the reference methods. When the prediction precision is the same as the precision of the reference method, then the plots will have the same appearance as if a set of samples were measured two times by the reference method and the reference value of the first measurement were plotted vs. the second.

Best Ratio Analysis

Best ratio analysis is a univariate algorithm commonly used for optical measurements. The predictor variable is a ratio composed of intensities at two wavelengths. The intensity at one wavelength is used to provide base-line information, while the intensity at the second wavelength is specific for the analyte of interest. The standard equation form is Y=M*X+B where the variate X is the ratio of the intensities at the two wavelengths. The Nellcor pulse oximeter uses exactly this principle to measure oxygen saturation. Typically instruments designed for univariate analysis use light emitting diodes. To simulate light emitting diodes, the raw spectral data was averaged using a moving Gaussian weighted average. The resulting data simulates data from a diode with a 10 nm band width.

All possible intensity ratios of the 384 data points collected over the wavelength range 640–970 nm, were calculated and correlated to each blood gas parameter. The ratio which achieved the best correlation was used to create a univariate equation. Table 1 lists the parameter, the number of samples analyzed, and the standard errors of calibration. It is important to note that all samples were used in determining the slope and intercept constants. In univariate analysis the model of the relationship between spectral information and concentration is a straight line defined by the slope and intercept constants. The result of the analysis are illustrated in FIGS. 11, 15, 19, 23, and 27.

TABLE 1

Best Ratio Analysis - Lamb Tissue

| Parameter | Number of Samples | SEC |
| --- | --- | --- |
| pH | 39 | 0.07 |
| $PCO_2$ | 38 | 4.5 |
| $PO_2$ | 36 | 6.2 |
| $[HCO_3^-]$ | 40 | 3.6 |
| $O_2$ sat. | 40 | 2.9 |

Multiple Linear Regression

Multiple Linear Regression was used to analyze the Gaussian averaged intensity spectra. The correlation coefficient between the spectral intensity at each wavelength and the analyte concentration were calculated. The wavelength exhibiting the best correlation coefficient was chosen from the 384 data points covering the wavelength range 640–970 nm as the first wavelength in the model. Subsequent wavelengths were chosen based on correlations between the residuals which remained after information from the previously chosen wavelength(s) was removed. The optimal number of intensities to for analysis was based on the model that yielded the minimum in the cross-calibration SEP.

Table 2 lists the parameter, number of frequencies, the number of samples analyzed, and the standard errors of prediction. The results of the analysis are illustrated in FIGS. 12, 16, 20, and 24. The standard errors of prediction were calculated using a cross validation procedure leaving one sample out at a time.

TABLE 2

MLR - Lamb Tissue

| Parameter | Number of Wavelengths used | Number of Samples | SEP |
| --- | --- | --- | --- |
| pH | 2 | 39 | 0.07 |
| $PCO_2$ | 2 | 38 | 4.9 |
| $PO_2$ | 1 | 36 | 6.9 |
| $[HCO_3^-]$ | 3 | 40 | 2.7 |
| $O_2$ sat. | 1 | 40 | 2.6 |

Partial Least Squares

Partial Least Squares was used to analyze the second derivative of the raw intensity spectra. A 10 point moving average followed by two first difference calculations was used to calculate the derivative. A separate PLS model was formed for each of the five parameters. Table 3 lists the parameters, the number of PLS factors, the wavelength range, the number of samples, and the standard errors of prediction. The standard errors of prediction were calculated using a cross validation procedure. The results of the analysis are illustrated in FIGS. 13, 17, 21, 25, and 29.

TABLE 3

PLS - Lamb Tissue

| Parameter | Number of Factors | Wavelength Range | Number of Samples | SEP |
| --- | --- | --- | --- | --- |
| pH | 7 | 700–800 nm | 39 | 0.03 |
| $PCO_2$ | 1 | 652–955 nm | 38 | 4.4 |
| $PO_2$ | 3 | 652–955 nm | 36 | 6.0 |
| $[HCO_3^-]$ | 3 | 652–955 nm | 40 | 2.6 |
| $O_2$ sat. | 3 | 640–970 nm | 40 | 2.7 |

Neural Networks

A neural network was developed randomly for each of the parameters using a subset of the calibration samples. The subset was chosen randomly Table 4 lists the parameter, the number of samples analyzed, and the standard errors of the calibration. For all analytes measured, the reported SEC is better than the precision of the reference method. This condition indicates that the neural network model relating spectral and concentration information has overfitted the data, and the results are unrealistically good. Nevertheless, neural network analysis of the data worked exceptionally well and the algorithms performance indicates that it is a functional algorithm for the present invention. Neural network cross validation was not performed since the cross-validation algorithms were not available and the computation time required is enormous. The results of the analysis are illustrated in FIGS. 14, 18, 22, 26, and 30.

TABLE 4

Neural Network - Lamb Tissue

| Parameter | Number of Samples | SEC |
| --- | --- | --- |
| pH | 34 | 0.01 |
| $PCO_2$ | 31 | 2.3 |
| $PO_2$ | 29 | 2.1 |
| $[HCO_3^-]$ | 35 | 1.4 |
| $O_2$ sat. | 35 | 0.4 |

Analysis of Spectral Data in Simulated Pulse Blood Mode

Figure 31:
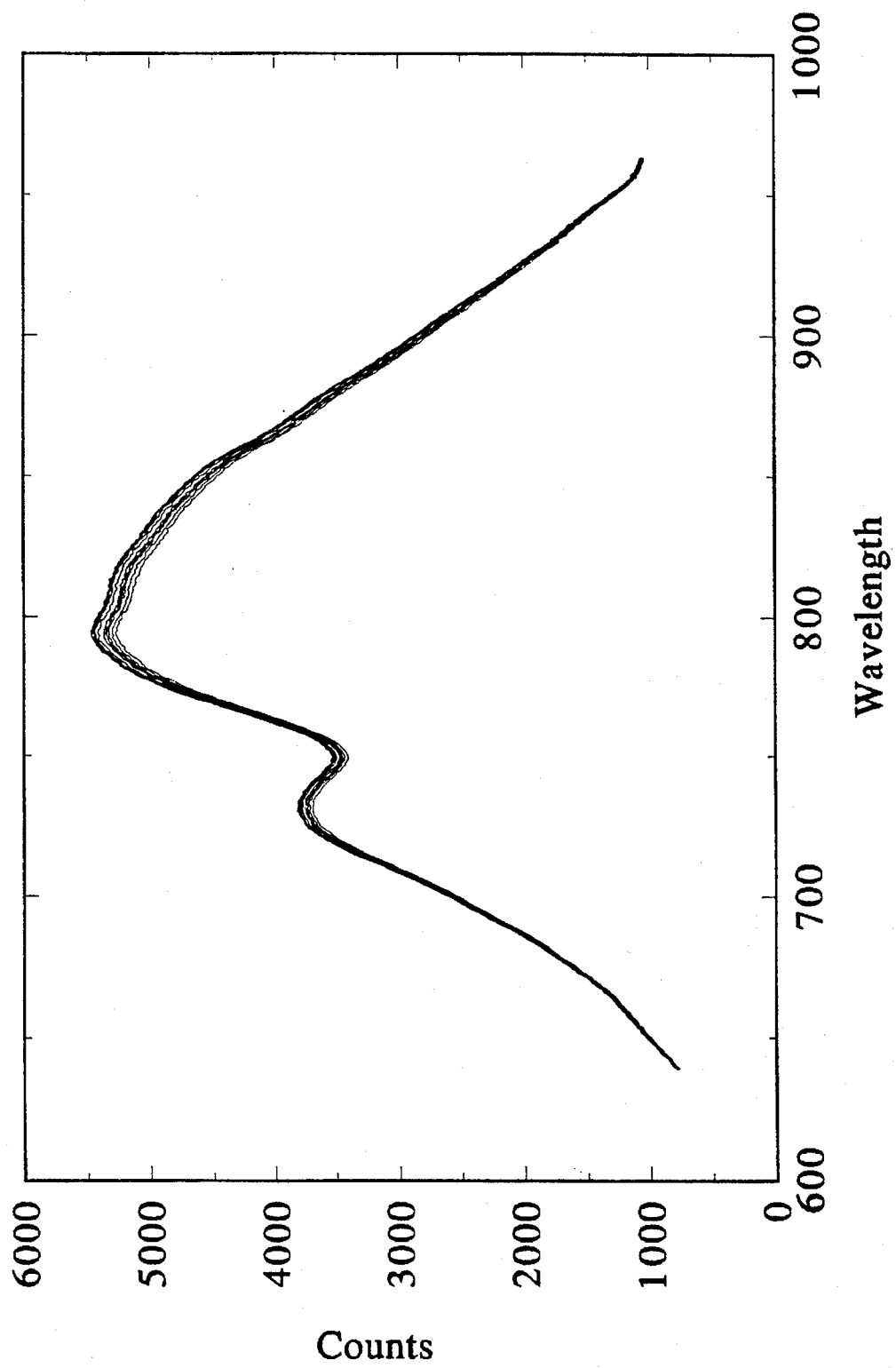
FIG. 31 is a graph of several systolic and diastolic spectra obtained by EKG Lock.
Figure 32:
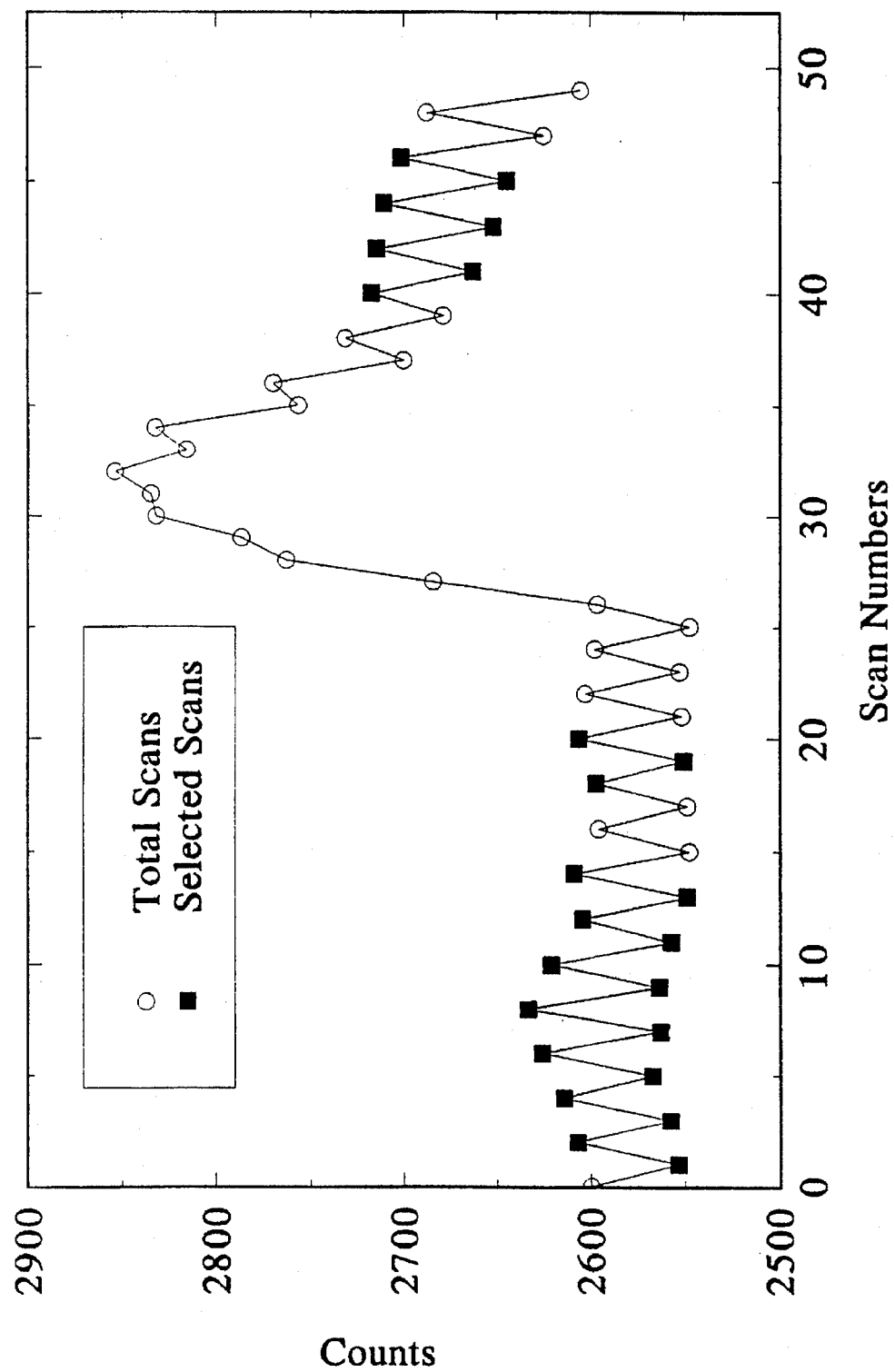
FIG. 32 is a graph of the optical pulse pressure variation during EKG data acquisition.

The EKG lock data was acquired as stated above through the lamb's leg. Twenty five systolic and twenty five diastolic scans were taken at each blood sample observation. FIG. 31 shows five systolic and five diastolic spectra from the lamb's leg. Careful examination of the scans shows some difference between the systolic and diastolic scans. To quantify the difference between the systolic and diastolic spectra, the optical pulse pressure was calculated. The optical pulse pressure was determined by averaging the intensity values from 800 to 810 nm for each spectra. This region of the spectrum was chosen as it is an isobestic region with respect to oxygen saturation. Thus, intensity measurements in this region of the spectrum vary with changing hemoglobin concentration and are not influenced by changes in oxygen saturation. As changing hemoglobin concentration will be proportional to changes in arterial expansion and contraction, analysis of the intensity fluctuations in this region enables quantification of the optical pulse pressure. FIG. 32 is a plot of the intensity values at 800 to 810 nm as a function of scan number.

Examination of FIG. 32 reveals several important characteristics; (1) the optical pulse pressure is quite small; and (2) the summed isobestic intensity values during both systole or diastole are not constant during the sampling period. Variations in the intensity of light transmitted (i.e. optical pulse pressure) arise from changes in the blood fractional volume of the tissue which alters light absorption. Changes in blood fractional volume are correlated with the capillary density in the dermis. Capillary densities for the human have been determined previously by Taylor and Palmer (G. I. Taylor and J. H. Palmer, "The vascular territories of the body: experiment study and clinical applications," British Journal of Plastic Surgery. Vol 40, pp 113–141, 1987.) as well as by Pasyk et al., (K. A. Pasyk, S. V. Thomas, C. A. Hassett, G. W. Cherry, and R. Faller, "Regional differences in capillary density of the normal human dermis," Plastic Reconstructive Surgery, pp 939–945, June 1989). Both investigations have shown a maximum density of blood vessels in the finger followed by the cheek, palm, forearm and lower leg. Thus, in the human the lower leg is the worst of the above locations to obtain an optical pulse. Assuming the capillary densities of the lamb are similar to that of the human, the leg of the lamb will present similar difficulties. However, as the lamb has no fingers, the leg was the only logical location. The end result is that pulse blood measurements from the leg of the lamb are extremely difficult due the minuscule difference between the systolic and diastolic spectra.

The problem of procuring a pulse blood spectrum is compounded by the variations in the spectra as shown in FIG. 31 and in the variations observed in either the systolic or diastolic isobestic sum, as shown in FIG. 32. Examination of all fifty spectra indicated that some spectra were clearly abnormal while some simply had a baseline difference. To procure the best possible pulse blood spectra, the fifty samples were trimmed and then normalized.

Figure 33:
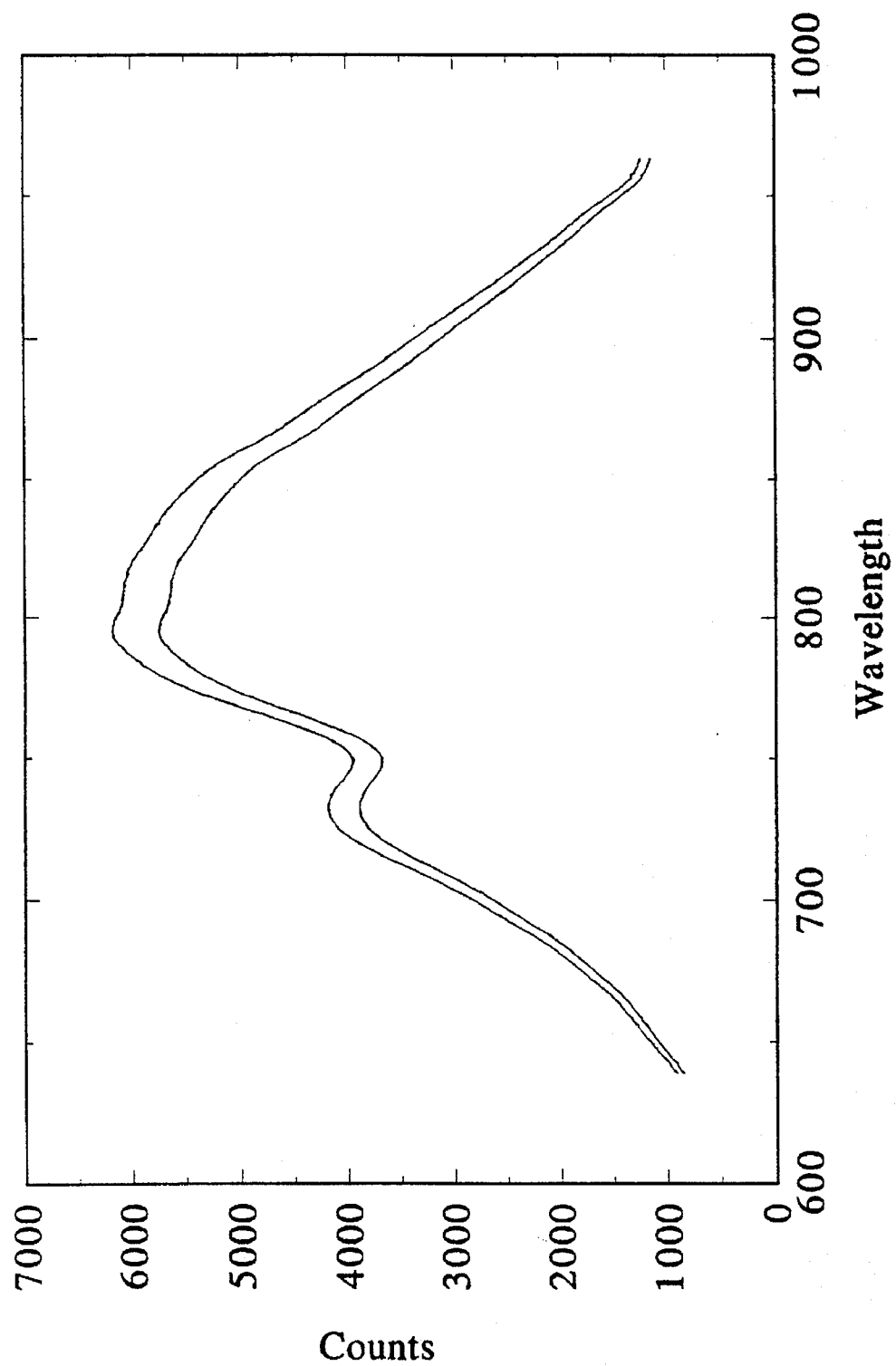
FIG. 33 is a plot of a couple of systolic and diastolic spectra obtained by EKG lock following normalization.
Figure 34:
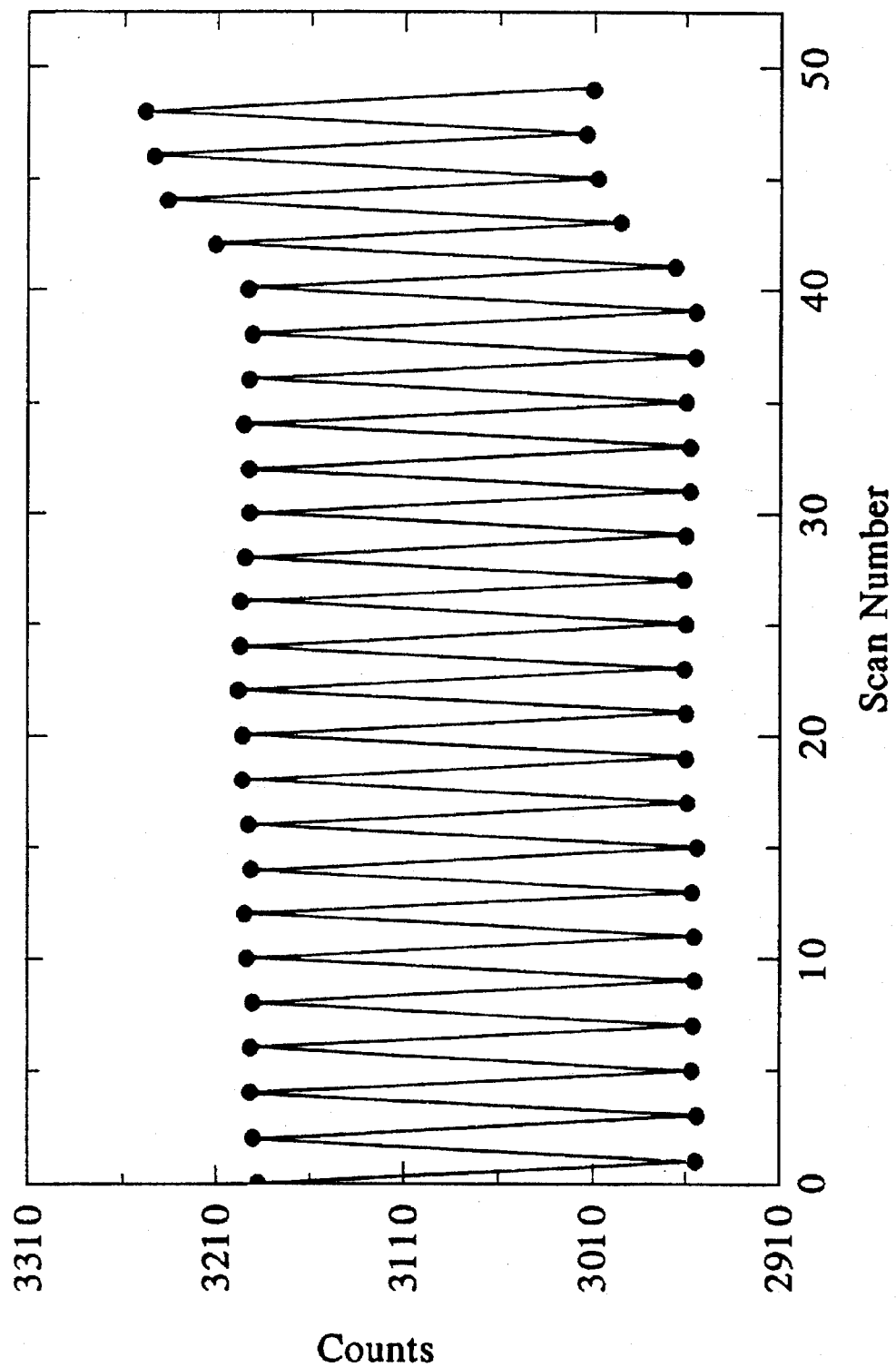
FIG. 34 is a graph of the optical pulse pressure variation of the normalized data taken by EKG lock acquisition.
Figure 35:
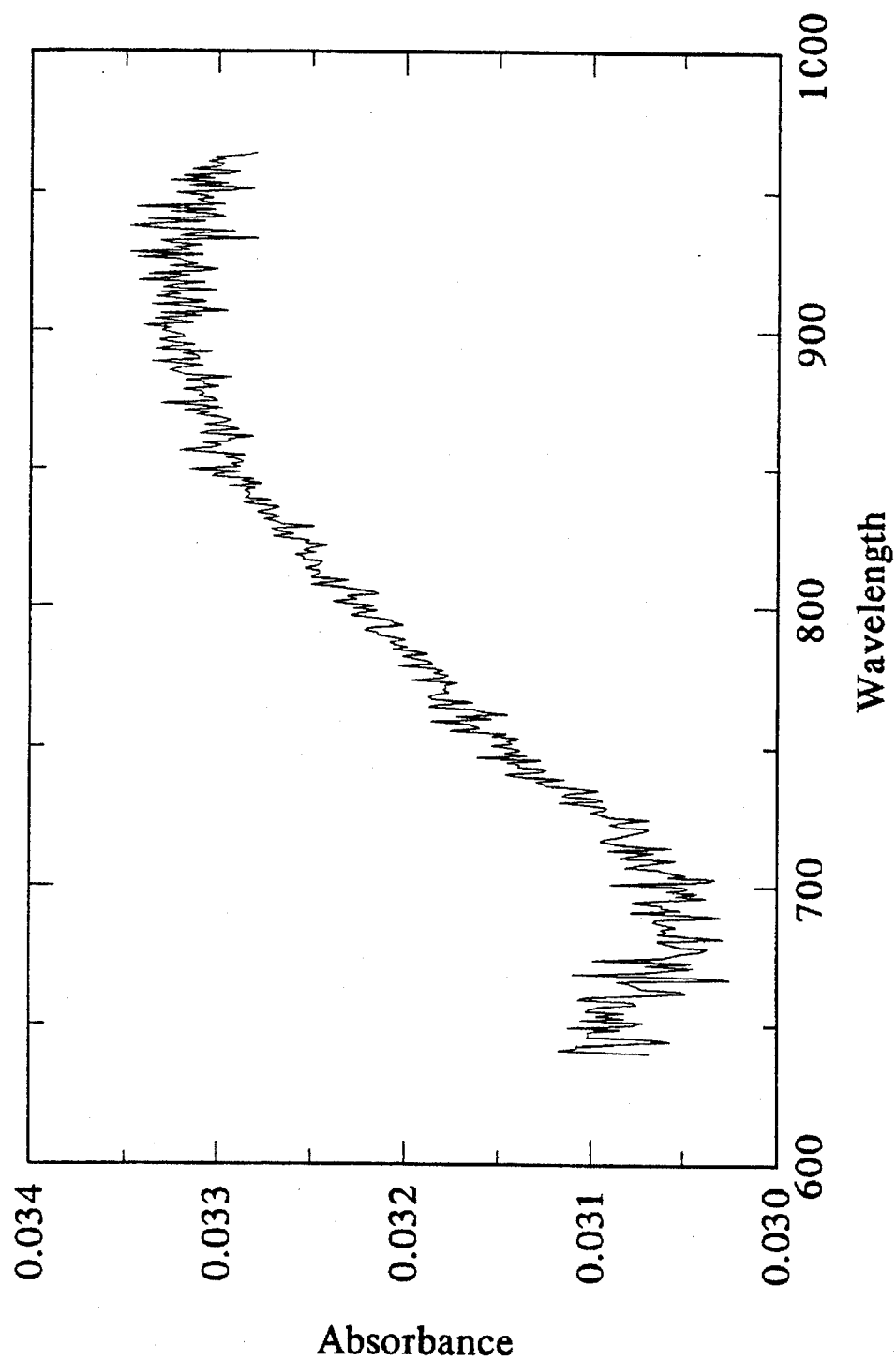
FIG. 35 is a plot of a representative pulse blood spectrum.
Figure 36:
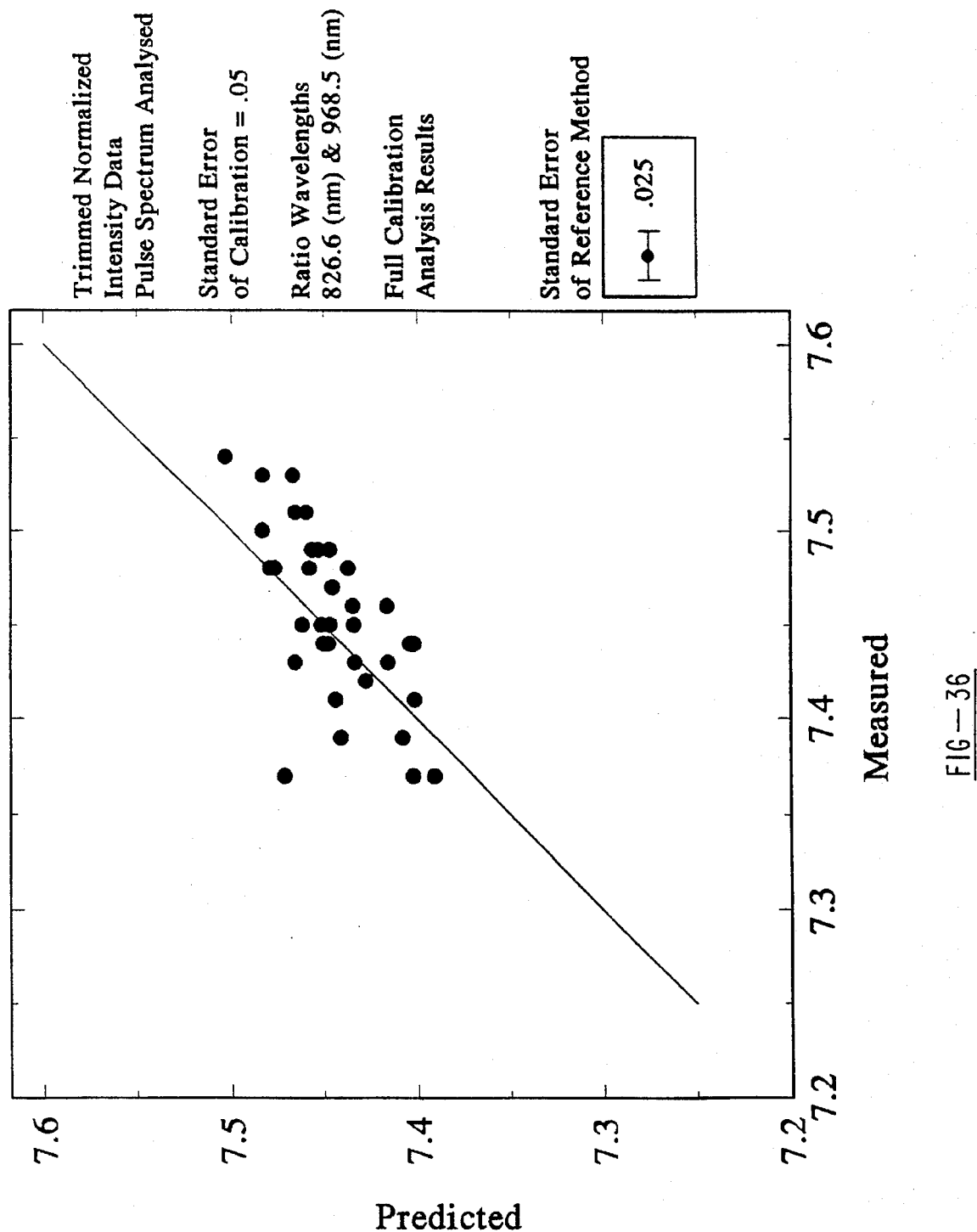
FIG. 36 is a plot of predicted pulse blood spectrum pH (obtained from the tests utilizing the test apparatus illustrated in FIG. 7) vs. measured arterial blood pH using the best ratio algorithm.

The trimming process was based upon the optical pulse pressure observed between sequential systolic and diastolic pulses. The optical pulse pressure valves were ranked in lowest to highest order. Those systolic-diastolic scans which had a optical pulse pressure difference between the 40th and 90th percentile were considered to be representative scans. The samples selected are indicated by a filled square in FIG. 32. Examination of these scans still revealed significant baseline differences. Thus, the selected scans were normalized by the sum of the intensity values over the entire spectrum. Following normalization, all systolic scans had the same intensity sum value over the entire spectrum. The diastolic scans were normalized to a different value, but the process was executed in the same manner. The normalization process can remove linear baselines without altering the shape of the spectrum. The same systolic and diastolic spectra shown in FIG. 31 are, following normalization, plotted in FIG. 33. Examination of FIG. 33 reveals the majority of the initial differences between the systolic or diastolic groups was baseline in nature. FIG. 34 is a plot of the resulting optical pulse pressure vs. scan number, following normalization of all systolic and diastolic scans.

The normalized systolic-diastolic groups selected by the trim procedure were used to calculate the pulse blood spectrum, as follows:

Pulse Blood Spectrum = log (diastolic) − log (systolic)
(spectrum)            (spectrum)

The resulting scans were subsequently averaged to generate the pulse blood spectrum for each observation. FIG. 31 shows a plot of a pulse blood spectra obtained from the lamb's leg. The resulting spectra were subsequently analyzed by several different algorithms: best ratio; multiple linear regression; and partial least squares. As shown in the case of the tissue data, neural networks represent a powerful algorithm that is well suited to this type of analysis. However, analysis by neural networks is not included due to logistical problems in getting the data processed.

The analysis of the pulse blood spectra was done in the same manner as the tissue spectra. The results of the analysis are shown in the following tables. The analysis of the spectra to quantify the partial pressure of carbon dioxide did not yield predictive relevance. Thus, no $PCO_2$ predictions are included.

Best Ratio Analysis

Best ratio analysis of the trimmed, normalized pulse blood spectra was done in the same manner as set forth above, including processing of the spectra with a moving Gaussian weighted average. The results are shown in FIGS. 36, 39, 42 and 45.

TABLE 5

| Best Ratio - Pulse Blood | | |
|---|---|---|
| Parameter | Number of Samples | SEC |
| pH | 32 | 0.05 |
| $PO_2$ | 42 | 12.7 |
| $[HCO_3^-]$ | 38 | 3.65 |
| $O_2$ sat. | 38 | 3.55 |

Multiple Linear Regression

Figure 37:
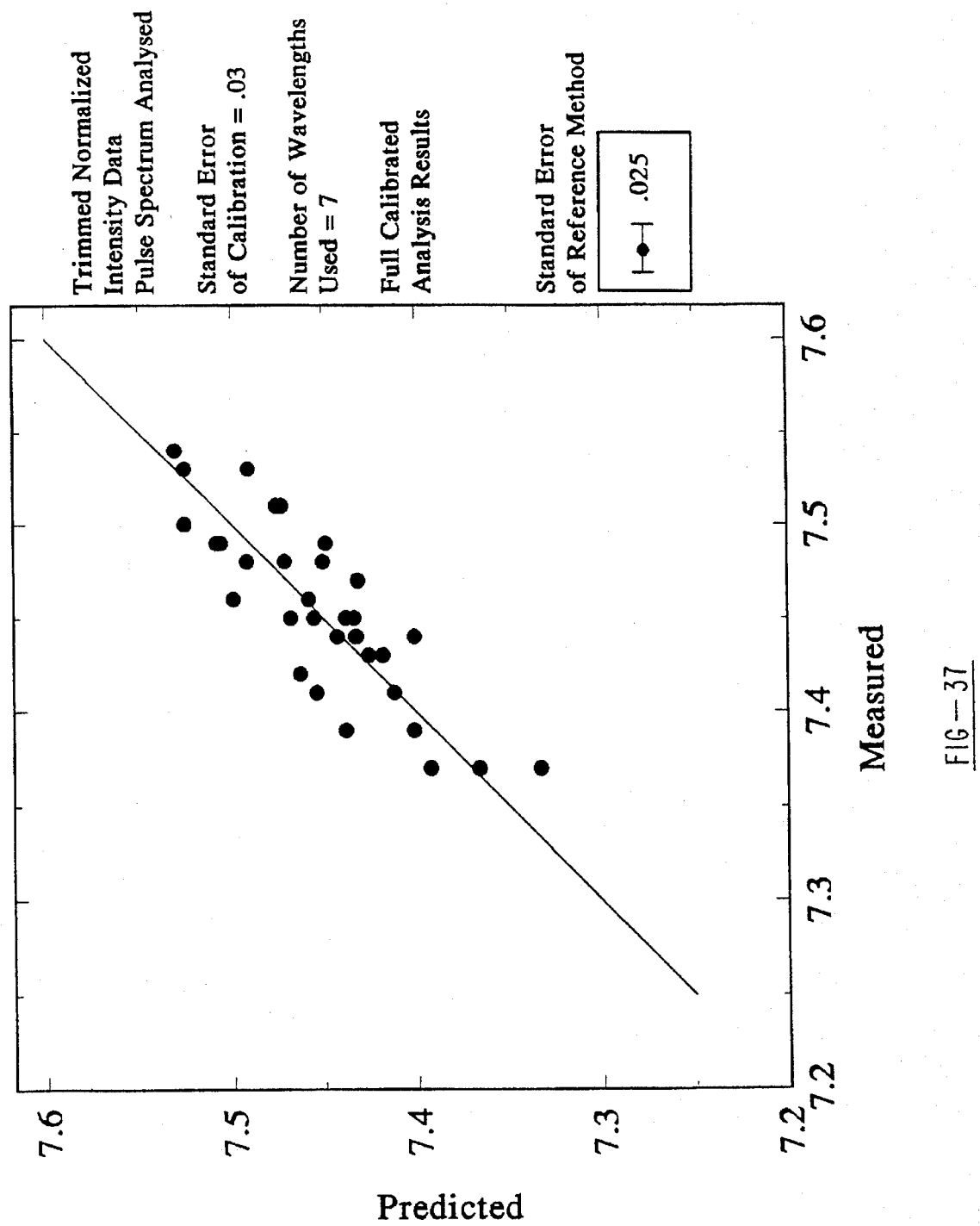
FIG. 37 is a plot of predicted pulse blood spectrum pH vs. measured arterial blood pH utilizing MLR.
Figure 38:
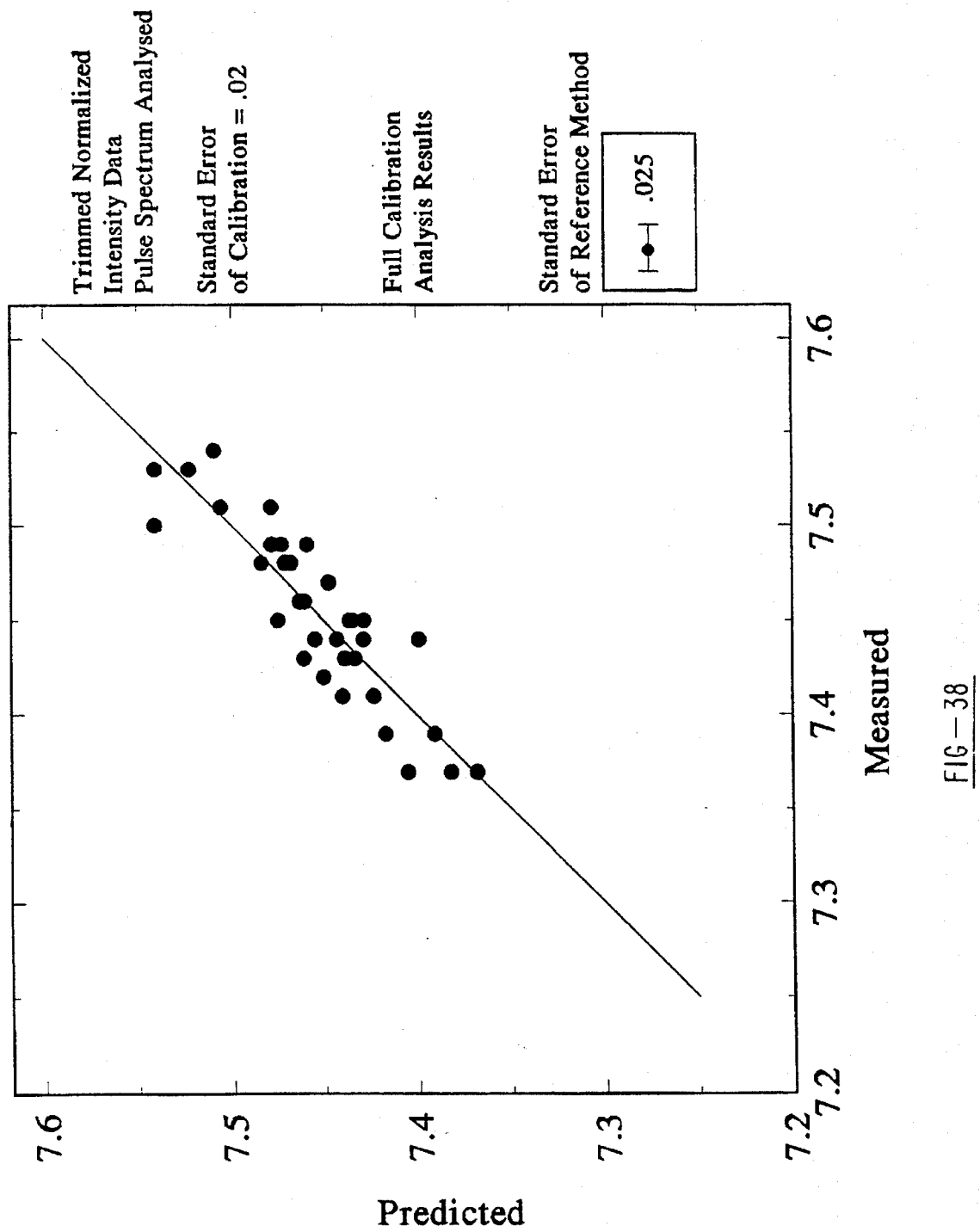
FIG. 38 is a plot of predicted pulse blood spectrum pH vs. measured arterial blood pH utilizing PLS.
Figure 39:
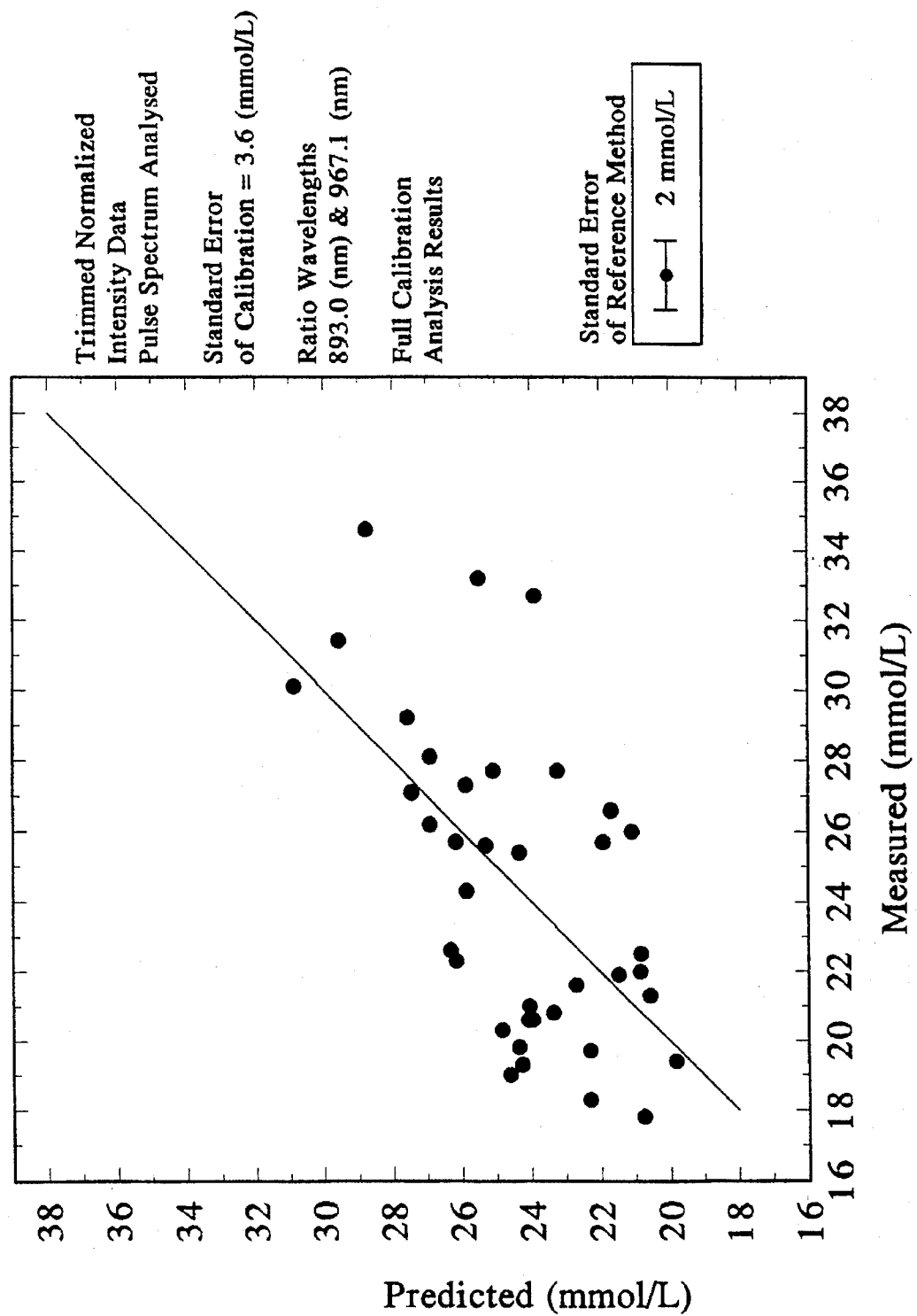
FIG. 39 is a plot of predicted pulse blood spectrum $[HCO_3^-]$ vs. measured arterial blood $[HCO_3^-]$ utilizing the best ratio algorithm.
Figure 40:
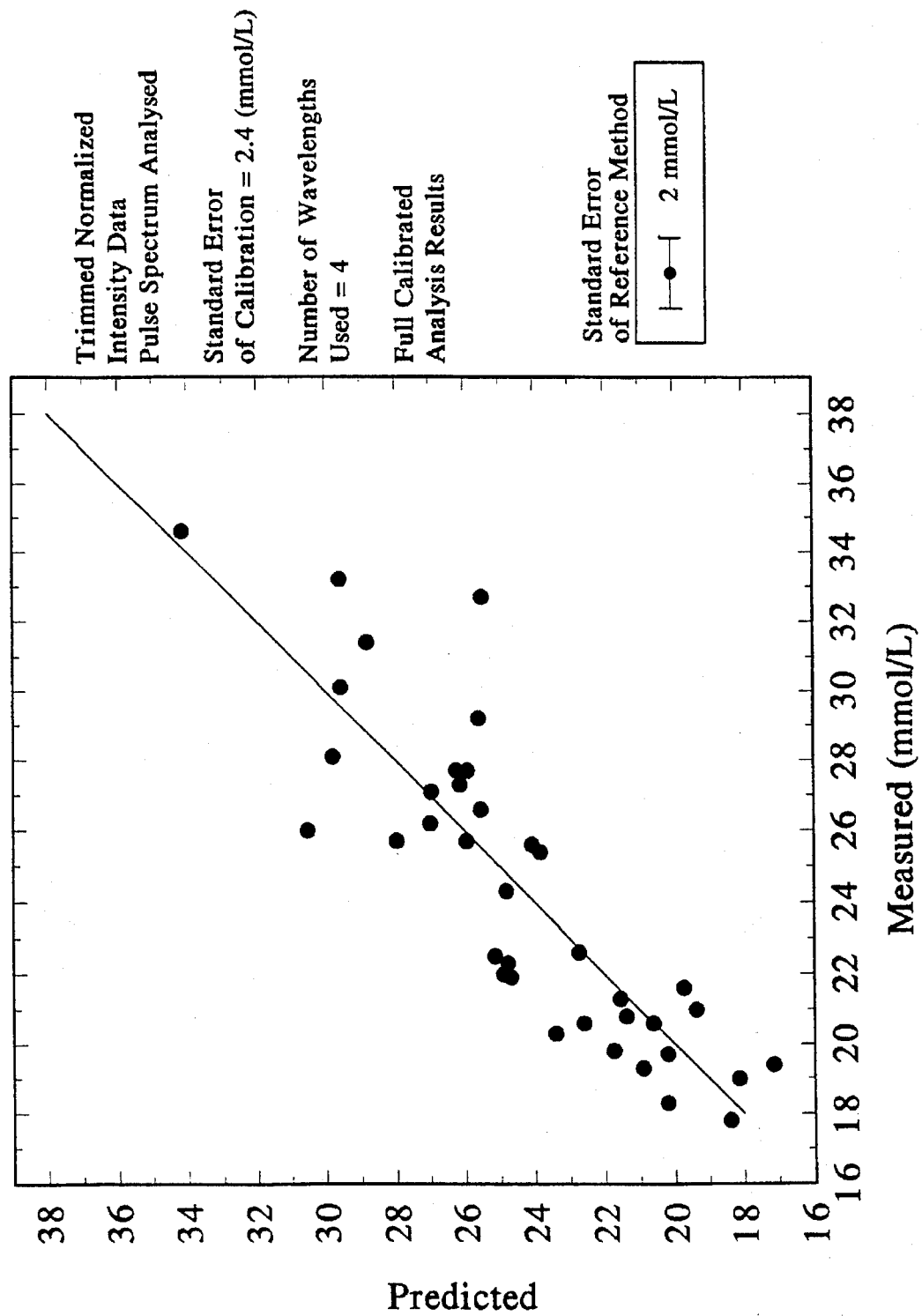
FIG. 40 is a plot of predicted pulse blood spectrum $[HCO_3^-]$ vs. measured arterial blood $[HCO_3^-]$ utilizing MLR.
Figure 41:
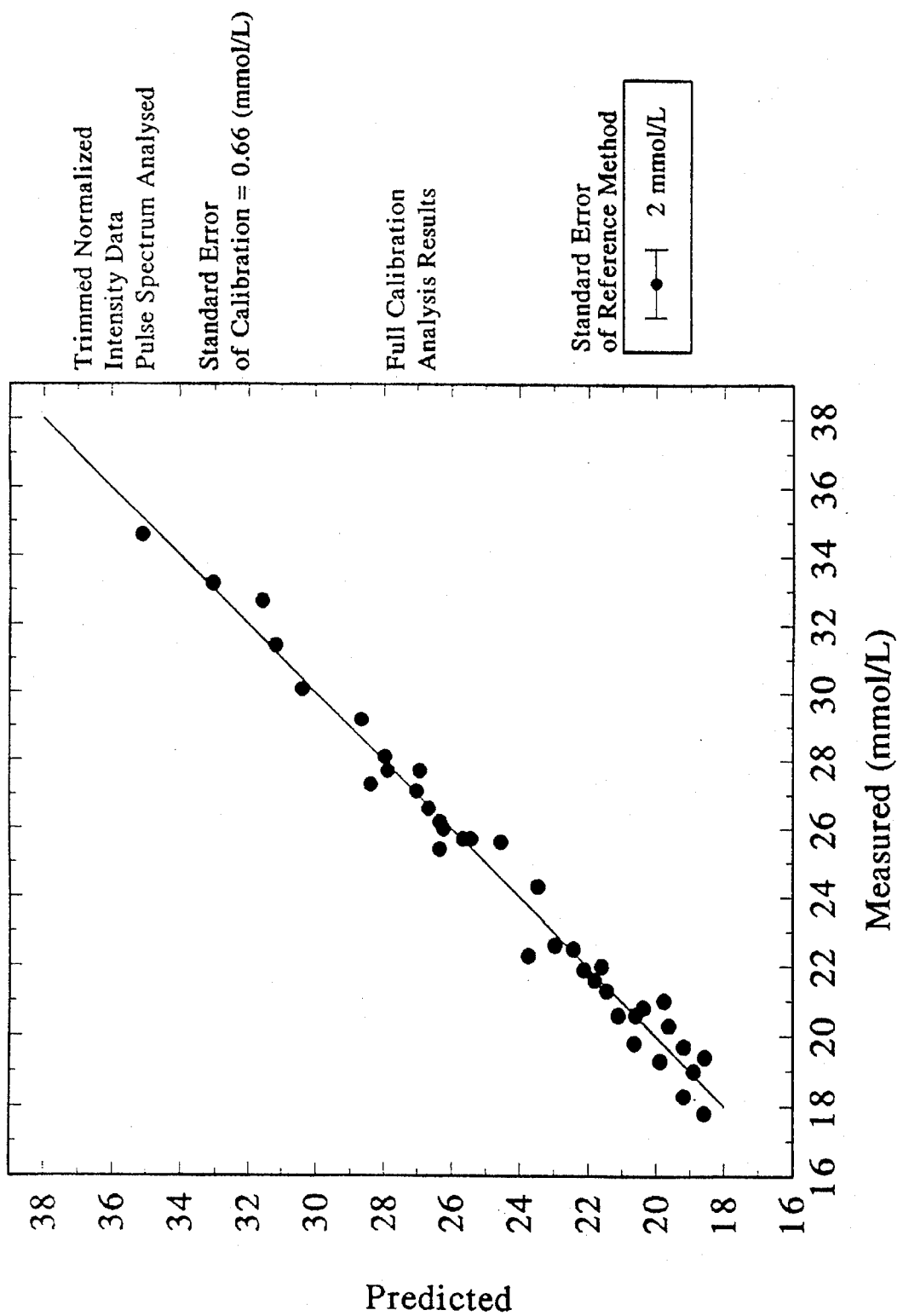
FIG. 41 is a plot of predicted pulse blood spectrum $[HCO_3^-]$ vs. measured arterial blood $[HCO_3^-]$ utilizing PLS.
Figure 42:
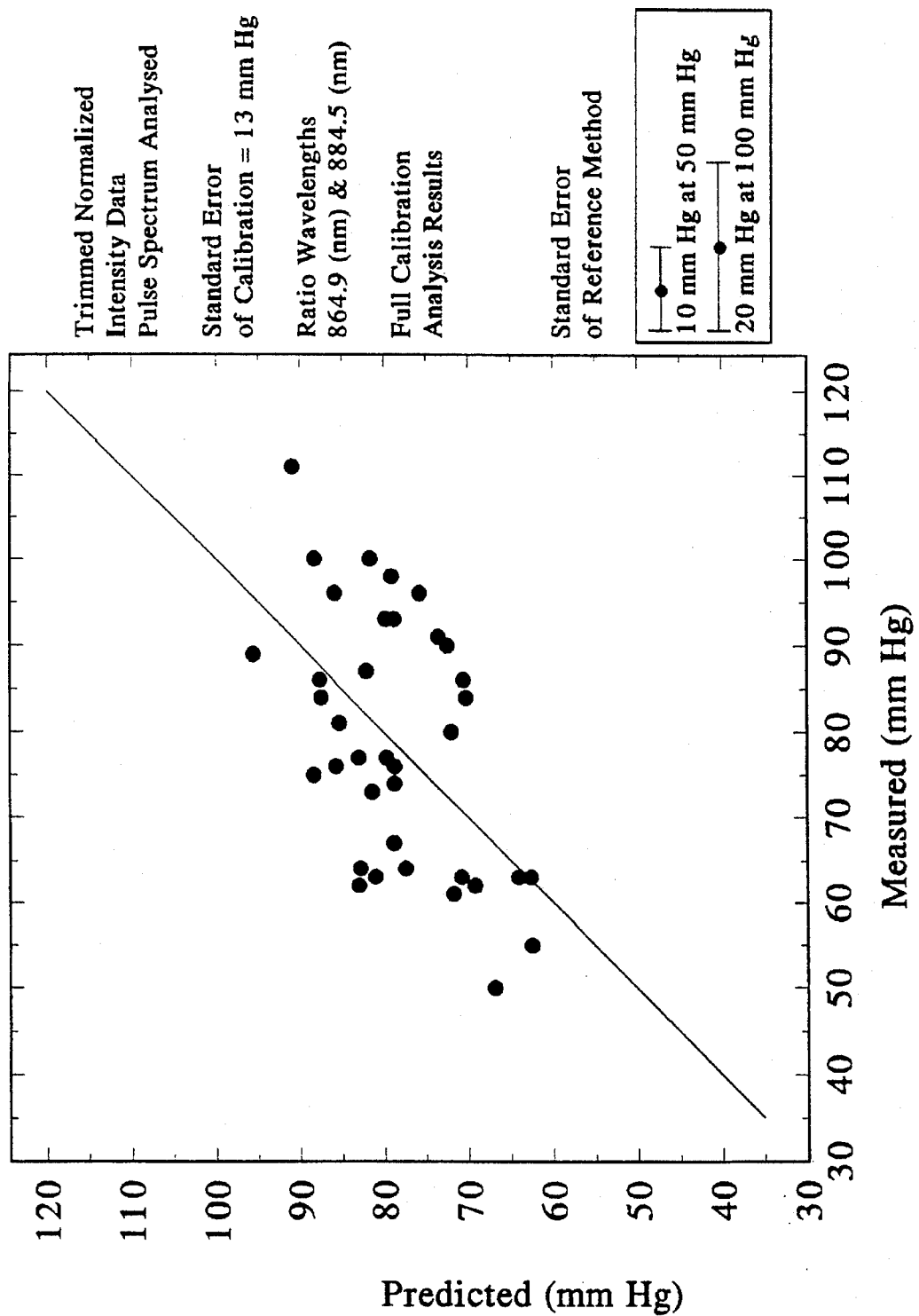
FIG. 42 is a plot of predicted pulse blood spectrum $PO_2$ vs. measured arterial blood $PO_2$ utilizing the best ratio algorithm.
Figure 43:
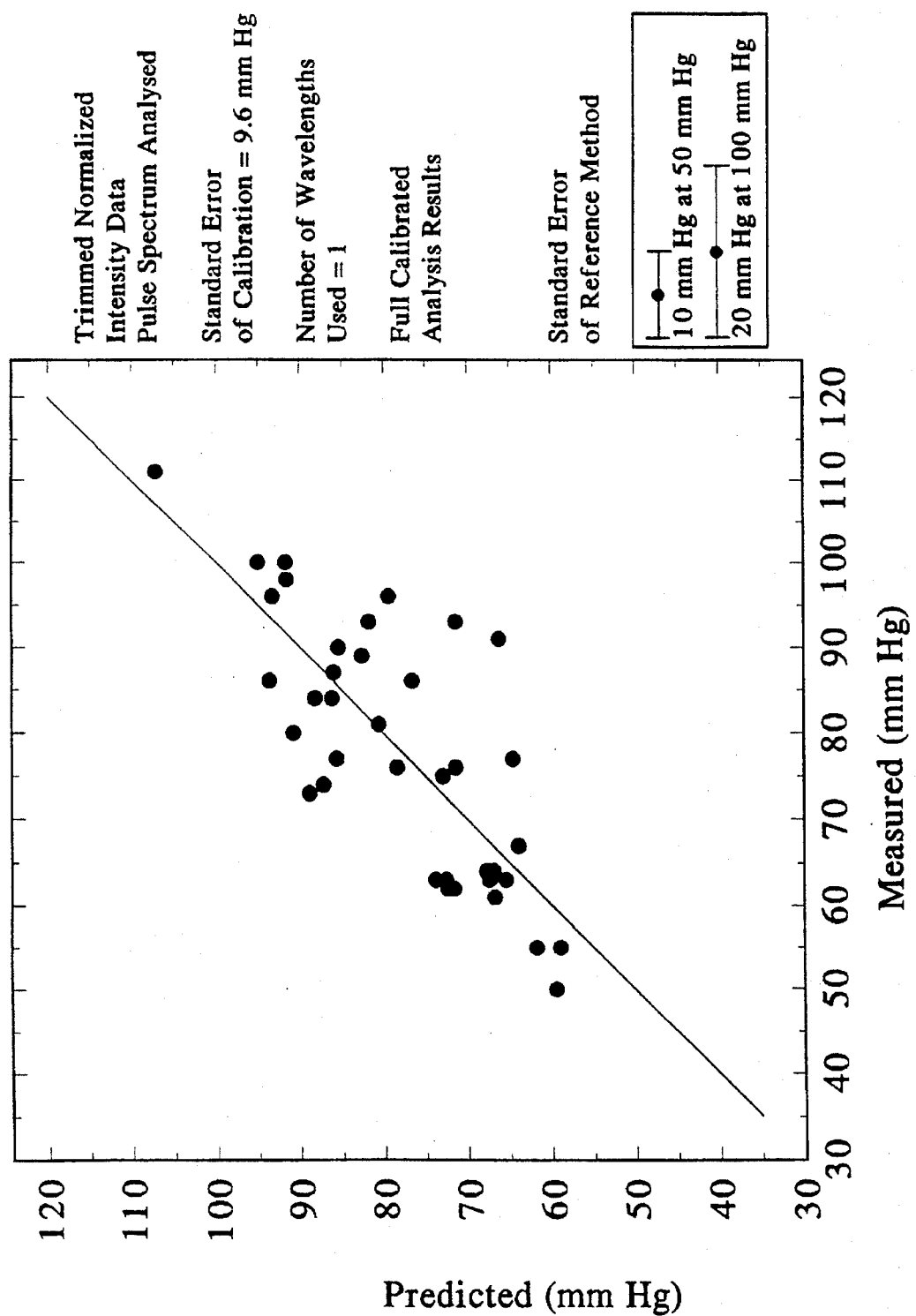
FIG. 43 is a plot of predicted pulse blood spectrum $PO_2$ vs. measured arterial blood $PO_2$ utilizing MLR.
Figure 44:
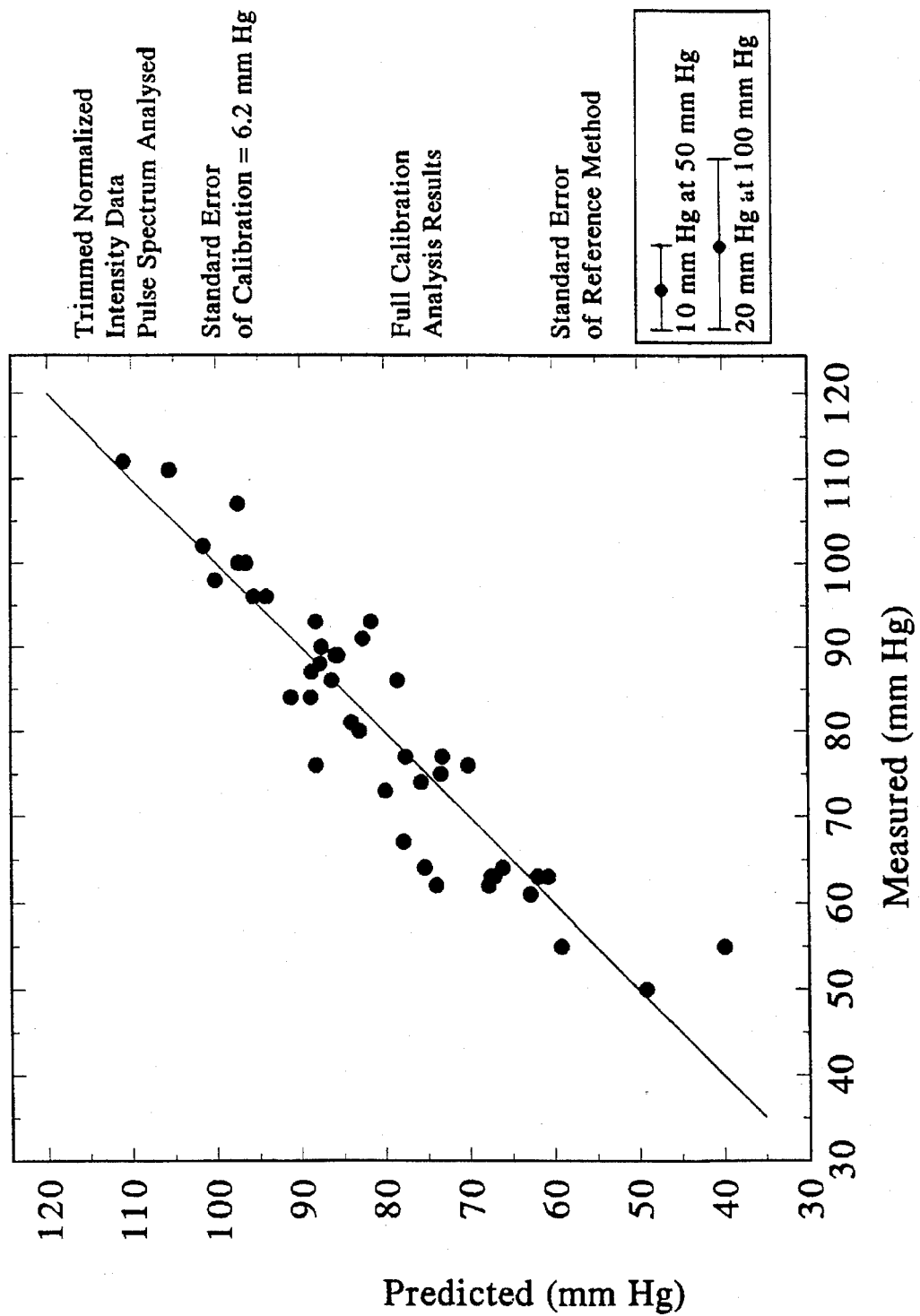
FIG. 44 is a plot of predicted pulse blood spectrum $PO_2$ vs. measured arterial blood $PO_2$ utilizing PLS.
Figure 45:
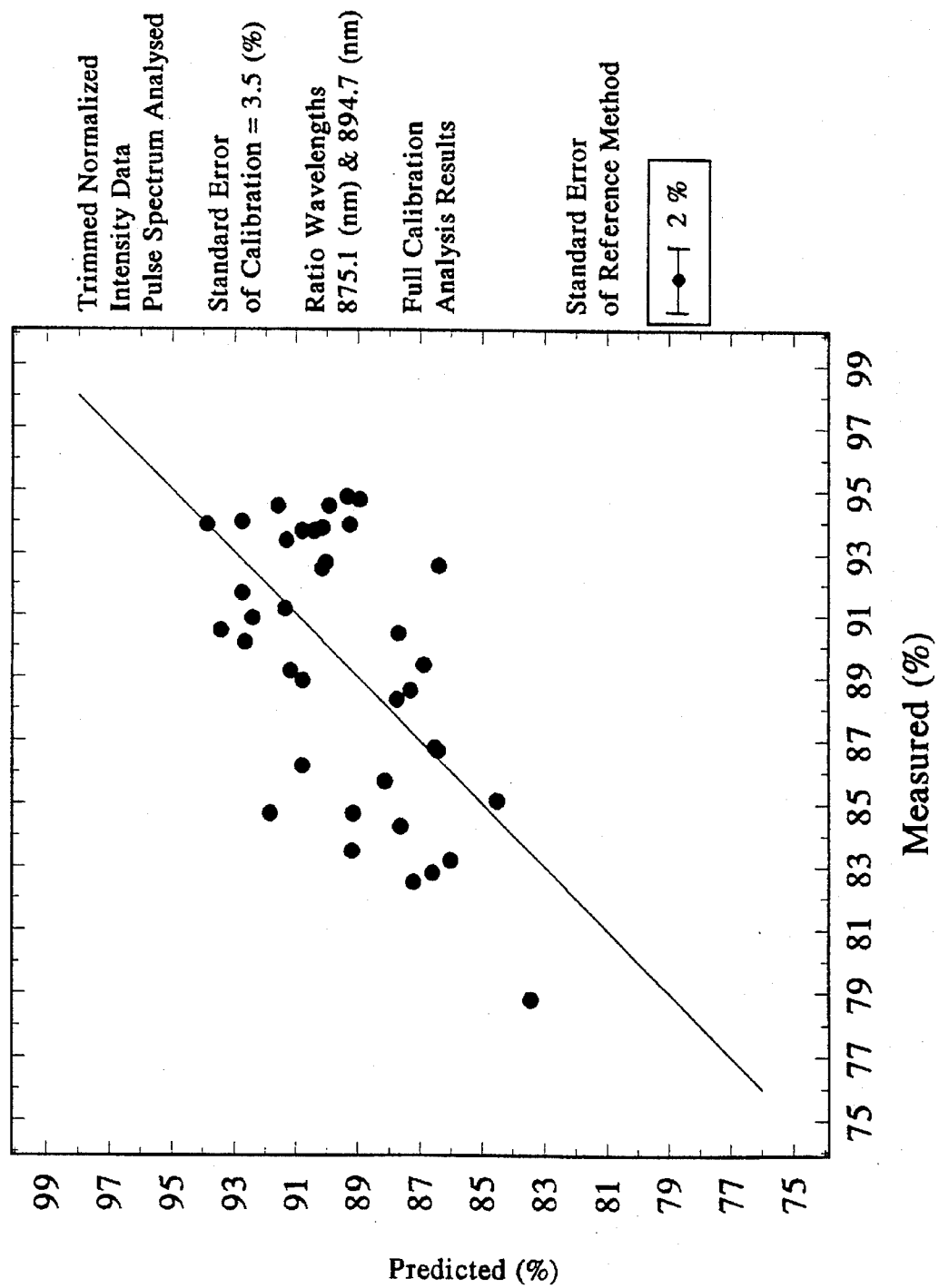
FIG. 45 is a plot of predicted pulse blood spectrum $O_2$ sat. vs. arterial blood measured $O_2$ sat. utilizing the best ratio algorithm.
Figure 46:
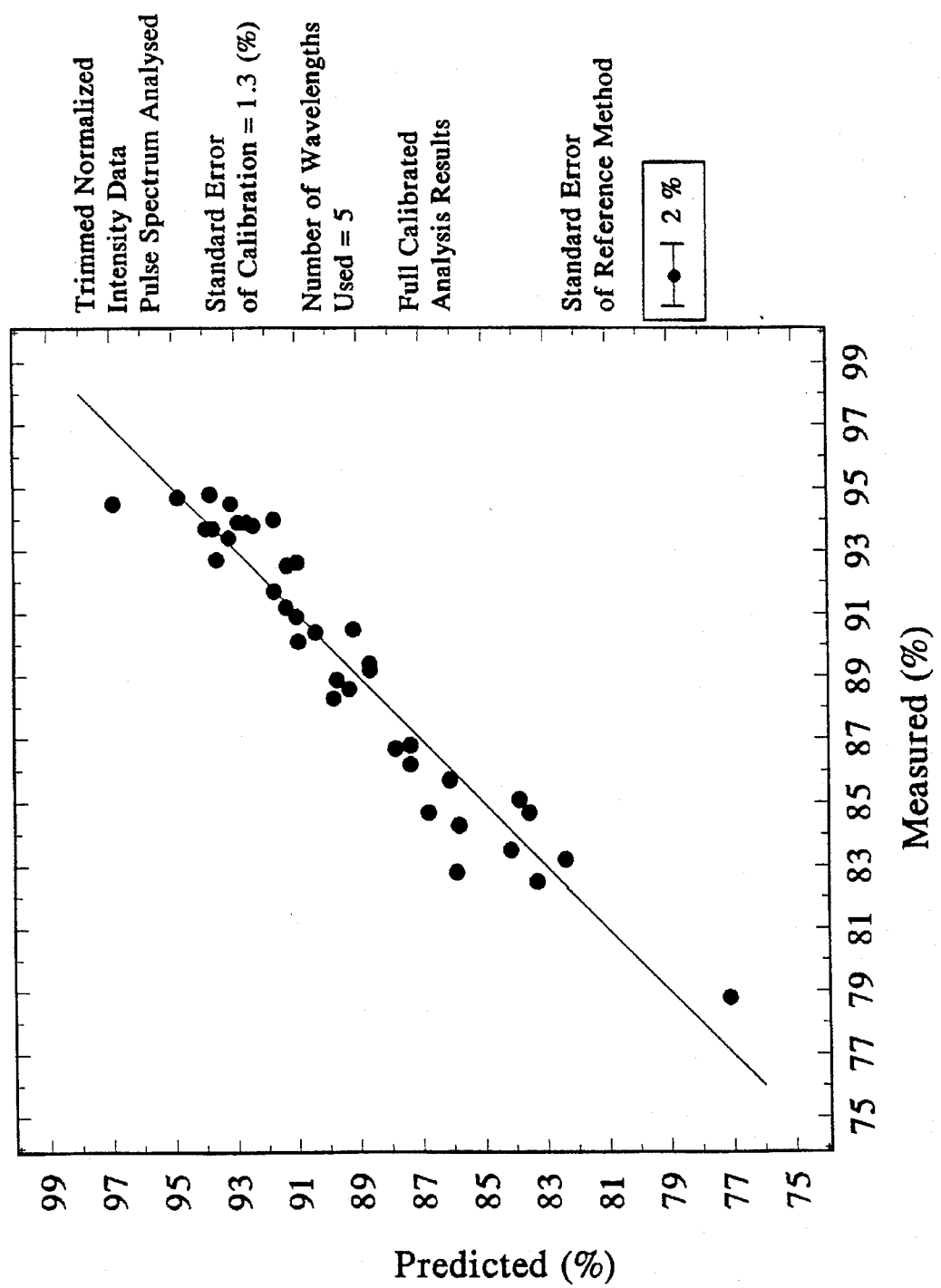
FIG. 46 is a plot of predicted pulse blood spectrum $O_2$ sat. vs. arterial blood measured $O_2$ sat. utilizing MLR.
Figure 47:
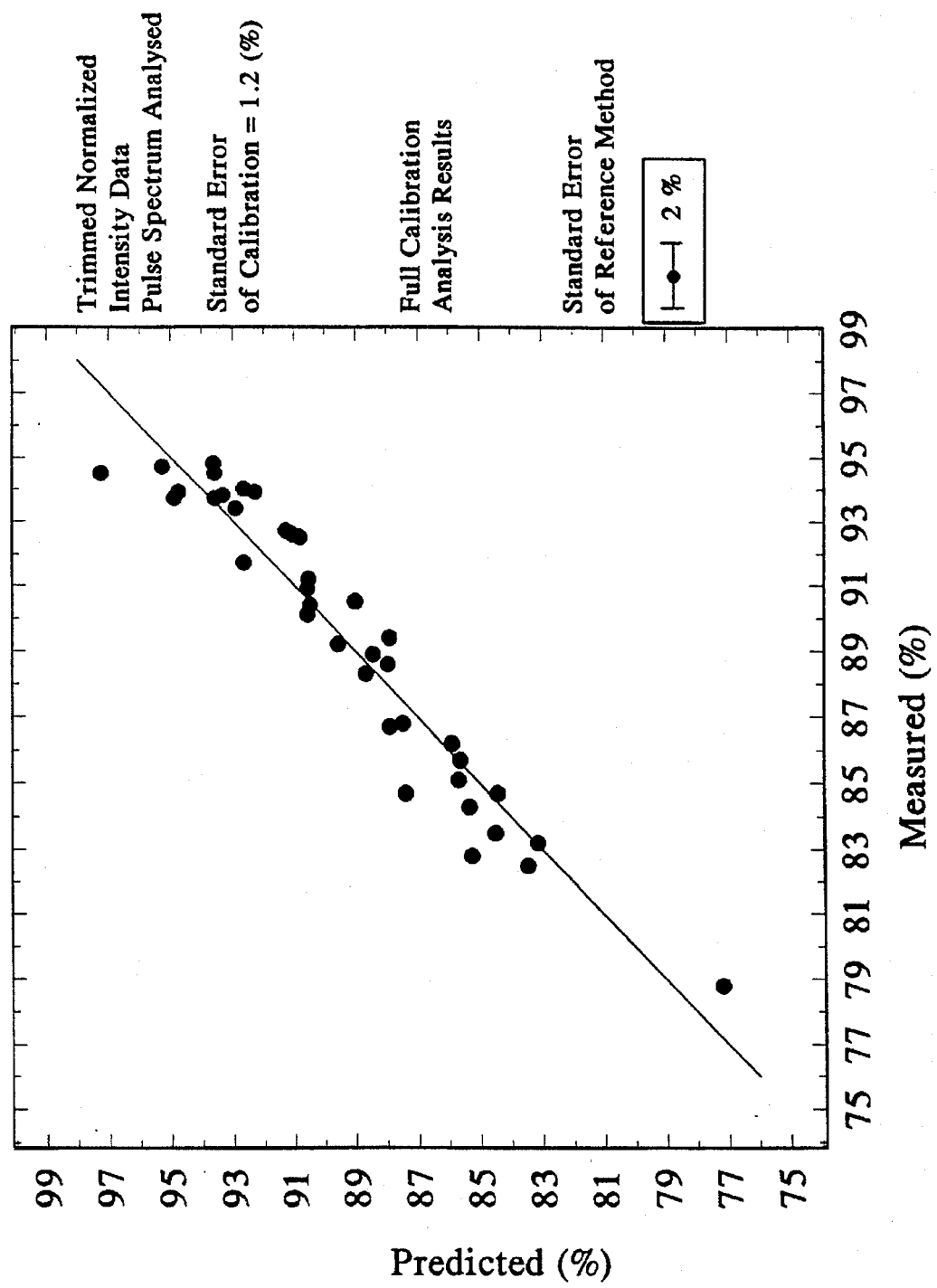
FIG. 47 is a plot of predicted pulse blood spectrum $O_2$ sat. vs. arterial blood measured $O_2$sat. utilizing PLS.

The results of MLR analysis of the pulse blood spectra is summarized in Table 6. The table lists the parameter number of wavelengths used in analysis and errors of calibration. The results are presented in FIGS. 37, 40, and 46.

TABLE 6

| MLR - Pulse Blood | | | |
|---|---|---|---|
| Parameter | Number of Wavelengths used | Number of Samples | SEC |
| pH | 7 | 32 | 0.03 |
| $PO_2$ | 1 | 42 | 9.6 |
| $[HCO_3^-]$ | 4 | 38 | 2.4 |
| $O_2$ sat. | 5 | 38 | 1.3 |

Partial Least Squares

The results of PLS analysis of the pulse blood spectra is summarized in Table 7. The table lists the parameter, number of factors, wavelength region, number of frequencies and standard error of calibration. The results are presented in FIGS. 38, 41, 44 and 47.

TABLE 7

| PLS - Pulse Blood | | | | |
|---|---|---|---|---|
| Parameter | Number of Factors | Wavelength Range | Number of Samples | SEC |
| pH | 7 | 700–800 nm | 39 | 0.02 |
| $PO_2$ | 3 | 652–955 nm | 36 | 6.2 |
| $[HCO_3^-]$ | 3 | 652–955 nm | 40 | 0.7 |
| $O_2$ sat. | 3 | 640–970 nm | 40 | 1.2 |

Although the data used to demonstrate proof of concept in the lamb study was recorded from 500 to 1000 nm, this is not the only frequency region of interest. Specifically the frequency region from 1000 to 2400 nm contains information on both hydrogen ion concentration and $CO_2$, (E. Watson and E. H. Baughman, "On-line analysis of caustic streams by near-infrared spectroscopy", Spectroscopy, vol 2, no 1 pp 44–48. The region from 1000 to 1400 nm is especially important as it allows for transmission measurements to be made easily through the finger, yet is not influenced by melanin content. Melanin which varies with ethnicity has a relatively flat absorbance response from 500 to 1000 nm, but ceases to absorb significantly above 1000 nm.

The detector used in our sheep study was a silicon detector with a response range of approximately 500 to 1000 nm. Detectors for measurement of frequencies in the region of 1000 to 2500 nm are numerous and include, Indium Gallium Arsenide, Indium Antimonide, Germanium, Lead Selenide, and Lead Sulfide. Additionally the range of response for silicon detectors has been increased to approximately 1200 nm through the use of coating powders and various techniques.

Figure 48:
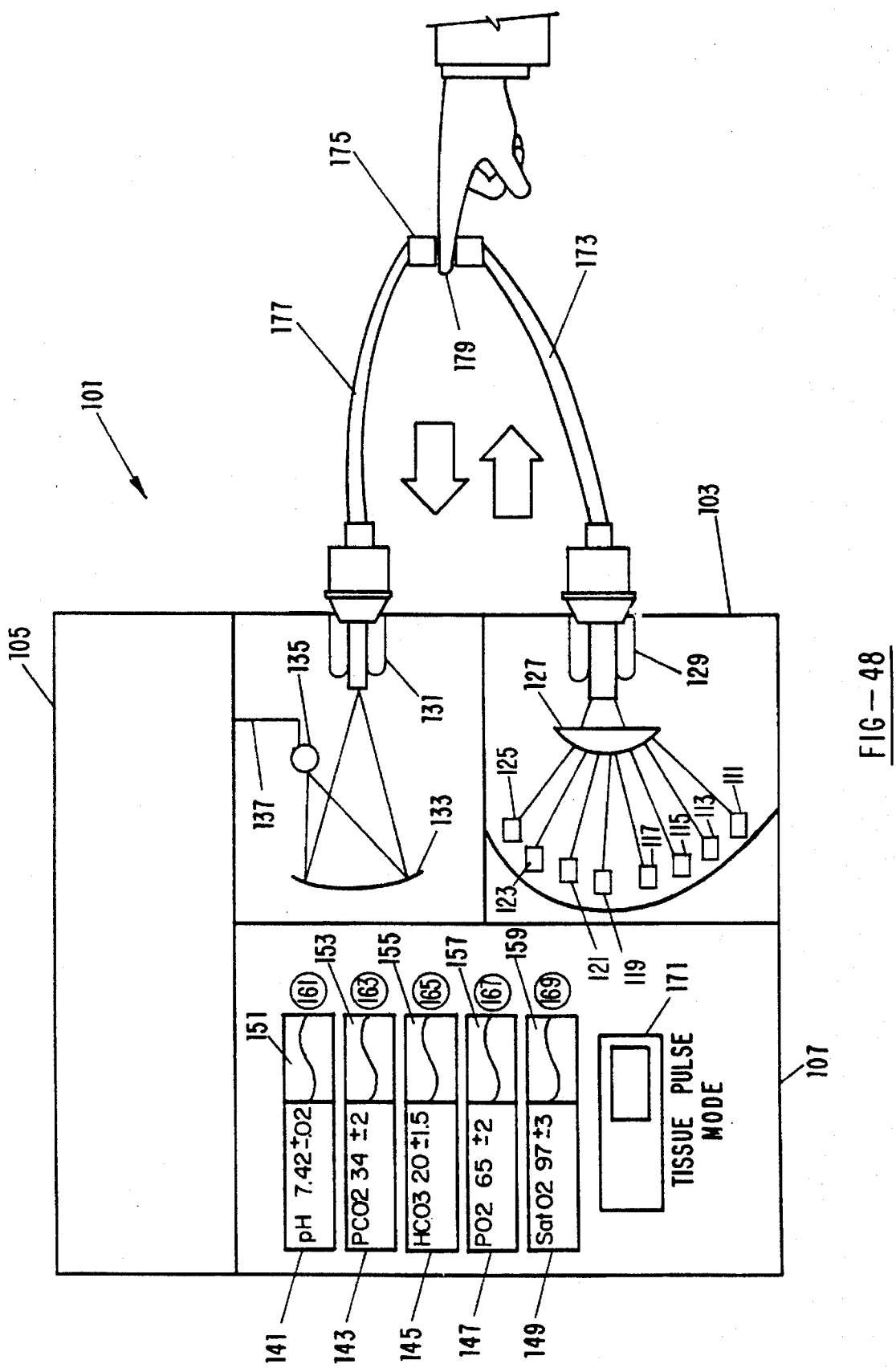
FIG. 48 is an alternate schematic of a noninvasive ABG monitor using multiple sources and a single detector.

With reference to FIG. 48, a second embodiment of a noninvasive blood gas monitor 101 of the present invention includes a spectrometer 103, an electronics and computer processing module 105 and a visual display module 107. Spectrometer 103 includes several light emitting diodes 111–125, a focusing lenses 127, fiber optic interface 129, a second fiber optic interface 131, a focusing mirror 133, a detector 135, and an electronic buss 137. Module 105 includes a microprocessor, memory containing the data preprocessing algorithms, multivariate calibration model and algorithms, and outlier detection methods. Visual display module 107 includes a pH display 141, a partial pressure of carbon dioxide display 143, a bicarbonate display 145, a partial pressure of oxygen display, 147, and an oxygen saturation display 149. Also included in module 107 are a pH trend display 151, a partial pressure of carbon dioxide trend display, 153, a bicarbonate trend display, 155, a partial pressure of oxygen trend display 157 and a oxygen saturation trend display 159. Visual display 107 also includes outlier lights 161–169 for each of the previous display analytes. Mode switch 171, which permits the doctor or other operator to change the mode of instrument operation from tissue mode to blood pulse mode, or vice-versa.

To transmit light from spectrometer 103 to the fingertip 67 of the patient, whose blood gases are being monitored, monitor 101 includes a source fiber optic bundle 173, which terminates at finger/fiber device 175. Receiving fiber optic 177 returns the light from finger/fiber holder 175 to fiber optic housing 131. Finger/fiber holder 175 allows transmission through finger 179 and allows for adequate holding of the finger.

In operation, multiple light emitting diode sources 111–125 emit light at discrete time intervals in the frequency region between 500 and 2400 nm. This light is focused on the end of fiber optic interface 129, via focusing lenses 127 and then via source fiber 173 to illuminate the tissue, bone, nail and blood therein. A portion of the light which is transmitted through fingertip 179 is then returned to spectrometer 103 by fiber bundle 177. The returning light is then focused by focusing mirror 133 onto detector 135, capable of detecting frequencies of light between 500 to 2400 nm.

The light intensities from the various diodes are then analyzed by processing unit 105 employing a appropriate algorithm. The instrument 101 can be operated in two different modes controlled by mode switch 171: (1) tissue determination mode; or (2) pulse blood mode.

Instrument 101 will display the current values of pH, $PCO_2$, $[HCO_3^-]$, $PO_2$ and $O_2$ sat. as well as the past history of said analyte in said displays 151–159. If a given analyte determination indicates that the analysis might be unreliable the outlier lights 161–169 will indicate such to the operator.

Present data indicates that pH, $PCO_2$, $[HCO_3^-]$, $PO_2$ and $O_2$ sat. can be determined noninvasively using wavelengths between 500–2500 nm. In addition, information is expected in the longer wavelength range 2500–7500 nm. This region cannot be used for noninvasive transmission measurements due to the large absorbances of water. However, use of wavelengths in this region are well suited for invasive, in-vivo measurements of blood gas parameters. Prior work by the authors has shown that glucose, urea and creatinine can be measured in biological systems by using attenuated total reflective sampling. This spectral region exhibits bands from the vibrational motion of molecules. $[HCO_3^-]$ and $CO_2$ have vibrational bands that can be used for calibration. Thus, use of mid-infrared spectroscopy can be used to measure two blood gas parameters.

Oxygen saturation and $PO_2$ could be determined invasively and in-vivo through the use of visible and near infrared spectroscopy. Specifically light transmitted by the fiber could be diffusely reflected by the blood and returned to the instrument for subsequent analysis. Thus, the combination of mid infrared spectroscopy with its sensitivity for vibrational spectroscopy coupled with visible/near-infrared spectroscopy with its sensitivity for electronic transition spectroscopy is ideally suited for invasive in-vivo continuous blood gas measurements.

Figure 49:
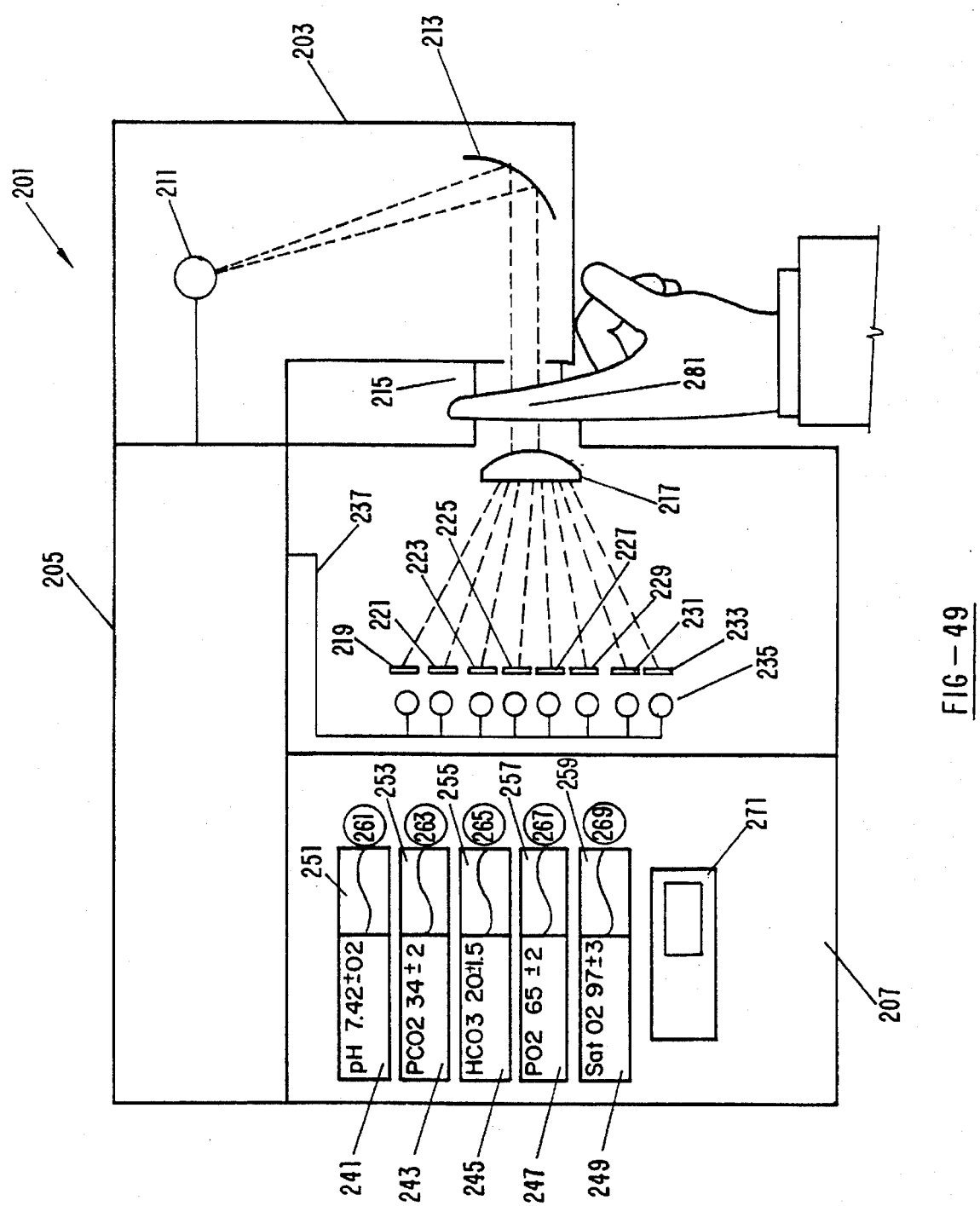
FIG. 49 is another alternate schematic of a noninvasive ABG monitor using a single source and multiple detectors.

With reference to FIG. 49, a third embodiment of a noninvasive blood gas monitor 201 of the present invention includes a spectrometer, 203, an electronics and computer processing module, 205, and a visual display module 207. Spectrometer 203 includes a single broad band source 211, a focusing mirror 213, finger holding device 215, diffuser 217, optical filters 219–233, and detector bank 235 and an electronic buss, 237. Module 205 includes a microprocessor, memory containing the data preprocessing algorithms, multivariate calibration model and algorithms, and outlier detection methods. Visual display module 207 includes a pH display 241, a partial pressure of carbon dioxide display 243, a bicarbonate display 245, a partial pressure of oxygen display, 247, and an oxygen saturation display 249. Also included in module 207 are a pH trend display 251, a partial pressure of carbon dioxide trend display, 253, a bicarbonate trend display, 255, a partial pressure of oxygen trend display 257 and a oxygen saturation trend display 259. Visual display 207 also includes outlier lights 261–269 for each of the previous display analytes. Mode switch 271, which permits the doctor or other operator to change the mode of instrument operation from tissue mode to blood pulse mode, or vice-versa.

In operation, light from source 211 is transmitted through finger 281 held in holder 215. The transmitted light is diffused by diffuser 217, filtered by optical filters 219–233 and subsequently recorded by detector bank 235.

The light intensities from the various detectors are then analyzed by processing unit 205 employing a appropriate algorithm. The instrument 201 can be operated in two different modes controlled by mode switch 271: (1) tissue determination mode; or (2) pulse blood mode.

Instrument 210 will display the current values of pH, PCO2, $[HCO_3^-]$, $PO_2$ and $O_2$ sat. as well as the past history of said analyte in said displays 251–259. If a given analyte determination indicates that the analysis might be unreliable the outlier lights 261–269 will indicate such to the operator.

Figure 50:
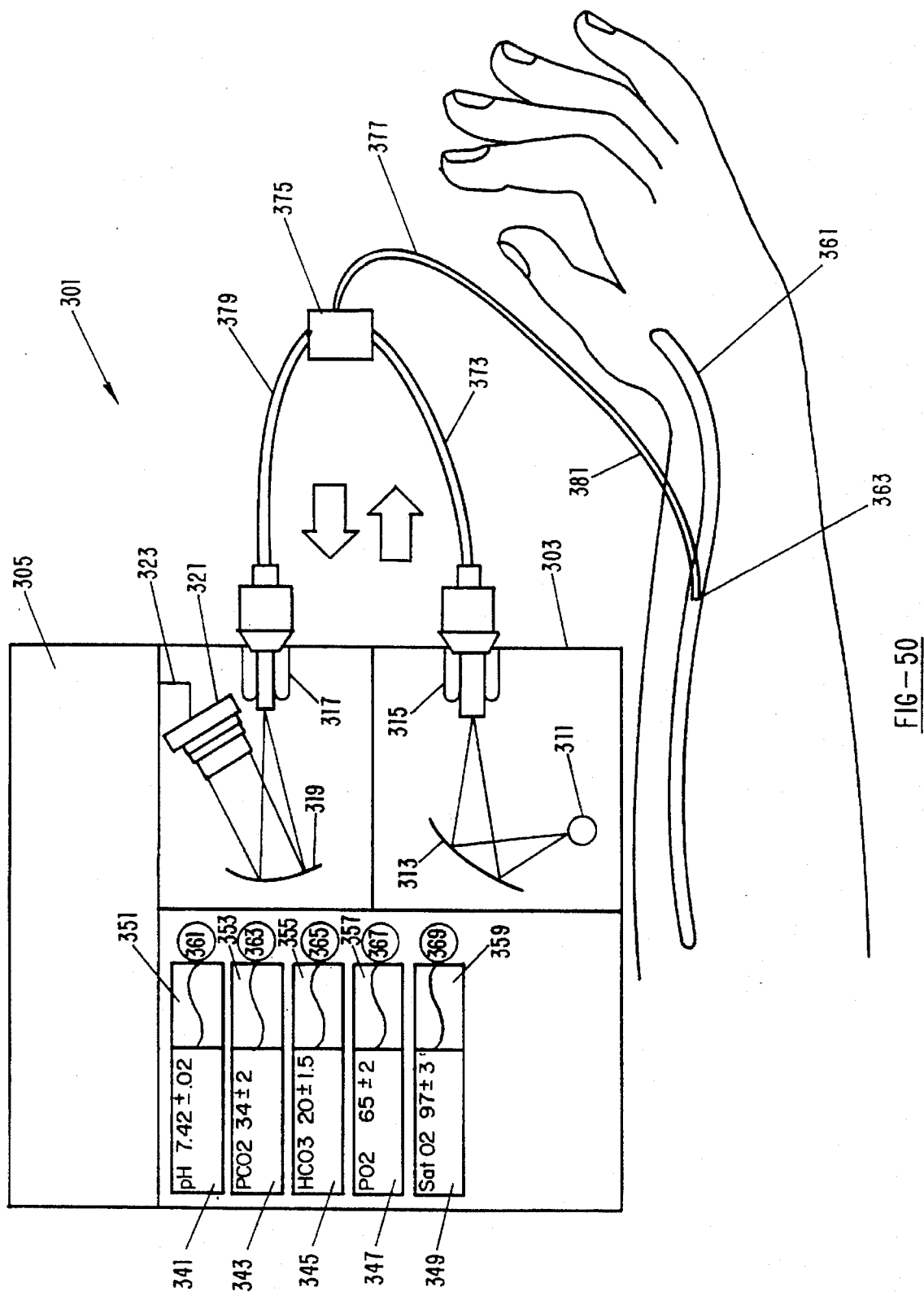
FIG. 50 is a schematic of an invasive ABG monitor of the present invention.

With reference to FIG. 50, invasive blood gas monitoring can be performed by the instrument shown in 301, the instrument includes a spectrometer, 303, an electronics and computer processing module, 305, and a visual display module 307. Spectrometer 303 includes a broad band light source 311 a focusing mirror 313, fiber optic interface 315, a second fiber optic interface 317, a grating 319, an array detector 321, and an electronic buss, 323. Module 305 includes a microprocessor, memory 35 containing the data preprocessing algorithms, multivariate calibration model and algorithms, and outlier detection methods. Visual display module 307 includes a pH display 341, a partial pressure of carbon dioxide display 343, a bicarbonate display 345, a partial pressure of oxygen display, 347, and an oxygen saturation display 349. Also included in module 307 are a pH trend display 351, a partial pressure of carbon dioxide trend display, 353, a bicarbonate trend display, 355, a partial pressure of oxygen trend display 357 and a oxygen saturation trend display 359. Visual display 307 also includes outlier lights 361–369 for each of the previous display analytes.

To transmit light from spectrometer 303 to the arterial vessel 361, in which blood gases are being monitored, monitor 301 includes a source fiber optic bundle 373, which terminates at junction 375 with subsequent formation of a source and receiving fiber 377. The receiving portion of optical bundle 377 returns the light to junction 375 with subsequent return of light to the instrument occurring through receiving fiber optic 379.

In operation, light source 311 or sources (not shown) emit light in the visible or infrared frequency regions. This light is focused on the end of fiber optic interface 315, via focusing mirror 313 and then via fibers 373 and 377 the light illuminates blood at the end of the fiber 363. The fiber optic probe is inserted through the skin 381 and into arterial vessel 361. A portion of the light which has interacted with the blood reenters fiber optic 377 and is returned to fiber junction 375. The light having interacted with the blood is returned to the spectrometer by fiber optic 379. The returning light is then separated by wavelength by grating 319 and reflected onto array detector 321, capable of detecting frequencies of light in the visible and infrared frequency region.

The light intensities at various wavelengths are then analyzed by processing unit 305 employing a appropriate algorithm. Instrument 301 will display the current values of pH, $PCO_2$, $[HCO_3^-]$, $PO_2$ and $O_2$ sat. as well as the past history of said analyte in said displays 351–359. If a given analyte determination indicates that the analysis might be unreliable the outlier lights 361–369 will indicate such to the operator.

Whereas the drawings and accompanying description have shown and described the preferred embodiment of the present invention, it should be apparent to those skilled in the art that various changes may be made in the form of the invention without affecting the scope thereof.

What we claim is:

1. A quantitative analysis instrument for noninvasive measurement of two or more blood gas parameters present in blood containing tissue of a human, said instrument comprising:
    a. a source of at least three different wavelengths of light, said wavelengths being in the range of 500 to 2500 nm;
    b. optics for directing said wavelengths of light into said tissue;
    c. at least one detector for measuring the intensities of at least a portion of said wavelengths of said light emerging from said tissue at, at least, three wavelengths of said light during the systolic and diastolic portions of the cardiac cycle;
    d. electronics for processing said measured intensities to estimate the values at least two of pH, $PCO_2$, and $[HCO_3^-]$ and a measure of oxygen saturation in said blood based on the intensity variations of said wavelengths of light due to blood pulsations; and
    e. means for indicating said estimated values of said blood gas parameters.

2. A quantitative analysis instrument for noninvasive spectroscopic measurement of tissue pH in humans, said instrument comprising:
    a. a source of at least three different wavelengths of light, said wavelengths being in the range of 500 to 2500 nm;
    b. optics for directing said wavelengths of light into human tissue;
    c. at least one detector for measuring the intensities of at least a portion of said wavelengths of said light emerging from said tissue at, at least, three wavelengths of said light;
    d. electronics for processing said measured intensities to estimate tissue pH values; and
    e. means for indicating said estimated values of tissue pH.

3. The analysis instrument of claim 2, wherein the said electronics utilizes a multivariate algorithm using at least two variables and a calibration model.

4. The analysis instrument of claim 3, wherein said algorithm is capable of using more spectral variables per sample than the number of calibration samples used to generate said model, and wherein each of said variables consists of at least one measured spectral intensity.

5. A quantitative analysis instrument for noninvasive spectroscopic measurement of blood pH in human tissue, said instrument comprising:
    a. a source of at least three different wavelengths of light, said wavelengths being in the range of 500 to 2500 mm;
    b. optics for directing said wavelengths of light into said human tissue;
    c. at least one detector for measuring the intensity of at least a portion of said wavelengths of said light emerging from said human tissue at, at least, three wavelengths of said light;
    d. electronics for processing said measured intensities to estimate blood pH values in said blood; and
    e. means for indicating said estimated values of blood pH.

6. The analysis instrument of claim 5, wherein the said electronics utilizes a multivariate algorithm using at least two variables and a calibration model.

7. The analysis instrument of claim 6, wherein said algorithm is capable of using more spectral variables per sample than the number of calibration samples used to generate said model, and wherein each of said variables consists of at least one measured spectral intensity.

8. The analysis instrument of claim 5, wherein said source generates said at least three different wavelengths of light in the range of 500–1000 nm.

9. The analysis instrument of claim 5, wherein said source generates said at least three different wavelengths of light in the range of 1000–2500 nm.

10. A quantitative analysis instrument for noninvasive spectroscopic measurement of arterial blood pH in tissue in a human, said instrument comprising:
    a. a source of at least three different wavelengths of light, said wavelengths being in the range of 500 to 2500 nm;
    b. optics for directing said wavelengths of light into tissue containing arterial blood;
    c. at least one detector for measuring the intensities of at least a portion of said wavelengths of said light emerging from said tissue at, at least, three wavelengths of said light during the systolic and diastolic portions of the cardiac cycle of said human;
    d. electronics for processing said measured intensities to estimate arterial blood pH values based on the intensity variations of said wavelengths of light due to blood pulsations; and e. means for indicating said estimated values of arterial blood pH.

11. The analysis instrument of claim 10, wherein the said electronics utilizes a multivariate algorithm using at least two variables and a calibration model.

12. The analysis instrument of claim 11, wherein said algorithm is capable of using more spectral variables per sample than the number of calibration samples used to generate said model, and wherein each of said variables consists of at least one measured spectral intensity.

13. The analysis instrument of claim 10, wherein said electronics contains memory means for storing a diastolic set of spectral intensities v. wavelengths and a systolic set of spectral intensities v. wavelengths and for processing said diastolic and systolic sets, to obtain an arterial blood specific set of spectral intensities v. wavelengths.

14. A quantitative analysis instrument for noninvasive spectroscopic measurement of tissue [$HCO_3^-$] in humans, said instrument comprising:
 a. a source of at least three different wavelengths of light, said wavelengths being in the range of 500 to 2500 nm;
 b. optics for directing said wavelengths of light into human tissue;
 c. at least one detector for measuring the intensities of at least a portion of said wavelengths of said light emerging from said tissue at, at least, three wavelengths of said light;
 d. electronics for processing said measured intensities to estimate tissue [$HCO_3^-$] values; and
 e. means for indicating said estimated values of tissue [$HCO_3^-$].

15. The analysis instrument of claim 14, wherein the said electronics utilizes a multivariate algorithm using at least two variables and a calibration model.

16. The analysis instrument of claim 15, wherein said algorithm is capable of using more spectral variables per sample than the number of calibration samples used to generate said model, and wherein each of said variables consists of at least one measured spectral intensity.

17. A quantitative analysis instrument for noninvasive spectroscopic measurement of blood [$HCO_3^-$] in human tissue, said instrument comprising:
 a. a source of at least three different wavelengths of light, said wavelengths being in the range of 500 to 2500 nm;
 b. optics for directing said wavelengths of light into said tissue;
 c. at least one detector for measuring the intensities of at least a portion of said wavelengths of said light emerging from said tissue at, at least, three wavelengths of said light;
 d. electronics for processing said measured intensities to estimate blood [$HCO_3^-$] values; and
 e. means for indicating said estimated values of blood [$HCO_3^-$].

18. The analysis instrument of claim 17, wherein the said electronics utilizes a multivariate algorithm using at least two variables and a calibration model.

19. The analysis instrument of claim 18, wherein said algorithm is capable of using more spectral variables per sample than the number of calibration samples used to generate said model, and wherein each of said variables consists of at least one measured spectral intensity.

20. A quantitative analysis instrument for noninvasive spectroscopic measurement of arterial blood [$HCO_3^-$] in tissue in a human, said instrument comprising:
 a. a source of at least three different wavelengths of light, said wavelengths being in the range of 500 to 2500 nm;
 b. optics for directing said wavelengths of light into tissue containing arterial blood;
 c. at least one detector for measuring the intensities of at least a portion of said wavelengths of said light emerging from said tissue at, at least, three wavelengths of said light during the systolic and diastolic portions of the cardiac cycle of said human;
 d. electronics for processing said measured intensities to estimate arterial blood [$HCO_3^-$] values based on the intensity variations of said wavelengths of light due to blood pulsations; and
 e. means for indicating said estimated values of arterial blood [$HCO_3^-$].

21. The analysis instrument of claim 20, wherein the said electronics utilizes a multivariate algorithm using at least two variables and a calibration model.

22. The analysis instrument of claim 21, wherein said algorithm is capable of using more spectral variables per sample than the number of calibration samples used to generate said model, and wherein each of said variables consists of at least one measured spectral intensity.

23. The analysis instrument of claim 20, wherein said electronics contains memory means for storing a diastolic set of spectral intensities v. wavelengths and a systolic set of spectral intensities v. wavelengths and for processing said diastolic and systolic sets, to obtain an arterial blood specific set of spectral intensities v. wavelengths.

24. A quantitative analysis instrument for noninvasive spectroscopic measurement of tissue $PCO_2$ in humans, said instrument comprising:
 a. a source of at least three different wavelengths of light, said wavelengths being in the range of 500 to 2500 nm;
 b. optics for directing said wavelengths of light into said human;
 c. at least one detector for measuring the intensities of at least a portion of said wavelengths of said light emerging from said tissue at, at least, three wavelengths of said light;
 d. electronics for processing said measured intensities to estimate tissue $PCO_2$ values; and
 e. means for indicating said estimated values of tissue $PCO_2$.

25. The analysis instrument of claim 24, wherein the said electronics utilizes a multivariate algorithm using at least two variables and a calibration model.

26. The analysis instrument of claim 25, wherein said algorithm is capable of using more spectral variables per sample than the number of calibration samples used to generate said model, and wherein each of said variables consists of at least one measured spectral intensity.

27. A quantitative analysis instrument for noninvasive spectroscopic measurement of blood $PCO_2$ in human tissue, said instrument comprising:
 a. a source of at least three different wavelengths of light, said wavelengths being in the range of 500 to 2500 nm;
 b. optics for directing said wavelengths of light into said tissue;
 c. at least one detector for measuring the intensities of at least a portion of said wavelengths of said light emerging from said tissue at, at least, three wavelengths of said light;
 d. electronics for processing said measured intensities to estimate blood $PCO_2$ values; and e. means for indicating said estimated values of blood $PCO_2$.

28. The analysis instrument of claim 27, wherein the said electronics utilizes a multivariate algorithm using at least two variables and a calibration model.

29. The analysis instrument of claim 28, wherein said algorithm is capable of using more spectral variables per sample than the number of calibration samples used to generate said model, and wherein each of said variables consists of at least one measured spectral intensity.

30. A quantitative analysis instrument for noninvasive spectroscopic measurement of arterial blood $PCO_2$ in tissue in a human, said instrument comprising:
   a. a source of at least three different wavelengths of light, said wavelengths being in the range of 500 to 2500 nm;
   b. optics for directing said wavelengths of light into tissue containing arterial blood;
   c. at least one detector for measuring the intensities of at least a portion of said wavelengths of said light emerging from said tissue at, at least, three wavelengths of said light during the systolic and diastolic portions of the cardiac cycle of said human;
   d. electronics for processing said measured intensities to estimate arterial blood $PCO_2$ values based on the intensity variations of said wavelengths of light due to blood pulsations; and
   e. means for indicating said estimated values of arterial blood $PCO_2$.

31. The analysis instrument of claim 30, wherein the said electronics utilizes a multivariate algorithm using at least two variables and a calibration model.

32. The analysis instrument of claim 31, wherein said algorithm is capable of using more spectral variables per sample than the number of calibration samples used to generate said model, and wherein each of said variables consists of at least one measured spectral intensity.

33. The analysis instrument of claim 30, wherein said electronics contains memory means for storing a diastolic set of spectral intensities v. wavelengths and a systolic set of spectral intensities v. wavelengths and for processing said diastolic and systolic sets, to obtain an arterial blood specific set of spectral intensities v. wavelengths.

34. A method of determining noninvasively at least one of pH, $[HCO_3^-]$, $PCO_2$ in a human, said method comprising steps of:
   a. generating light at three or more different wavelengths, said wavelengths being in the range of 500 nm to 2500 nm;
   b. noninvasively irradiating blood containing tissue with said wavelengths so that there is differential attenuation of at least some intensities of said wavelengths, said wavelength dependent differential attenuation being a function of said blood containing tissue and the unknown value of at least one of pH, $[HCO_3^-]$, and $PCO_2$ in said blood containing tissue;
   c. measuring said intensities of said wavelengths emerging from said blood containing tissue to obtain a set of at least three spectral intensities v. wavelengths; and
   d. estimating said value of said at least one of pH, $[HCO_3^-]$, and $PCO_2$, from said intensities emerging from said blood containing tissue, said value being within the physiological ranges observed in blood containing tissue.

35. The method as set forth in claim 34, wherein said method is used to determine pH, and further including the step of generating light at three more different wavelengths in the range of 500–1000 nm.

36. The method as set forth in claim 34, wherein said method is used to determine pH, and further including the step of generating light at three more different wavelengths in the range of 1000–2500 nm.

* * * * *